US012397053B2

(12) United States Patent
Coffin

(10) Patent No.: US 12,397,053 B2
(45) Date of Patent: *Aug. 26, 2025

(54) ENGINEERED VIRUS

(71) Applicant: Replimune Limited, Oxfordshire (GB)

(72) Inventor: Robert Stuart Coffin, London (GB)

(73) Assignee: Replimune Limited, Oxfordshire (GB)

(*) Notice: Subject to any disclaimer, the term of this patent is extended or adjusted under 35 U.S.C. 154(b) by 0 days.

This patent is subject to a terminal disclaimer.

(21) Appl. No.: 18/163,837

(22) Filed: Feb. 2, 2023

(65) Prior Publication Data

US 2023/0212531 A1 Jul. 6, 2023

Related U.S. Application Data

(63) Continuation of application No. 17/164,635, filed on Feb. 1, 2021, now Pat. No. 12,049,647, which is a continuation of application No. 16/068,830, filed as application No. PCT/GB2017/050038 on Jan. 9, 2017, now Pat. No. 10,947,513.

(30) Foreign Application Priority Data

| Jan. 8, 2016 | (GB) | 1600380 |
| Jan. 8, 2016 | (GB) | 1600381 |
| Jan. 8, 2016 | (GB) | 1600382 |

(51) Int. Cl.

| A61K 35/763 | (2015.01) |
| A61K 39/00 | (2006.01) |
| A61K 39/395 | (2006.01) |
| A61K 45/06 | (2006.01) |
| A61P 35/00 | (2006.01) |
| C07K 14/005 | (2006.01) |
| C07K 14/535 | (2006.01) |
| C07K 16/28 | (2006.01) |
| C12N 7/00 | (2006.01) |

(52) U.S. Cl.
CPC ...... *A61K 39/39558* (2013.01); *A61K 35/763* (2013.01); *A61K 39/3955* (2013.01); *A61K 45/06* (2013.01); *A61P 35/00* (2018.01); *C07K 14/005* (2013.01); *C07K 14/535* (2013.01); *C07K 16/2818* (2013.01); *C12N 7/00* (2013.01); *A61K 2039/505* (2013.01); *C12N 2710/16621* (2013.01); *C12N 2710/16622* (2013.01); *C12N 2710/16632* (2013.01); *C12N 2710/16633* (2013.01); *C12N 2710/16643* (2013.01); *C12N 2740/13022* (2013.01)

(58) Field of Classification Search
CPC ........ G01N 2333/165; G01N 2470/00; G01N 2470/04; G01N 33/543; G01N 2474/00; A61K 35/763; A61K 39/39558; A61K 48/00; A61K 38/193; A61K 2039/5254; A61K 2039/55522; A61K 2039/5256; A61K 2039/505; A61K 39/3955; A61K 45/06; A61P 35/00; A61P 37/02; A61P 37/04; A61P 9/10; A61P 31/20; C07K 14/005; C07K 14/535; C12N 2710/16632; C12N 2710/16643; C12N 15/869; C12N 15/86; C12N 2710/10032; C12N 15/8695; C12N 2710/16633

See application file for complete search history.

(56) References Cited

U.S. PATENT DOCUMENTS

| 5,122,458 A | 6/1992 | Post et al. |
| 5,168,062 A | 12/1992 | Stinski |
| 5,288,641 A | 2/1994 | Roizman |
| 5,328,688 A | 7/1994 | Roizman |
| 5,385,839 A | 1/1995 | Stinski |
| 5,599,691 A | 2/1997 | Roizman |
| 5,602,007 A | 2/1997 | Dunn et al. |
| 5,698,531 A | 12/1997 | Nabel et al. |
| 5,824,318 A | 10/1998 | Mohr et al. |
| 5,846,707 A | 12/1998 | Roizman |
| 6,040,169 A | 3/2000 | Brown et al. |
| 6,071,692 A | 6/2000 | Roizman |
| 6,120,773 A | 9/2000 | Roizman |
| 6,172,047 B1 | 1/2001 | Roizman et al. |
| 6,297,219 B1 | 10/2001 | Nabel et al. |
| 6,340,673 B1 | 1/2002 | Roizman et al. |
| 6,423,528 B1 | 7/2002 | Brown et al. |
| 6,428,968 B1 | 8/2002 | Molnar-Kimber et al. |
| 6,649,157 B2 | 11/2003 | Coffey et al. |
| 6,770,274 B1 | 8/2004 | Martuza et al. |
| 7,063,835 B2 | 6/2006 | Coffin |

(Continued)

FOREIGN PATENT DOCUMENTS

| EP | 1235853 B1 | 7/2009 |
| JP | 2013511549 A | 4/2013 |

(Continued)

OTHER PUBLICATIONS

Jean-François Fonteneau et al. Oncoimmunology. 2016; 5(1): e1066961, published online Aug. 12, 2015. doi: 10.1080/2162402X.2015.1066961.*

Hu et al. Cancer Therapy: Clinical, published on Nov. 22, 2006, pp. 6737-6747.*

NIH, National Cancer Institute (NCI)'s Dictionary of Cancer terms on line searched by on Sep. 25, 2024. p. 1-1.*

Fielding et al. "A hyperfusogenic gibbon apeleukemia envelope glycoprotein: targeting of a cytotoxic gene by ligand display", Hum Gene Ther. Apr. 10, 2000;11(6):817-26.

Majid et al. Recombinant Vesicular Stomatitis Virus (VSV) and Other Strategies in HCV Vaccine Designs and Immunotherapy. Tan SL, (Ed.) Hepatitis C Viruses: Genomes and Molecular Biology, Ch. 15. Norfolk (UK): Horizon Bioscience (2006).

(Continued)

*Primary Examiner* — Bao Q Li

(74) *Attorney, Agent, or Firm* — Norton Rose Fulbright US LLP

(57) ABSTRACT

The present invention relates to oncolytic virus comprising: (i) a GM-CSF-encoding gene; and (ii) an immune co-stimulatory pathway activating molecule or an immune co-stimulatory pathway activating molecule-encoding gene.

30 Claims, 33 Drawing Sheets

Specification includes a Sequence Listing.

(56) References Cited

U.S. PATENT DOCUMENTS

| | | |
|---|---|---|
| 7,223,593 B2 | 5/2007 | Coffin |
| 7,537,924 B2 | 5/2009 | Coffin |
| 7,749,745 B2 | 7/2010 | Johnson et al. |
| 7,981,669 B2 | 7/2011 | Coffin et al. |
| 8,273,568 B2 | 9/2012 | Martuza et al. |
| 8,277,818 B2 | 10/2012 | Coffin |
| 8,361,978 B2 | 1/2013 | Rabkin et al. |
| 8,470,577 B2 | 6/2013 | Johnson et al. |
| 8,679,830 B2 | 3/2014 | Coffin et al. |
| 8,680,068 B2 | 3/2014 | Coffin |
| 8,703,120 B2 | 4/2014 | Martuza et al. |
| 8,871,193 B2 | 10/2014 | Johnson et al. |
| 8,986,672 B2 | 3/2015 | Zhang et al. |
| 9,487,581 B2 | 11/2016 | Abate et al. |
| 9,492,482 B2 | 11/2016 | Beech et al. |
| 9,789,182 B2 | 10/2017 | Graziano et al. |
| 9,827,307 B2 | 11/2017 | Rabkin et al. |
| 9,868,961 B2 | 1/2018 | Allison et al. |
| 10,039,796 B2 | 8/2018 | Zhang et al. |
| 10,287,252 B2 | 5/2019 | Cowley et al. |
| 10,301,600 B2 | 5/2019 | Coffin |
| 10,555,981 B2 | 2/2020 | Silvestre et al. |
| 10,570,377 B2 | 2/2020 | Coffin |
| 10,612,005 B2 | 4/2020 | Coffin |
| 10,626,377 B2 | 4/2020 | Coffin |
| 10,765,710 B2 | 9/2020 | Zitvogel et al. |
| 10,947,513 B2 | 3/2021 | Coffin |
| 11,427,810 B2 * | 8/2022 | Coffin ............... C07K 16/2818 |
| 11,473,063 B2 * | 10/2022 | Coffin ............... C07K 14/005 |
| 2003/0091537 A1 | 5/2003 | Coffin |
| 2008/0014175 A1 | 1/2008 | Hallahan et al. |
| 2010/0297072 A1 | 11/2010 | DePinho |
| 2011/0044953 A1 | 2/2011 | Allison et al. |
| 2013/0202639 A1 | 8/2013 | Kousoulas et al. |
| 2014/0154216 A1 | 6/2014 | Coffin |
| 2014/0271677 A1 | 9/2014 | Palese et al. |
| 2015/0232812 A1 | 8/2015 | Coffin |
| 2015/0283234 A1 | 10/2015 | Graziano et al. |
| 2016/0040186 A1 | 2/2016 | Liu |
| 2021/0252135 A1 | 8/2021 | Coffin |
| 2021/0254019 A1 | 8/2021 | Coffin |
| 2022/0056480 A1 | 2/2022 | Bell et al. |

FOREIGN PATENT DOCUMENTS

| | | | |
|---|---|---|---|
| JP | 2015/508156 A | 3/2015 | |
| JP | 2016509045 A | 3/2016 | |
| WO | 97/12623 A1 | 4/1997 | |
| WO | 9830707 A2 | 7/1998 | |
| WO | 2001/53505 A2 | 7/2001 | |
| WO | 2001/53506 A2 | 7/2001 | |
| WO | 2005/011715 A1 | 2/2005 | |
| WO | 2006/002394 A2 | 1/2006 | |
| WO | 2006/048749 A1 | 5/2006 | |
| WO | 2007/052029 A1 | 5/2007 | |
| WO | 2007/123737 A2 | 11/2007 | |
| WO | 2010042189 A2 | 4/2010 | |
| WO | 2011063309 A1 | 5/2011 | |
| WO | 2011/118866 A1 | 9/2011 | |
| WO | 2012/038606 A1 | 3/2012 | |
| WO | 2013/038066 A1 | 3/2013 | |
| WO | 2013112942 A1 | 8/2013 | |
| WO | WO2014022138 A2 * | 2/2014 | ........... A61K 39/395 |
| WO | WO2014036412 A2 * | 3/2014 | ............. A61K 39/00 |
| WO | WO2014036412 A3 * | 3/2014 | ............. C07K 16/28 |
| WO | 2014/066532 A1 | 5/2014 | |
| WO | 2014128235 A1 | 8/2014 | |
| WO | 2015032755 A1 | 3/2015 | |
| WO | 2015/059303 A1 | 4/2015 | |
| WO | 2015/077624 A1 | 5/2015 | |
| WO | 2015066042 A1 | 5/2015 | |
| WO | 2015/128313 A1 | 9/2015 | |
| WO | 2015/153417 A1 | 10/2015 | |
| WO | 2016/008976 A1 | 1/2016 | |
| WO | 2016/118865 A1 | 7/2016 | |
| WO | 2017/118864 A1 | 7/2017 | |
| WO | 2017/118866 A1 | 7/2017 | |
| WO | 2017118867 A1 | 7/2017 | |
| WO | 2017/181420 A1 | 10/2017 | |
| WO | 2018127713 A1 | 7/2018 | |

OTHER PUBLICATIONS

Malhotra et al. Use of an Oncolytic Virus Secreting GM-CSF as Combined Oncolytic and Immunotherapy for Treatment of Colorectal and Hepatic Adenocarcinomas, 141(4) Surgery 520-529 (Apr. 2007).

Marabelle et al., "Intratumoral Anti-CTLA-4 Therapy: Enhancing Efficacy While Avoiding Toxicity", Clin Cancer Res. 2013, 19(19):5261-3.

McDonald et al. A measles virus vaccine strain derivative as a novel oncolytic agent against breast cancer, 99 Breast Cancer Research and Treatment 177-184 (2006).

Msaouel et al. Attenuated oncolytic Measles Virus strains as cancer therapeutics, 13(9) Curr. Pharm. Biotechnol. 1732-41 (Jul. 1, 2012).

Murata et al: "X40 costimulation synergizes with GM-CSF whole-cell vaccination to overcome established CD8+ T cell tolerance to an endogenous tumor antigen", J Immunol. Jan. 15, 2006;176(2):974-83.

Nakamori et al. Potent Antitumor Activity After Systemic Delivery of a Doubly Fusogenic Oncolytic Herpes Simplex Virus Against Metastatic Prostate Cancer, 60 The Prostate 53-60 (2004).

Nakano et al., Journal of Japan Surgical Society, 2001,102, Extra Issue, p. 82, No. SF4e-4.

Office Action issued in European Patent Application No. 1770385, dated May 21, 2019.

Oliveira et al. Poxvirus Host Range Genes and Virus-Host Spectrum: A Critical Review, 9(11) Viruses 2017 331 (Nov. 7, 2017).

Output from antibodies-online.com search for CTLA-4 Antibodies (performed Nov. 24, 2021), available at https://www.antibodies-online.eom/search.php#5qk9.

Output from Antibodypedia search for CTLA-4 Antibodies (performed Nov. 24, 2021), available at https://www.antibodYPedia.eom/gene/1 9961/CTLA4.

Output from Biocompare search for CTLA-4 Antibodies (performed Nov. 24, 2021), available at https://www.biocompare.com/Search-Antibodies/?search=CTLA-4&said=0.

Output from the National Institutes of Health (NIH) National Center for Biotechnology Information (NCBI) Taxonomy Browser searches for "herpesviridae", "poxviridae", "adenoviridae", "retroviridae", "rhabdoviridae", "paramyxoviridae", and "reoviridae" (performed Nov. 3, 2021), available at: https://www.ncbi.nlm.nih.gov/Taxonomy/Browser/wwwtax.cgi7mode =Root.

Patentee's response to EPO communication dtd Sep. 25, 2009, EP No. 17701910.6.

Pentcheva-Hoang et al. B7-1 and B7-2 Selectively Recruit CTLA-4 and CD28 to the Immunological Synapse, 21 Immunity 401-413 (Sep. 2004).

Petition for Post-Grant Review of U.S. Pat. No. 10,947,513, filed Dec. 15, 2021 with the TTAB, Petitioner—Transgene and Bioinvent International AB.

Piasecki et al., "Talilmogene laherparepvec increases the anti-tumor efficacy of the anti-PD-1 Abstract, Apr. 19, 2015 Immune checkpoint blockade, " AACR Annual Meeting Presentation.

Reese, "Abstract IA24: New frontiers in oncolytic virus therapy," Cancer Immunology Research, 2016, 4(11):1A24-1A24.

Reoviridae Information from Virus Pathogen Resource (ViPR) retrieved on Nov. 4, 2021, available at https://www.viprbrc.org/brc/aboutPathogen.spg?decorator=reo.

Ribas, Clinical Development of the Anti-CTLA-4 Antibody Tremelimumab, 37(5) Seminars in Oncology 450-454 (Oct. 2010).

Riedel et al. Components and Architecture of the Rhabdovirus Ribonucleoprotein Complex, 12(9) Viruses 2020 959 (Aug. 2020).

Robbins et al; "Viral Vectors for Gene Therapy"; Pharmacol, Ther.; vol. 80, No. 1; pp. 35-47; 1998.

Robinson et al., "Novel Immunocompetent Murine Tumor Model for Evaluation of Conditionally Replication-Competent (Oncolytic) Murine Adenoviral Vectors," Journal of Virology, 2009, 83(8):3450-3462.

(56) References Cited

OTHER PUBLICATIONS

Rojas et al. Defining Effective Combinations of Immune Checkpoint Blockade and Oncolytic Virotherapy, 21(24) Clin. Cancer Res. 5543-51 (Dec. 2015).
Saha et al. The Adenovirus Genome Contributes to the Structural Stability of the Virion, 6(9) Viruses 2014 3563-3583 (Sep. 24, 2014).
Salzberg, Open questions: How many genes do we have? 16 BMC Biology 94 (Aug. 20, 2018).
Schirrmann et al., "Transient Production of scFv-Fc Fusion Proteins in Mammalian Cells", Antibody Engineering, 2010, vol. 2; Chapter 30, p. 387-398, © Springer-Verlag Berlin Heidelberg.
Senzer et al., "Phase II Clinical Trial of a Granulocyte-Macrophage Colony-Stimulating Factor-Encoding, Second-Generation Oncolytic herpesvirus in Patients with Unresectable Metastatic Melanoma" Journal of Clinical Oncology, 2009, 27(34):5763-5771.
Shan et al., "Characterization of scFv-Ig Constructs Generated from the Anti-CD20 mAb 1F5 Using Linker Peptides of Varying Lengths", Journal of Immunology, 1999, 162:6589-6595.
Sharp and Li, The codon adaptation index—a measure of directional synonymous codon usage bias, and its potential applications, 15(3) Nucleic Acids Research 1281-95 (1987).
Simpson et al., "Combination of a Fusogenic Glycoprotein, Prodrug activation, and Oncolytic Herpes Simplex Virus for Enhanced Local Tumor Control," Cancer Research, 2006, 66(9):4835-4842.
Singh et al. Oncolytic viruses & their specific targeting to tumour cells, 136 Indian J. Med. Res. 571-584 (Oct. 2012).
Sinkovics and Horvath, Natural and genetically engineered viral agents for oncolysis and gene therapy of human cancers, 56 Arch. Immunol. Ther. Exp. 3-59 (2008).
Smith et al. Studies on the Use of Viruses in the Treatment of Carcinoma of the Cervix, 9(6) Cancer 1211-18 (Nov.-Dec. 1956).
Sokolowski et al., "Oncolytic virotherapy using herpes simplex virus: how far have we come?" Oncolytic Virotherapy, 2015, 4:207-219.
Species list extracted from International Committee on Taxonomy of Viruses (ICTY) Master Species List (Jul. 20, 2021), available at: https://talk.ictvonline.org/taxonomy/vmr/.
Statement of Grounds of Opposition from the Opponent, Margaret Dixon Limited, dated Jun. 7, 2021, EP3400293 (EP Appl. No. 17701910.6).
Study Details for Clinical Trial NCT02272855 "A Study of Combination Treatment With HF10 and Ipilimumab in Patients With Unresectable or Metastatic Melanoma", last updated Sep. 26, 2018, available at: https://clinicaltrials.gov/ct2/show/NCT02272855.
Study Details for Clinical Trial NCT02620423 "Study of Pembrolizumab with REOLYSIN® and Chemotherapy in Patients With Advanced Pancreatic Adenocarcinoma", last updated Sep. 13, 2018, available at: https://clinicaltrials.gov/ct2/show/NCT02620423.
Sumimoto et al: "GM-CSF and B7-1 (CD80) co-stimulatory signals co-operate in the induction of effective anti-tumor Immunity in syngeneic mice", Int J Cancer. Nov. 14, 1997;73(4):556-61.
Summary of Characteristics of Commercial Viral Vectors from ThermoFisher Scientific, retrieved Nov. 4, 2021, available at https://www.thermofisher.com/us/en/home/references/gibco-cell-culture-basics/transfection-basics/gene-delivery-technologies/viral-delivery/viral-vectors.html.
Tan et al. Combination therapy of oncolytic herpes simplex virus HF10 and bevacizumab against experimental model of human breast carcinoma xenograft, 136 Int. J. Cancer 1718-30 (2015).
Terada K. et al, "Development of a rapid method to generate multiple oncolytic HSV vectors Gene Therapy, vol. 13, No. 8, (Apr. 1, 2006), pp. 705-714 and their in vivo evaluation using syngeneic mouse tumor models".
Tesfay et al. PEGylation of Vesicular Stomatitis Virus Extends Virus Persistence in Blood Circulation of Passively Immunized Mice, 87(7) Journal of Virology 3752-59 (Apr. 2013).
Third Party Submission submitted in Related U.S. Appl. No. 16/068,816, dated Jul. 16, 2019.

Third Party Submission submitted in Related U.S. Appl. No. 16/068,823, dated Jul. 18, 2019.
Third Party Submission submitted in Related U.S. Appl. No. 16/068,826, dated Aug. 7, 2019.
Third Party Submission submitted in Related U.S. Appl. No. 16/068,830, dated Jul. 18, 2019.
Todo, Tomoki, Armed oncolytic herpes simplex viruses for brain tumor therapy, 208-213, Cell Adhesion* Migration 2:3, Jul./Aug./Sep. 2008.
Van den Wollenberg et al. Replicating reoviruses with a transgene replacing the codons for the head domain of the viral spike, 22 Gene Therapy 267-279 (2015).
Wennier et al. Bugs and Drugs: Oncolytic Virotherapy in Combination with Chemotherapy, 13(9) Curr. Pharm. Biotechnol. 1817-33 (Jul. 2012).
Wertz et al. Adding genes to the RNA genome of vesicular stomatitis virus: positional effects on stability of expression, 76(15) J. Virol. 7642-50 (Aug. 2002).
Willemsen and Zwart, On the stability of sequences inserted into viral genomes, 5(2) Virus Evolution vez045 (Jul. 2019).
Yan et al., "Developing Novel Oncolytic Adenoviruses through Bioselection," Journal of Virology, 2003, 77(4):2640-2650.
Yang et al. Cascade regulation of vaccinia virus gene expression is modulated by multistage promoters, 447(1-2) Virology 213-220 (Dec. 2013).
Yen et al. Vaccinia virus infection & temporal analysis of virus gene expression: Part 2, 2009(26) J. Vis. Exp. 1169 (Apr. 2009).
Yi et al Cancer Res 2007, 67 20 10027-10037.
Yo, Y-T et al: "Coexpression of Flt3 ligand and GM-CSF genes modulates immune responses induced by HER2/neu DNA vaccine", Cancer Gene Ther. Nov. 2007;14(11):904-17.
Ahlers et al: "A push-pull approach to maximize vaccine efficacy: abrogating suppression with an IL-13 inhibitor while augmenting help with granulocyte/macrophage colony-stimulating factor and CD40L", Proc Natl Acad Sci USA, Oct. 1, 2002;99(20):13020-5.
Ahmed et al, Intratumoral expression of a fusogenic membrane glycoprotein enhances the efficacy of replicating adenovirus therapy, 10 Gene Therapy 1663-71 (2003).
Allison et al., "For Their Discovery of Cancer Therapy by Inhibition of Negative Immune in Physiology of Medicine Regulation"; The Nobel Assembly at Karolinska Institutet; 2018 Nobel Prize.
Altschul, S F et al (1990) J Mol Biol 215:403-10.
Altschul, S.F. (1993) J Mol Evol 36:290-300.
Annex A—WO 2017/118864—Figures 3 and 4 published Jul. 13, 2017.
Asada, Treatment of Human Cancer with Mumps Virus, 34(6) Cancer 1907-28 (Dec. 1974).
Assal et al: "Emerging targets in cancer immunotherapy: beyond CTLA-4 and PD-1", Immunotherapy. 2015;7(11):1169-86.
Balvay et al. Translational control of retroviruses, 5 Nature Reviews Microbiology 128-140 (Feb. 2007).
Bateman et al. Cancer Res. Mar. 1, 20005;60(6):1492-7.
Bateman et al. Cancer Res. Nov. 15, 2002;62(22):6566-78.
Bauzon and Hermiston, 2014. Front. Immunol., 5(74): 1-10.
Belsham and Sonenberg, RNA-protein interactions in regulation of picomavirus RNA translation, 60(3) Microbiological Reviews 499-511 (Sep. 1996).
Bett et al. Packaging capacity and stability of human adenovirus type 5 vectors, 67(10) J. Virol. 5911-21 (Oct. 1993).
BLAST analysis (publicly available through the National Centre for Biotechnology Information—http://www.ncbi.nlm.nih.gov/).
Blechacz et al. Engineered Measles Virus as a Novel Oncolytic Viral Therapy System for Hepatocellular Carcinoma, 44(6) Hepatology 1465-77 (Dec. 2006).
Brochu-Lafontaine and Lemay, Addition of exogenous polypeptides on the mammalian reovirus outer capsid using reverse genetics, 179 J. Virol. Methods 342-350 (2012).
Capece et al: "Targeting costimulatory molecules to improve antitumor immunity", J Biomed Biotechnol, 2012; 2012:926321.
Carson et al., "Oncolytic Herpe Simplex Virus 1 (HSV-1) Vectors: Increasing Treatment Efficacy and Range Throught Strategic Virus Design", Drugs Future. 2010,35(3): 183-195.

(56) References Cited

OTHER PUBLICATIONS

Carter et al. Identification of an overprinting gene in Merkel cell polyomavirus provides evolutionary insight into the birth of viral genes, 110(31) Proceedings of the National Academy of Sciences 12744-49 (Jul. 2013).

Cell Signaling Technology; Immune Checkpoint Signaling in the Tumor Microenvironment1; Mar. 2018.

Chen et al., "Dual silencing of Bcl-2 and Survivin by HSV-1 vector shows better antitumor efficacy in higher PKR phosphorylation tumor cells in vitro and in vivo", Cancer Gene Ther 22, 380-386; 2015.

Choi et al. Polymeric oncolytic adenovirus for cancer gene therapy, 219 Journal of Controlled Release 181-191 (2015).

Choi et al., "Concurrent delivery of GM-CSF and B7-1 using an oncolytic adenovirus elicits potent antitumor effect", Gene Therapy (2006) 13, 1010-1020 & 2006 Nature Publishing Group.

Choi et al., "Strengthening of antitumor immune memory and prevention of thymic atrophy mediated by adenovirus expressing IL-12 and GM-CSF", Gene Therapy (2012) 19, 711-723 & 2012 Macmillan Publishers.

Chou et al., "Mapping of Herpes Simplex Virus-1 Neurovirulence to ?134.5, a Gene Nonessential for Growth in Culture," Science, 1990, 250(4985):1262-1266.

Compilation of Virus Information from Swiss Institute of Bioinformatics retrieved on Nov. 3, 2021, available at https://viralzone.expasy.org/.

Croyle et al. PEGylation of a Vesicular Stomatitis Virus G Pseudotyped Lentivirus Vector Prevents Inactivation in Serum, 78(2) Journal of Virology 912-921 (Jan. 2004).

Danthinne and Imperiale, Production of first generation adenovirus vectors: a review, 7 Gene Therapy 1707-14 (2000).

Declaration of Dr. Sylvia D. Hall-Ellis dated Nov. 29, 2021 and Curriculum vitae.

Declaration of John C. Bell, Ph.D. dated Dec. 14, 2021 and Curriculum vitae.

Deguchi et al. Combination of the Tumor Angiogenesis Inhibitor Bevacizumab and Intratumoral Oncolytic Herpes Virus Injections as a Treatment Strategy for Human Gastric Cancers, 59(118) Hepatogastroenterology 1844-50 (Sep. 2012).

Devereux et al (1984) Nucleic Acids Research 12, p. 387-395.

Dias et al., 2012. Gene Ther., 19: 988-998.

Diefenbach et al., "Oncolytic virotherapy using herpes simplex virus: how far have we come?" Oncolytic Virotherapy, Nov. 1, 2015 (Nov. 1, 2015), p. 207.

Dikstein, The unexpected traits associated with core promoter elements, 2(5) Transcription 201-206 (Sep. 2011).

Documents filed on Jul. 9, 2018 in U.S. Appl. No. 16/068,830, including original application, preliminary amendment, application data sheet, search report, and transmittal form.

Donovan-Banfield et al. Deep splicing plasticity of the human adenovirus type 5 transcriptome drives virus evolution, 3 Communications Biology (2020) 124.

Du et al. "Tumor-specific oncolytic adenoviruses expressing granulocyte macrophage colony-stimulating factor or anti-CTLA4 antibody for the treatment of cancers", Cancer Gene Therapy, vol. 21, No. 8, Jul. 18, 2014 (Jul. 18, 2014), pp. 340-348.

Ebert et al. Syncytia Induction Enhances the Oncolytic Potential of Vesicular Stomatitis Virus in Virotherapy for Cancer, 64 Cancer Research 3265-3270 (May 2004).

Engeland et al. CTLA-4 and PD-L1 Checkpoint Blockade Enhances Oncolytic Measles Virus Therapy, 22(11) Molecular Therapy 1949-59 (Nov. 2014).

Excerpts from S. Baron (Ed.), Medical Microbiology, 4th. Ed. University of Texas Medical Branch at Galveston (1996).

Fransen et al., "Controlled Local Delivery of CTLA-4 Blocking Antibody Induces CD8+ T-Cell-Dependent Tumor Eradication and Decreaes Risk of Toxic Side Effects" Clin Cancer Res. 2013, 19(19):5381-9.

Fu et al. Expression of a Fusogenic Membrane Glycoprotein by an Oncolytic Herpes Simplex Virus Potentiates the Viral Antitumor Effect, 7(6) Molecular Therapy 748-754 (Jun. 2003).

Fukuhara et al. Triple Gene-Deleted Oncolytic Herpes Simplex Virus Vector Double-Armed with Interleukin 18 and Soluble B7-1 Constructed by Bacterial Artificial Chromosome-Mediated System, 65(23) Cancer Res. 10663-68 (Dec. 2005).

Gangi et al., "The safety of talimogene laherparepvec for the treatment of advanced melanoma", Expert Opinion on Drug Safety, Dec. 28, 2016 (Dec. 28, 2016), pp. 1-5.

Gao et al: "Recombinant vesicularm stomatitis virus targeted to Her2/neu combined with anti-CTLA4 antibody eliminates implanted mammary tumors", Cancer Gene Ther. Jan. 2009;16(1):44-52.

Gibney et al., "Preliminary results from a phase A study of INCB024360 combined with ipilimumab (ipi) in patients (pts) with melanoma." 2014 ASCO Annual Meeting, No. 3010.

Grandi, et al., Cancer Gene Therapy (2010) 17, 655-663 (Year: 2010).

Gri et al: "X40 ligand-transduced tumor cell vaccine synergizes with GM-CSF and requires CD40-Apc signaling to boost the host T cell antitumor response", J Immunol. Jan. 1, 2003;170(1):99-106.

Guedan et al. GALVexpression enhances the therapeutic efficacy of an oncolytic adenovirus by inducing cell fusion and enhancing virus distribution, 19 Gene Therapy 1048-57 (2012).

Gómez-Treviño et al. Effects of adenovirus-mediated SV5 fusogenic glycoprotein expression on tumor cells, 5 J. Gene Med. (2003) 483-492.

Haswell et al Eur J Immunol 2001 31 3094-3100.

Heinkoff and Heinkoff (1992) Proc. Natl. Acad. Sci. USA 89:10915-10919.

Herpesviridae Information from Virus Pathogen Resource (ViPR) retrieved on Nov. 4, 2021, available at: https://www.viprbrc.org/brc/aboutPathogen.spg7decoratoiHierpes.

Hetrologous Expression. In Binder, Hirokawa and Windorst (eds.)—Encyclopedia of Neuroscience. (2009) Springer, Berlin, Heidleberg Https://Doi.org/10.1007/978-3-540-29678-2_2190.

Hillier et al. Genomics in C. elegans: so many genes, such a little worm, 15 Genome Research 1651-60 (2005).

Ho et al. Unconventional viral gene expression mechanisms as therapeutic targets, 593 Nature 362-371 (May 2021).

Hoffmann et al. World J Gastroenterol. Jun. 14, 2007;13(22):3063-70.

Hoffmann et al. World J Gastroenterol. Mar. 28, 2008 14(12):1842-1850.

Hoggmann et al. W.J. G 2007, Jun. 14, 2013 (22), pp. 3063-30700.

Hooren et al., "Abstract B103: Intralesional administration of CTLA-4 blocking monoclonal antibodies as a means to optimize bladder cancer therapy", Cancer Immunol Res. 2016,4 (11_Supplement): B103.

Hooren et al., "Local checkpoint inhibition of CTLA-4 as a monotherapy or in combination with anti-PD1 prevents the growth of murine bladder cancer" Eur J Immunol. 2017,47(2):385-393.

Hu et al. "A simplified system for generating oncolytic adenovirus vector carrying one or two transgenes", Cancer Gene Therapy (2008) 15, 173-182 r 2008 Nature Publishing Group.

Huang et al., Mol Ther, Feb. 2010, vol. 18, No. 2, pp. 264-274.

Hurwitz et al: "CTLA-4 blockade synergizes with tumor-derived granulocyte-macrophage colony-stimulating factor for treatment of an experimental mammary carcinoma", Proc Natl Acad Sci USA, Aug. 18, 1998;95(17):10067-71.

IGI Global "What is Heterologous Expression" retrieved from https://www.igiglobal.com/dictionary/heterologousexpression/49470.

Inouye et al., "Codon optimization of genes for efficient protein expression in mammalian cells by selection of only preferred human codons", Protein Expression and Purification, 2015, 109:47-54.

International Search Report and Written Opinion issued in International Patent Application No. PCT/GB2017/050036, dated Apr. 26, 2017.

International Search Report and Written Opinion issued in International Patent Application No. PCT/GB2017/050037, dated Apr. 25, 2017.

(56) References Cited

OTHER PUBLICATIONS

International Search Report and Written Opinion issued in International Patent Application No. PCT/GB2017/050038, dated Apr. 24, 2017.
International Search Report for International Patent Application No. PCT/EP2015/066263, mailed from European Patent Office Oct. 7, 2015.
International Search Report for International Patent Application No. PCT/FI2009/051025, mailed from European Patent Office Mar. 24, 2010.
Ishihara et al. Systemic CD8+ T Cell-Mediated Tumoricidal Effects by Intratumoral Treatment of Oncolytic Herpes Simplex Virus with the Agonistic Monoclonal Antibody for Murine Glucocorticoid-Induced Tumor Necrosis Factor Receptor, 9(8) PLoS One e104669 (Aug. 2014).
Ishikawa et al. STING regulates intracellular DNA-mediated, type I interferon-dependent innate immunity, 461 Nature 788-792 (Oct. 8, 2009).
Jacobs et al. HSV-1 based vectors for gene therapy of neurological diseases and brain tumors Part II Vector Systems and Applications, 1(5) Neoplasia 402-416 (Nov. 1999).
Jacobs et al. Vaccinia Virus Vaccines: Past, Present and Future, 84(1) Antiviral Res. 1-13 (Oct. 2009).
John et al. Oncolytic Virus and Anti-4-IBB Combination Therapy Elicits Strong Antitumor Immunity against Established Cancer, 72(7) Cancer Research 1651-60 (Apr. 2012).
Kanagavelu et al PlosOne 2014, 9, 2, e90100.
Kanagavelu et al Vaccine 2012 30 691-701.
Karlin and Altschul (1993) Proc. Natl. Acad. Sci. USA 90:5873-5787.
Kasuya et al., Journal of Japan Surgical Society, 2006, 107, Extra Issue (2), p. 369, No. PS-005-8.
Kaufman et al: "Oncolytic viruses: a new class of immunotherapy drugs", Nat Rev Drug Discov, vol. 14, 642-662 (Sep. 2015).
Kaufmann et al. Chemovirotherapy of Malignant Melanoma with a Targeted and Armed Oncolytic Measles Virus, 133 Journal of Investigative Dermatology 1034-42 (2013).
Kelly and Russell, History of Oncolytic Viruses: Genesis to Genetic Engineering, 15(4) Molecular Therapy 651-659 (Apr. 2007).
Kim et al Cancer Res 2009, 69, 21, 8516-8525.
Kleinpeter et al. Vectorization in an oncolytic vaccinia virus of an antibody, a Fab and a scFv against programmed cell death-1 (PD-1) allows their intratumoral delivery and an improved tumor-growth inhibition, 5(10) Oncoimmunology e1220467 (2016).
Le Boeuf et al. Synergistic Interaction Between Oncolytic Viruses Augments Tumor Killing, 18(5) Molecular Therapy 888-895 (May 2010).
Lee et al. Enhanced Antitumor Effect of Oncolytic Adenovirus Expressing Interleukin-12 and B7-lin an Immunocompetent Murine Model, 12(19) Clin. Cancer Res. 5859-68 (Oct. 2006).
Lee et al: "Oncolytic potential of E1B 55 kDa-deleted YKL-1 recombinant adenovirus: correlation with p53 functional status" Int J Cancer (2000) 88: 454-463.
Li et al. Int. J. Cancer 2008, 123: 493-499.
Li, B et al: "Established B16 tumors are rejected following treatment with GM-CSF-secreting tumor cell immunotherapy in combination with anti-4-1 BB mAb", Clin Immunol. Oct. 2007;125(1):76-87.
Li, B et al: "Anti-programmed death-1 synergizes with granulocyte macrophage colony-stimulating factor-secreting tumor cell immunotherapy providing therapeutic benefit to mice with established tumors", Clin Cancer Res. Mar. 1, 2009;15(5):1623-34.
Lipson and Drake, Ipilimumab: An Anti-CTLA-4 Antibody for Metastatic Melanoma, 17(22) Clin. Cancer Res. 6958-62 (Nov. 2011).
List of known isolates within each virus family extracted from NCBI Taxonomy Browser Output of Ex. 1023, dtd Nov. 3, 2021.
Liu et al., "ICP34.5 deleted herpes simplex cirus with enhanced oncolytic, immune stimulating, and anti-tumour properties," Gene Therapy, 2003, 10(4):292-303.

Loskog, Angelica, "Immunostimulatory Gene Therapy Using Oncolytic Viruses as Vehicles," Viruses, 2015, 7:5780-5791.
Lundstrom, New frontiers in oncolytic viruses: optimizing and selecting for virus strains with improved efficacy, 12 Biologics: Targets and Therapy 43-60 (2018).
Ma et al. Oncolytic herpes simplex virus and immunotherapy, 19 BMC Immunology 40 (2018).
Maclean et al., "Herpes simplex cirus type 1 deletion variants 1714 and 1716 pinpoint neurovirulence-related sequences in Glasgow strain 17 + between immediate early gene 1 and the 'a' sequence," Journal of General Virology, 1991, 72:631-639.
EPO Opposition "Opponent's Response in opposition proceedings against Replimune's European Patent EP 3400291", provided by the European Patent Office on May 4, 2023.
Fonteneau et al., "Oncolytic immunotherapy: The new clinical outbreak", OncoImmunology, 2016, 5:1,e1066961.
Japanese Notice of Rejection mailed Feb. 28, 2023 during examination of related JP Patent Appl. No. 2019-537074.
Marcos et al., "Mapping of the RNA promoter of Newcastle disease virus", Virology, vol. 331, Issue 2, 2005, pp. 396-406.
Noton and Fearns, "Initiation and regulation of paramyxovirus transcription and replication", Virology, 2015, 479-480, 545- 554.
Alekseenko et al: "Therapeutic properties of a vector carrying the HSV thymidine kinase and GM-CSF genes and delivered as a complex with a cationic copolymer", Journal of Translational Medicine (2015) 13:78.
Amendment and Reply to Accompany Request for Continued Examination dated Sep. 26, 2018, U.S. Appl. No. 15/325,576, filed Jan. 11, 2017, 65 pages.
Amendment and Reply to Pursuant to 37 CFR §1.112 dated Aug. 26, 2019, U.S. Appl. No. 15/325,576, filed Jan. 11, 2017, 34 pages.
Applicant-Initiated Interview Summary dated Jan. 29, 2021 for U.S. Appl. No. 16/068,830, filed Jul. 9, 2018, 2 pages.
Bell, John C., Transcript of John C. Bell, Sep. 23, 2022, 87 pages.
Chiocca, E.A., Curriculum Vitae of E. Antonio Chiocca, M.D., Ph.D., Oct. 8, 2019, 92 pages.
Chiocca, E.A., Declaration of E. Antonio Chiocca, M.D., Ph.D., FAANS, Sep. 28, 2022, 35 pages.
Chiocca, E.A., Transcript of E. Antonio Chiocca, M.D., Ph.D., Nov. 30, 2022, 237 pages.
Correction of Notice of Allowability dated Feb. 1, 2021 for U.S. Appl. No. 16/068,830, filed Jul. 9, 2018, 2 pages.
Decision Granting Institution of Past-Grant Review dated Jun. 16, 2022, Paper 16, AIA Review No. PGR2022-00014, U.S. Pat. No. 10,947,513 issued Mar. 16, 2021, 27 pages.
Demonstrative Exhibits of Petitioners, AIA Review No. PGR2022-00014, U.S. Pat. No. 10,947,513 issued Mar. 16, 2021, Exhibit 1107, for Oral Argument Date Mar. 17, 2023, 56 pages.
Disclaimer in Patent Under 37 CFR 1.321(a) filed Mar. 15, 2022 for U.S. Pat. No. 10,947,513 issued Mar. 16, 2021, 6 pages.
Final Written Decision dated May 25, 2023, Paper 38, AIA Review No. PGR2022-00014, U.S. Pat. No. 10,947,513 issued Mar. 16, 2021, 61 pages.
Guo, Z.S. et al., "Rapid Generation of Multiple Loci-Engineered Marker-free Poxvirus and Characterization of a Clinical-Grade Oncolytic Vaccinia Virus", Molecular Therapy: Methods & Clinical Development, vol. 7, Dec. 2017, Pittsburgh, PA, USA, pp. 112-122.
Guse, K. et al., "Antiangiogenic Arming of an Oncolytic Vaccinia Virus Enhances Antitumor Efficacy in Renal Cell Cancer Models", Journal of Virology, 84(2), Jan. 2010, pp. 856-866.
Lun, X.Q. et al., "Efficacy of Systemically Administered Oncolytic Vaccinia Virotherapy for Malignant Gliomas Is Enhanced by Combination Therapy with Rapamycin or Cyclophosphamide", Clinical Cancer Research 15(8), 2009, pp. 2777-2788.
Patent Owner Response dated Sep. 28, 2022, AIA Review No. PGR2022-00014, U.S. Pat. No. 10,947,513 issued Mar. 16, 2021, 58 pages.
Patent Owner Sur Reply dated Feb. 1, 2023, AIA Review No. PGR2022-00014, U.S. Pat. No. 10,947,513 issued Mar. 16, 2021, 36 pages.
Patent Owner's Demonstrative Exhibits, AIA Review No. PGR2022-00014, U.S. Pat. No. 10,947,513 issued Mar. 16, 2021, Exhibit 2024, Replimune Limited, 75 pages.

(56) References Cited

OTHER PUBLICATIONS

Patent Owner's Objections to Petitioners Evidence dated Jul. 1, 2022, AIA Review No. PGR2022-00014, U.S. Pat. No. 10,947,513 issued Mar. 16, 2021, 33 pages.
Patent Owner's Preliminary Response dated Mar. 22, 2022, AIA Review No. PGR2022-00014, U.S. Pat. No. 10,947,513 issued Mar. 16, 2021, 41 pages.
Patent Owner's Supplemental Brief Regarding Xerox and Intel dated Mar. 31, 2023, AIA Review No. PGR2022-00014, U.S. Pat. No. 10,947,513 issued Mar. 16, 2021, 8 pages.
Petitioners Additional Briefing Regarding Xerox and Intel dated Mar. 31, 2023, AIA Review No. PGR2022-00014, U.S. Pat. No. 10,947,513 issued Mar. 16, 2021, 8 pages.
Petitioners' Reply to Owner's Response dated Dec. 20, 2022, AIA Review No. PGR2022-00014, U.S. Pat. No. 10,947,513 issued Mar. 16, 2021, 42 pages.
Petitioners' Reply to Patent Owner's Preliminary Response dated Apr. 14, 2022, AIA Review No. PGR2022-00014, U.S. Pat. No. 10,947,513 issued Mar. 16, 2021, 8 pages.
Record of Oral Hearing Held Mar. 17, 2023 dated May 22, 2023, Paper 37, AIA Review No. PGR2022-00014, U.S. Pat. No. 10,947,513 issued Mar. 16, 2021, 95 pages.
Reply under 37 CFR 1.111 dated Apr. 30, 2020, U.S. Appl. No. 16/068,830, filed Jan. 9, 2017, 11 pages.
Response to Rule 312 Communication and Applicant-Initiated Interview Summary dated Jan. 13, 2021 for U.S. Appl. No. 16/068,830, filed Jul. 9, 2018, 4 pages.
Rintoul, J.L., et al. "A Selectable and Excisable Marker System for the Rapid Creation of Recombinant Poxviruses", PloS one, 6(9), 2011, e24643, pp. 1-12.
Semmrich, M. et al., "Vectorized Treg-depleting aCTLA-4 elicits antigen cross- presentation and CD8+ T cell immunity to reject 'cold' tumors", Journal for ImmunoTheraphy of Cancer, 10(1), 2022, 36 pages.
Semmrich, M. et al., "Vectorized Treg-depleting αCTLA-4 elicits antigen cross-presentation and CD8+ T cell immunity to reject "cold" tumors", BioInvent International AB, Lund, Sweden, Transgene S.A., Illkirch-Graffenstaden, France, Abstract #746, 1 page.
Third Party Submissions Under 37 CFR §1.290 dated Jul. 30, 2019 for U.S. Appl. No. 16/068,830, filed Jul. 9, 2018, 2 pages.
Thomas, S. et al., "Development of a new fusion-enhanced oncolytic immunotherapy platform based on herpes simplex virus type 1", . Journal for Immuno Therapy of Cancer, 7:214, 2019, 17 pages.

Yamamoto, S., et al., "Imaging immediate-early and strict-late promoter activity during oncolytic herpes simplex virus type 1 infection and replication in tumors", Gene Therapy, 13, 2006, pp. 1731-1736.
Yang, S. et al., "Development of optimal bicistronic lentiviral vectors facilitates high-level TCR gene expression and robust tumor cell recognition", Gene Therapy, 15(21), Nov. 2008, 20 pages.
Thorne, "Next-Generation Oncolytic Vaccinia Vectors," In: Oncolytic Viruses: Methods and Protocols, edited by David H. Kirn et al., Humana Press, vol. 797, Chapter 14, pp. 205-215, 2012.
Dhar et al., "Syrian Hamster Tumor Model to Study Oncolytic ADS-Based Vectors," In: Oncolytic Viruses: Methods and Protocols, edited by David H. Kirn et al., Humana Press, vol. 797, Chapter 4, pp. 53-63, 2012.
Doronin et al., "Construction of Targeted and Armed Oncolytic Adenoviruses," In: Oncolytic Viruses: Methods and Protocols, edited by David H. Kirn et al., Humana Press, vol. 797, Chapter 3, pp. 35-52, 2012.
Fournier et al., "Analysis of Three Properties of Newcastle Disease Virus for Fighting Cancer: Tumor-Selective Replication, Antitumor Cytotoxicity, and Immunostimulation," In: Oncolytic Viruses: Methods and Protocols, edited by David H. Kirn et al., Humana Press, vol. 797, Chapter 13, pp. 177-204, 2012.
Gimenez-Alejandre et al., "Construction of Capsid-Modified Adenoviruses by Recombination in Yeast and Purification of Iodixanol-Gradient," In: Oncolytic Viruses: Methods and Protocols, edited by David H. Kirn et al., Humana Press, vol. 797, Chapter 2, pp. 21-34, 2012.
Goldufsky et al., "Oncolytic virus therapy for cancer," Oncolytic Virotherapy, 2:31-46, 2013.
Jeon et al. Journal of Virological Methods, 2022, vol. 299, pp. 1-7.
Rajiani et al. Molecular Therapy, published on May 2015, vol. 23, Supplement 1, S30.
Takara Bio, 2000 URL: https://www.takarabio.com/documentsNector%20Documents/PT3155-5.pdf; Accessed Apr. 20, 2022 (Year: 2000).
Shmulevitz et al., "Exploring Host Factors that Impact Reovirus Replication, Dissemination, and Reovirus-Induced Cell Death in Cancer Versus Normal Cells in Culture," In: Oncolytic Viruses: Methods and Protocols, edited by David H. Kirn et al., Humana Press, vol. 797, Chapter 12, pp. 163-176, 2012.
Stedman's Medical dictionary, 2000, lines 1-3 (Year: 2000).
Woller et al. "Viral infection of tumors overcomes resistance to PD-1-immunotherapy by broadening neoantigenome-directed T-cell responses", Molecular Therapy, vol. 23, No. 10, 1630-1640, 2015.

\* cited by examiner

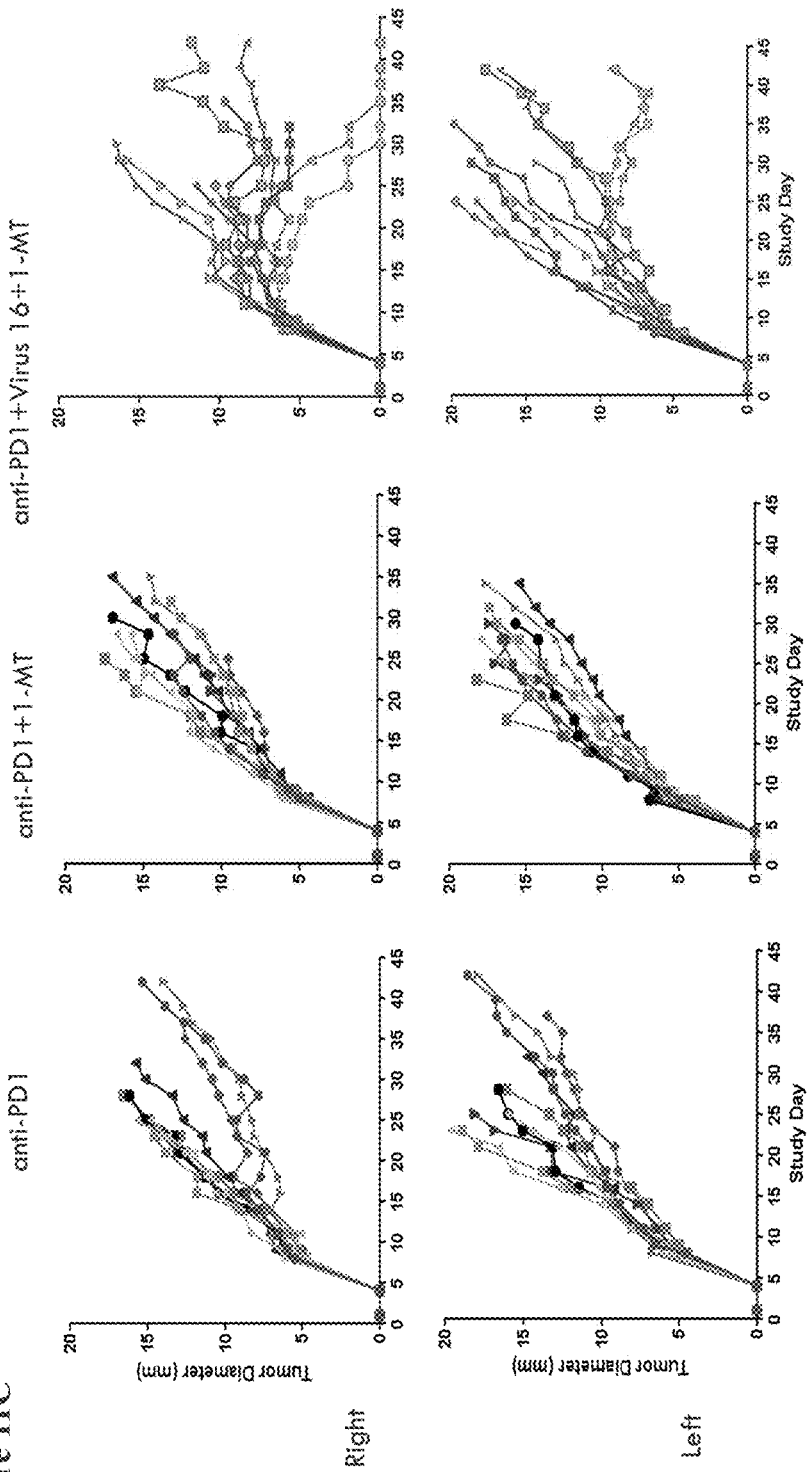

ENGINEERED VIRUS

CROSS-REFERENCE TO RELATED APPLICATIONS

This application is a continuation of U.S. Non-Provisional patent application Ser. No. 17/164,635 filed Feb. 1, 2021, which is a continuation of U.S. Non-Provisional patent application Ser. No. 16/068,830 filed Jul. 9, 2018, which is a national phase application under 35 U.S.C. § 371 to International Application No. PCT/GB2017/050038 filed Jan. 9, 2017, which claims the benefit of priority to Great Britain Patent Application Serial Nos. 1600380.8, 1600381.6 and 160382.4 all filed Jan. 8, 2016, all of which are incorporated herein by reference in their entirety.

INCORPORATION OF SEQUENCE LISTING

The instant application contains a Sequence Listing, named "SL_KEMPP0086USC2.XML" (78,944 bytes; created Jan. 31, 2023) which has been submitted electronically in ST.26 format and is hereby incorporated by reference in its entirety.

FIELD OF THE INVENTION

The invention relates to an oncolytic immunotherapeutic agent and to the use of the oncolytic immunotherapeutic agent in treating cancer.

BACKGROUND TO THE INVENTION

Viruses have a unique ability to enter cells at high efficiency. After entry into cells, viral genes are expressed and the virus replicates. This usually results in the death of the infected cell and the release of the antigenic components of the cell as the cell ruptures as it dies. As a result, virus mediated cell death tends to result in an immune response to these cellular components, including both those derived from the host cell and those encoded by or incorporated into the virus itself and enhanced due to the recognition by the host of so called damage associated molecular patterns (DAMPs) which aid in the activation of the immune response.

Viruses also engage with various mediators of the innate immune response as part of the host response to the recognition of a viral infection through e.g. toll-like receptors and cGAS/STING signalling and the recognition of pathogen associated molecular patterns (PAMPs) resulting in the activation of interferon responses and inflammation which are also immunogenic signals to the host. These immune responses may result in the immunogenic benefit to cancer patients such that immune responses to tumor antigens provide a systemic overall benefit resulting in the treatment of tumors which have not been infected with the virus, including micro-metastatic disease, and providing vaccination against relapse.

The combined direct ('oncolytic') effects of the virus, and immune responses against tumor antigens (including non-self 'neo-antigens', i.e. derived from the particular mutated genes in individual tumors) is termed 'oncolytic immunotherapy'.

Viruses may also be used as delivery vehicles ('vectors') to express heterologous genes inserted into the viral genome in infected cells. These properties make viruses useful for a variety of biotechnology and medical applications. For example, viruses expressing heterologous therapeutic genes may be used for gene therapy. In the context of oncolytic immunotherapy, delivered genes may include those encoding specific tumor antigens, genes intended to induce immune responses or increase the immunogenicity of antigens released following virus replication and cell death, genes intended to shape the immune response which is generated, genes to increase the general immune activation status of the tumor, or genes to increase the direct oncolytic properties (i.e. cytotoxic effects) of the virus. Importantly, viruses have the ability to deliver encoded molecules which are intended to help to initiate, enhance or shape the systemic anti-tumor immune response directly and selectively to tumors, which may have benefits of e.g. reduced toxicity or of focusing beneficial effects on tumors (including those not infected by the virus) rather than off-target effects on normal (i.e. non-cancerous) tissues as compared to the systemic administration of these same molecules or systemic administration of other molecules targeting the same pathways.

It has been demonstrated that a number of viruses including, for example, herpes simplex virus (HSV) have utility in the oncolytic treatment of cancer. HSV for use in the oncolytic treatment of cancer must be disabled such that it is no longer pathogenic, but can still enter into and kill tumor cells. A number of disabling mutations to HSV, including disruption of the genes encoding ICP34.5, ICP6, and/or thymidine kinase, have been identified which do not prevent the virus from replicating in culture or in tumor tissue in vivo, but which prevent significant replication in normal tissue. HSVs in which only the ICP34.5 genes have been disrupted replicate in many tumor cell types in vitro, and replicate selectively in tumor tissue, but not in surrounding tissue, in mouse tumor models. Clinical trials of ICP34.5 deleted, or ICP34.5 and ICP6 deleted, HSV have also shown safety and selective replication in tumor tissue in humans.

As discussed above, an oncolytic virus, including HSV, may also be used to deliver a therapeutic gene in the treatment of cancer. An ICP34.5 deleted virus of this type additionally deleted for ICP47 and encoding a heterologous gene for GM-CSF has also been tested in clinical trials, including a phase 3 trial in melanoma in which safety and efficacy in man was shown. GM-CSF is a pro-inflammatory cytokine which has multiple functions including the stimulation of monocytes to exit the circulation and migrate into tissue where they proliferate and mature into macrophages and dendritic cells. GM-CSF is important for the proliferation and maturation of antigen presenting cells, the activity of which is needed for the activation of an anti-tumor immune response. The trial data demonstrated that tumor responses could be seen in injected tumors, and to a lesser extent in uninjected tumors. Responses tended to be highly durable (months-years), and a survival benefit appeared to be achieved in responding patients. Each of these indicated engagement of the immune system in the treatment of cancer in addition to the direct oncolytic effect. However, this and other data with oncolytic viruses generally showed that not all tumors respond to treatment and not all patients achieve a survival advantage. Thus, improvements to the art of oncolytic therapy are clearly needed.

Recently it has been shown that oncolytic immunotherapy can result in additive or synergistic therapeutic effects in conjunction with immune checkpoint blockade (i.e. inhibition or 'antagonism' of immune checkpoint pathways, also termed immune co-inhibitory pathways). Checkpoint (immune inhibitory pathway) blockade is intended to block host immune inhibitory mechanisms which usually serve to prevent the occurrence of auto-immunity. However, in cancer patients these mechanisms can also serve to inhibit the induction of or block the potentially beneficial effects of any immune responses induced to tumors.

Systemic blockade of these pathways by agents targeting CTLA-4, PD-1 or PD-L1 have shown efficacy in a number of tumor types, including melanoma and lung cancer. However, unsurprisingly, based on the mechanism of action, off target toxicity can occur due to the induction of autoimmunity. Even so, these agents are sufficiently tolerable to provide considerable clinical utility. Other immune co-inhibitory pathway and related targets for which agents (mainly antibodies) are in development include LAG-3, TIM-3, VISTA, CSF1R, IDO, CEACAM1, CD47. Optimal clinical activity of these agents, for example PD1, PDL1, LAG-3, TIM-3, VISTA, CSF1R, IDO, CD47, CEACAM1, may require systemic administration or presence in all tumors due to the mechanism of action, i.e. including targeting of the interface of immune effector cells with tumors or other immune inhibitory mechanisms in/of tumors. In some cases, more localised presence in e.g. just some tumors or in some lymph nodes may also be optimally effective, for example agents targeting CTLA-4.

An alternative approach to increasing the anti-tumor immune response in cancer patients is to target (activate) immune co-stimulatory pathways, i.e. in contrast to inhibiting immune co-inhibitory pathways. These pathways send activating signals into T cells and other immune cells, usually resulting from the interaction of the relevant ligands on antigen presenting cells (APCs) and the relevant receptors on the surface of T cells and other immune cells. These signals, depending on the ligand/receptor, can result in the increased activation of T cells and/or APCs and/or NK cells and/or B cells, including particular subtypes, increased differentiation and proliferation of T cells and/or APCs and/or NK cells and/or B cells, including particular subtypes, or suppression of the activity of immune inhibitory T cells such as regulatory T cells. Activation of these pathways would therefore be expected to result in enhanced anti-tumor immune responses, but it might also be expected that systemic activation of these pathways, i.e. activation of immune responses generally rather than anti-tumor immune responses specifically or selectively, would result in considerable off target toxicity in non-tumor tissue, the degree of such off target toxicity depending on the particular immune co-stimulatory pathway being targeted. Nevertheless agents (mainly agonistic antibodies, or less frequently the soluble ligand to the receptor in question) targeting immune co-stimulatory pathways, including agents targeting GITR, 4-1-BB, OX40, CD40 or ICOS, and intended for systemic use (i.e. intravenous delivery) are in or have been proposed for clinical development.

For many of these approaches targeting immune co-inhibitory or co-inhibitory pathways to be successful, pre-existing immune responses to tumors are needed, i.e. so that a pre-existing immune response can be potentiated or a block to an anti-tumor immune response can be relieved. The presence of an inflamed tumor micro-environment, which is indicative of such an ongoing response, is also needed. Pre-existing immune responses to tumor neo-antigens appear to be particularly important for the activity of immune co-inhibitory pathway blockade and related drugs. Only some patients may have an ongoing immune response to tumor antigens including neoantigens and/or an inflamed tumor microenvironment, both of which are required for the optimal activity of these drugs. Therefore, oncolytic agents which can induce immune responses to tumor antigens, including neoantigens, and/or which can induce an inflamed tumor microenvironment are attractive for use in combination with immune co-inhibitory pathway blockade and immune potentiating drugs. This likely explains the promising combined anti-tumor effects of oncolytic agents and immune co-inhibitory pathway blockade in mice and humans that have so far been observed.

The above discussion demonstrates that there is still much scope for improving oncolytic agents and cancer therapies utilising oncolytic agents, anti-tumor immune responses and drugs which target immune co-inhibitory or co-stimulatory pathways.

SUMMARY OF THE INVENTION

The invention provides oncolytic viruses expressing GM-CSF and at least one molecule targeting an immune co-stimulatory pathway. GM-CSF aids in the induction of an inflammatory tumor micro-environment and stimulates the proliferation and maturation of antigen presenting cells, including dendritic cells, aiding the induction of an anti-tumor immune responses. These immune responses are amplified through activation of an immune co-stimulatory pathway or pathways using an immune co-stimulatory pathway activating molecule or molecules also delivered by the oncolytic virus.

The use of an oncolytic virus to deliver molecules targeting immune co-stimulatory pathways to tumors focuses the amplification of immune effects on anti-tumor immune responses, and reduces the amplification of immune responses to non-tumor antigens. Thus, immune cells in tumors and tumor draining lymph nodes are selectively engaged by the molecules activating immune co-stimulatory pathways rather than immune cells in general. This results in enhanced efficacy of immune co-stimulatory pathway activation and anti-tumor immune response amplification, and can also result in reduced off target toxicity. It is also important for focusing the effects of combined systemic immune co-inhibitory pathway blockade and immune co-stimulatory pathway activation on tumors, i.e. such that the amplified immune responses from which co-inhibitory blocks are released are antitumor immune responses rather than responses to non-tumor antigens.

The invention utilizes the fact that, when delivered by an oncolytic virus, the site of action of co-stimulatory pathway activation and of GM-CSF expression is in the tumor and/or tumor draining lymph node, but the results of such activation (an amplified systemic anti-tumor-immune response) are systemic. This targets tumors generally, and not only tumors to which the oncolytic virus has delivered the molecule or molecules targeting an immune co-stimulatory pathway or pathways and GM-CSF. Oncolytic viruses of the invention therefore provide improved treatment of cancer through the generation of improved tumor focused immune responses. The oncolytic virus of the invention also offers improved anti-tumor immune stimulating effects such that the immune-mediated effects on tumors which are not destroyed by oncolysis, including micro-metastatic disease, are enhanced, resulting in more effective destruction of these tumors, and more effective long term anti-tumor vaccination to prevent future relapse and improve overall survival.

Anti-tumor efficacy is improved when an oncolytic virus of the invention is used as a single agent and also when the virus is used in combination with other anti-cancer modalities, including chemotherapy, treatment with targeted agents, radiation and, in preferred embodiments, immune checkpoint blockade drugs (i.e. antagonists of an immune co-inhibitory pathway) and/or agonists of an immune co-stimulatory pathway.

Accordingly, the present invention provides an oncolytic virus comprising: (i) a GM-CSF-encoding gene; and (ii) an immune co-stimulatory pathway activating molecule or immune co-stimulatory pathway activating molecule-encoding gene. The virus may encode more than one immune co-stimulatory pathway activating molecule/gene.

The immune co-stimulatory pathway activating molecule is preferably GITRL, 4-1-BBL, OX40L, ICOSL or CD40L or a modified version of any thereof or a protein capable of blocking signaling through CTLA-4, for example an antibody which binds CTLA-4. Examples of modified versions include agonists of a co-stimulatory pathway that are secreted rather than being membrane bound, and/or agonists modified such that multimers of the protein are formed.

The virus may be a modified clinical isolate, such as a modified clinical isolate of a virus, wherein the clinical isolate kills two or more tumor cell lines more rapidly and/or at a lower dose in vino than one or more reference clinical isolates of the same species of virus.

The virus is preferably a herpes simplex virus (HSV), such as HSV1. The HSV typically does not express functional ICP34.5 and/or functional ICP47 and/or expresses the US11 gene as an immediate early gene.

The invention also provides:
- a pharmaceutical composition comprising a virus of the invention and a pharmaceutically acceptable carrier or diluent;
- the virus of the invention for use in a method of treating the human or animal body by therapy;
- the virus of the invention for use in a method of treating cancer, wherein the method optionally comprises administering a further anti-cancer agent;
- a product of manufacture comprising a virus of the invention in a sterile vial, ampoule or syringe;
- a method of treating cancer, which comprises administering a therapeutically effective amount of a virus or a pharmaceutical composition of the invention to a patient in need thereof, wherein the method optionally comprises administering a further anti-cancer agent which is optionally an antagonist of an immune co-inhibitory pathway, or an agonist of an immune co-stimulatory pathway;
- use of a virus of the invention in the manufacture of a medicament for use in a method of treating cancer, wherein the method optionally comprises administering a further anti-cancer agent which is optionally an antagonist of an immune co-inhibitory pathway, or an agonist of an immune co-stimulatory pathway;
- a method of treating cancer, which comprises administering a therapeutically effective amount of an oncolytic virus, an inhibitor of the indoleamine 2,3-dioxygenase (IDO) pathway and a further antagonist of an immune co-inhibitory pathway, or an agonist of an immune co-stimulatory pathway to a patient in need thereof.

BRIEF DESCRIPTION OF THE FIGURES

FIGS. 11A-11C shows the antitumor effects of Virus 16 in Balb/c mice harboring mouse CT26 tumors in the left and right flanks. Groups of 10 mice were then treated with: Vehicle (3 injections into right flank tumors every other day); 5×10exp6 pfu of Virus 16 (mRP1) injected in the right flank tumor every other day; anti-mouse PD1 alone (10 mg/kg i.p. every three days, BioXCell clone RMP1-14); anti-mouse CTLA-4 (3 mg/kg i.p every three days, BioXCell clone 9D9); anti-mouse PD1 together with Virus 16; anti-mouse CTLA4 together with Virus 16; 1-methyl trypotophan (I-MT; IDO inhibitor (5 mg/ml in drinking water)); anti-mouse PD1 together with 1-methyl trypotophan; or anti-mouse PD1 together with 1-methyl trypotophan and Virus 16. Effects on tumor size were observed for a further 30 days. Greater tumor reduction was seen in animals treated with combinations of virus and checkpoint blockade than with the single treatment groups. FIG. 11A shows that using Virus 16 and anti-PD1 in combination has a better anti-tumor effect than using either anti-PD1 or the virus alone. FIG. 11B shows that the anti-tumor effect of Virus 16 in combination with anti-CTLA-4 was better than the anti-tumor effect of either Virus 16 or anti-CTLA-4 alone. FIG. 11C shows that enhanced tumor reduction was observed using Virus 16 together with both anti-PD1 and IDO inhibition as compared to anti-PD1 and 1-MT inhibition in the absence of the virus.

BRIEF DESCRIPTION OF THE SEQUENCE LISTING

Figure 1:
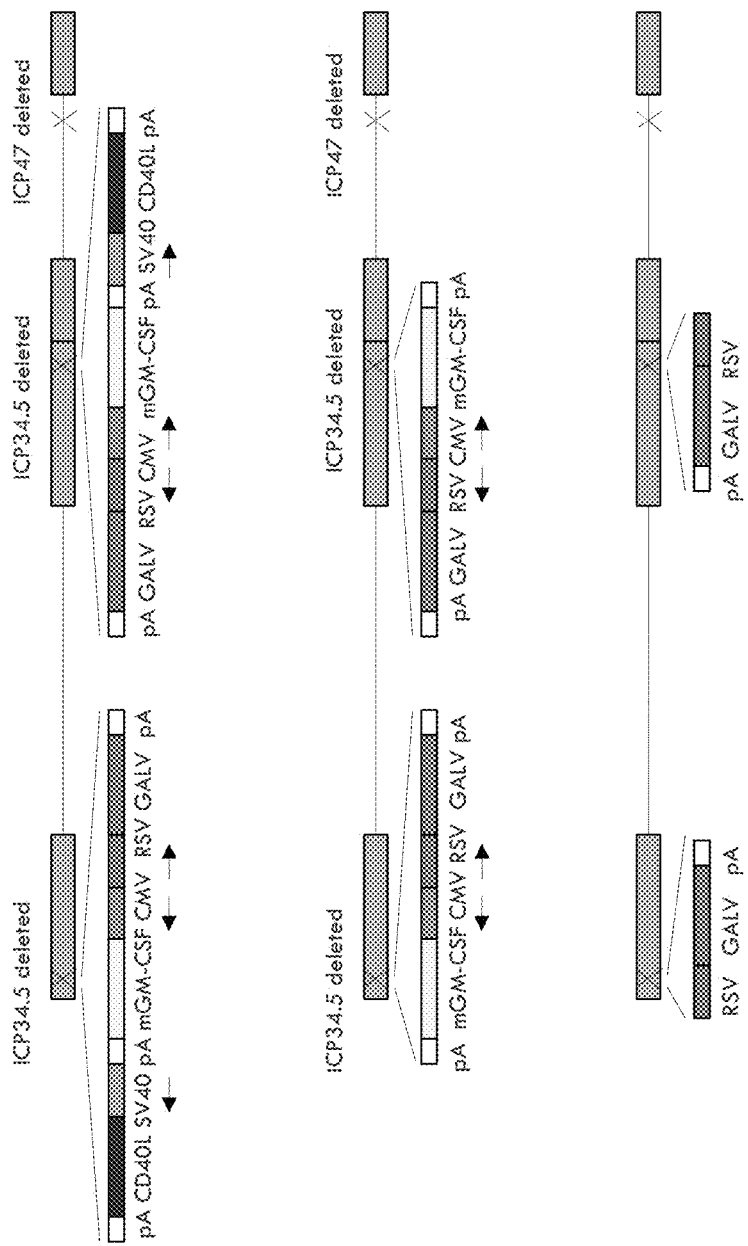
FIG. 1 depicts the structure of an exemplary virus of the invention that comprises a gene encoding GM-CSF and a gene encoding CD40L.

SEQ ID NO: 1 is the nucleotide sequence of mouse GM-CSF.
SEQ ID NO: 2 is the nucleotide sequence of a codon optimized version of mouse GM-CSF.
SEQ ID NO: 3 is the nucleotide sequence of human GM-CSF.
SEQ ID NO: 4 is the nucleotide sequence of a codon optimized version of human GM-CSF.
SEQ ID NO: 5 is the amino acid sequence of mouse GM-CSF.
SEQ ID NO: 6 is the amino acid sequence of human GM-CSF.
SEQ ID NO: 7 is the nucleotide sequence of GALV-R-.
SEQ ID NO: 8 is the nucleotide sequence of a codon optimized version of GALV-R- (the first three nucleotides are optional)
SEQ ID NO: 9 is the amino acid sequence of GALV-R-.
SEQ ID NO: 10 is the nucleotide sequence of a codon optimized version of a human membrane bound version of CD40L.
SEQ ID NO: 11 is the amino acid sequence of a human membrane bound version of CD40L.
SEQ ID NO: 12 is the nucleotide sequence of a codon optimized version of a multimeric secreted version of human CD40L.
SEQ ID NO: 13 is the amino acid sequence of a multimeric secreted version of human CD40L.
SEQ ID NO: 14 is the nucleotide sequence of a codon optimized version of a multimeric secreted version of mouse CD40L.
SEQ ID NO: 15 is the amino acid sequence of a multimeric secreted version of mouse CD40L.
SEQ ID NO: 16 is a codon optimized version of the nucleotide sequence of wild-type human CD40L.
SEQ ID NO: 17 is the amino acid sequence of wild-type human CD40L.
SEQ ID NO: 18 is a codon optimized version of the nucleotide sequence of wild-type mouse CD40L.
SEQ ID NO: 19 is the amino acid sequence of wild-type mouse CD40L.
SEQ ID NO: 20 is the nucleotide sequence of a codon optimized version of murine 4-1BBL.
SEQ ID NO: 21 is the nucleotide sequence of a codon optimized version of human 4-1BBL.
SEQ ID NO: 22 is the nucleotide sequence of a codon optimized version of secreted mouse 4-1BBL.
SEQ ID NO: 23 is the nucleotide sequence of a codon optimized version of human secreted 4-1BBL.
SEQ ID NO: 24 is the nucleotide sequence of a codon optimized version of murine GITRL.
SEQ ID NO: 25 is the nucleotide sequence of a codon optimized version of human GITRL.
SEQ ID NO: 26 is the nucleotide sequence of a codon optimized version of secreted murine GITRL.
SEQ ID NO: 27 is the nucleotide sequence of a codon optimized version of secreted human GITRL.
SEQ ID NO: 28 is the nucleotide sequence of a codon optimized version of murine OX40L.
SEQ ID NO: 29 is the nucleotide sequence of a codon optimized version of human OX40L.
SEQ ID NO: 30 is the nucleotide sequence of a codon optimized version of secreted murine OX40L.
SEQ ID NO: 31 is the nucleotide sequence of a codon optimized version of secreted human OX40L.
SEQ ID NO: 32 is the nucleotide sequence of a codon optimized version of murine ICOSL.
SEQ ID NO: 33 is the nucleotide sequence of a codon optimized version of human ICOSL.
SEQ ID NO: 34 is the nucleotide sequence of a murine scFv CTLA-4 antibody. The first six and last eight nucleotides are restriction sites added for cloning purposes.
SEQ ID NO: 35 is the nucleotide sequence of a murine scFv CTLA-4 antibody. The first six and last eight nucleotides are restriction sites added for cloning purposes.
SEQ ID NO: 36 is the nucleotide sequence of the CMV promoter.

SEQ ID NO: 37 is the nucleotide sequence of the RSV promoter.

SEQ ID NO: 38 is the nucleotide sequence of BGH polyA.

SEQ ID NO: 39 is the nucleotide sequence of SV40 late polyA.

SEQ ID NO: 40 is the nucleotide sequence of the SV40 enhancer promoter.

SEQ ID NO: 41 is the nucleotide sequence of rabbit beta-globulin (RBG) polyA.

SEQ ID NO: 42 is the nucleotide sequence of GFP.

SEQ ID NO: 43 is the nucleotide sequence of the MoMuLV LTR promoter.

SEQ ID NO: 44 is the nucleotide sequence of the EF1a promoter.

SEQ ID NO: 45 is the nucleotide sequence of HGH polyA.

DETAILED DESCRIPTION OF THE INVENTION

Oncolytic Virus

The virus of the invention is oncolytic. An oncolytic virus is a virus that infects and replicates in tumor cells, such that the tumor cells are killed. Therefore, the virus of the invention is replication competent. Preferably, the virus is selectively replication competent in tumor tissue. A virus is selectively replication competent in tumor tissue if it replicates more effectively in tumor tissue than in non-tumor tissue. The ability of a virus to replicate in different tissue types can be determined using standard techniques in the art.

The virus of the invention may be any virus which has these properties, including a herpes virus, pox virus, adenovirus, retrovirus, rhabdovirus, paramyxovirus or reovirus, or any species or strain within these larger groups. Viruses of the invention may be wild type (i.e. unaltered from the parental virus species), or with gene disruptions or gene additions. Which of these is the case will depend on the virus species to be used. Preferably the virus is a species of herpes virus, more preferably a strain of HSV, including strains of HSV1 and HSV2, and is most preferably a strain of HSV1. In particularly preferred embodiments the virus of the invention is based on a clinical isolate of the virus species to be used. The clinical isolate may have been selected on the basis of it having particular advantageous properties for the treatment of cancer.

The clinical isolate may have surprisingly good anti-tumor effects compared to other strains of the same virus isolated from other patients, wherein a patient is an individual harbouring the virus species to be tested. The virus strains used for comparison to identify viruses of the invention may be isolated from a patient or an otherwise healthy (i.e. other than harboring the virus species to be tested) volunteer, preferably an otherwise healthy volunteer. HSV1 strains used to identify a virus of the invention are typically isolated from cold sores of individuals harboring HSV1, typically by taking a swab using e.g. Virocult (Sigma) brand swab/container containing transport media followed by transport to the facility to be used for further testing.

After isolation of viruses to be compared from individuals, stocks of the viruses are typically prepared, for example by growing the isolated viruses on BHK or vero cells. Preferably, this is done following no more than 3 cycles of freeze thaw between taking the sample and it being grown on, for example, BHK or vero cells to prepare the virus stock for further use. More preferably the virus sample has undergone 2 or less than 2 cycles of freeze thaw prior to preparation of the stock for further use, more preferably one cycle of freeze thaw, most preferably no cycles of freeze thaw. Lysates from the cell lines infected with the viruses prepared in this way after isolation are compared, typically by testing for the ability of the virus to kill tumor cell lines in vitro. Alternatively, the viral stocks may be stored under suitable conditions, for example by freezing, prior to testing. Viruses of the invention have surprisingly good anti-tumor effects compared to other strains of the same virus isolated from other individuals, preferably when compared to those isolated from >5 individuals, more preferably >10 other individuals, most preferably >20 other individuals.

The stocks of the clinical isolates identified for modification to produce viruses of the invention (i.e. having surprisingly good properties for the killing of tumor cells as compared to other viral strains to which they were compared) may be stored under suitable conditions, before or after modification, and used to generate further stocks as appropriate.

A clinical isolate is a strain of a virus species which has been isolated from its natural host. The clinical isolate has preferably been isolated for the purposes of testing and comparing the clinical isolate with other clinical isolates of that virus species for a desired property, in the case of viruses of the invention that being the ability to kill human tumor cells. Clinical isolates which may be used for comparison also include those from clinical samples present in clinical repositories, i.e. previously collected for clinical diagnostic or other purposes. In either case the clinical isolates used for comparison and identification of viruses of the invention will preferably have undergone minimal culture in vitro prior to being tested for the desired property, preferably having only undergone sufficient culture to enable generation of sufficient stocks for comparative testing purposes. As such, the viruses used for comparison to identify viruses of the invention may also include deposited strains, wherein the deposited strain has been isolated from a patient, preferably an HSV1 strain isolated from the cold sore of a patient.

The virus may be a modified clinical isolate, wherein the clinical isolate kills two or more tumor cell lines more rapidly and/or at a lower dose in vitro than one or more reference clinical isolate of the same species of virus. Typically, the clinical isolate will kill two or more tumor cell lines within 72 hours, preferably within 48 hours, more preferably within 24 hours, of infection at multiplicities of infection (MOI) of less than or equal to 0.1, preferably less than or equal to an MOI of 0.01, more preferably less than or equal to an MOI of 0.001. Preferably the clinical isolate will kill a broad range of tumor cell lines, such as 2, 3, 4, 5, 6, 7, 8, 9, 10 or, for example, all of the following human tumor cell lines: U87MG (glioma), HT29 (colorectal), LNCaP (prostate), MDA-MB-231 (breast), SK-MEL-28 (melanoma), Fadu (squamous cell carcinoma), MCF7 (breast), A549 (lung), MIAPACA-2 (pancreas), CAPAN-1 (pancreas), HT1080 (fibrosarcoma).

Thus, the virus of the invention may be capable of killing cells from two or more, such as 3, 4, 5, 6, 7 or more, different types of tumor such as two or more, such as 3, 4, 5, 6, 7 or more, solid tumors, including but not limited to colorectal tumor cells, prostate tumor cells, breast tumor cells, ovarian tumor cells, melanoma cells, squamous cell carcinoma cells, lung tumor cells, pancreatic tumor cells, sarcoma cells and/or fibrosarcoma cells.

Tumor cell line killing can be determined by any suitable method. Typically, a sample is first isolated from a patient, preferably, in the case of HSV1, from a cold sore, is used to infect BHK cells, or another suitable cell line such as vero cells. Positive samples are typically identified by the presence of a cytopathic effect (CPE) 24-72 hours post infection, such as 48 hours post infection, and confirmed to be the target viral species by, for example, immunohistochemistry or PCR. Viral stocks are then generated from the positive samples. A sample from the viral stock is typically tested and compared to other samples generated in the same way using swabs from different patients. Testing may be carried out by determining the level of CPE achieved at a range of multiplicity of infection (MOI) and at various times post infection.

For example, cell lines at 80% confluency may be infected with the viral sample at MOI of 1, 0.1, 0.01 and 0.001 and duplicate plates incubated for 24 and 48 hours at 37° C., 5% $CO_2$ prior to determination of the extent of viral cell killing. This may be determined by, for example, fixing the cells with glutaraldehyde and staining with crystal violet using standard methods. The level of cell lysis may then be assessed by standard methods such as gross observation, microscopy (cell counts) and photography. The method may be repeated with the cells being incubated for shorter time periods, such as 8, 12 or 16 hours, or longer time periods, such as 72 hours, before cell killing is determined, or at additional MOIs such as 0.0001 or less.

Growth curve experiments may also be conducted to assess the abilities of different clinical isolates to replicate in tumor cell lines in vitro. For example, cell lines at 80% confluency may be infected with the viral sample at MOI of 1, 0.1, 0.01 and 0.001 are incubated at 37° C., 5% $CO_2$ and the cells lysed, typically by freeze/thawing, at 0, 8, 16, 24 and 48 hours post infection prior to determination of the extent of viral cell killing. This may be determined by, for example, assessing viral titres by a standard plaque assay.

A clinical isolate of the invention can kill infected tumor cell lines more rapidly and/or at a lower MOI than the other clinical isolates to which it is compared, preferably 2, 3, 4, 5 or 10 or more, other clinical isolates of the same virus species. The clinical isolate of the invention typically kills a 10%, 25% or 50% greater proportion of the tumor cells present at a particular MOI and time point than at least one, preferably 2, 3, 4, 5 or 10 or more, other clinical isolates of the same virus type at the same MOI and time point to which it was compared. The clinical isolate of the invention typically kills the same or a greater proportion of tumor cells at a MOI that is half or less than half that of the MOI at which one or more, preferably 2, 3, 4, 5, 10 or 15 or more, other clinical isolates of the same virus species used for the comparison at the same time point, typically at 12, 24 and/or 48 hours, kills the same proportion of tumor cells. Preferably, a clinical isolate of the invention typically kills the same or a greater proportion of tumor cells at a MOI that is 5 or 10 times lower than the MOI at which one or more, preferably 2, 3, 4, 5, 10 or 15 or more, other clinical isolates of the same virus used for the comparison at the same time point, typically at 12, 24 and/or 48 hours kills the same proportion of tumor cells. The improved tumor cell killing abilities of a virus of the invention are typically achieved compared to at least 50%, 75% or 90% of the other clinical isolates of the same viral species used for the comparison. The virus is preferably compared to at least 4 other virus strains, such as, for example, 7, 9, 19, 39 or 49 other virus strains of the same species.

The isolated strains may be tested in batches, for example of 4-8 viral strains at a time, on, for example, 4-8 of the tumor cell lines at a time. For each batch of experiments, the degree of killing achieved is ranked on each cell line for the best (i.e. least surviving cells at each time point/MOI) to the worst (i.e. most surviving cells for each time point/MOI) for the viruses being compared in that experiment. The virus strains from each experiment which perform the best across the range of tumor cell line tested (i.e. that consistently ranked as one of the best at killing the cell lines) may then be compared head to head in further experiments using other clinical isolates and/ore other tumor cell lines to identify the best virus strains in the total of, for example, >20 virus strains sampled. Those ranked as the best overall are the viruses of the invention.

In a preferred embodiment, the virus of the invention is a strain selected from:

- strain RH018A having the provisional accession number ECCAC 16121904;
- strain RH004A having the provisional accession number ECCAC 16121902:
- strain RH031A having the provisional accession number ECCAC 16121907;
- strain RH040B having the provisional accession number ECCAC 16121908;
- strain RH015A having the provisional accession number ECCAC 16121903;
- strain RH021A having the provisional accession number ECCAC 16121905;
- strain RH023A having the provisional accession number ECCAC 16121906; and
- strain RH047A having the provisional accession number ECCAC 16121909.

More preferably, the virus of the invention is a strain selected from:

- strain RH018A having the provisional accession number ECCAC 16121904;
- strain RH004A having the provisional accession number ECCAC 16121902;
- strain RH031A having the provisional accession number ECCAC 16121907;
- strain RH040B having the provisional accession number ECCAC 16121908; and
- strain RH015A having the provisional accession number ECCAC 16121903;

Most preferably, the virus of the invention is strain RH018A having the accession number EACC 16121904.

An HSV of the invention is capable of replicating selectively in tumors, such as human tumors. Typically, the HSV replicates efficiently in target tumors but does not replicate efficiently in non-tumor tissue. This HSV may comprise one or more mutations in one or more viral genes that inhibit replication in normal tissue but still allow replication in tumors. The mutation may, for example, be a mutation that prevents the expression of functional ICP34.5, ICP6 and/or thymidine kinase by the HSV.

In one preferred embodiment, the ICP34.5-encoding genes are mutated to confer selective oncolytic activity on the HSV. Mutations of the ICP34.5-encoding genes that prevent the expression of functional ICP34.5 are described in Chou et al. (1990) Science 250:1262-1266, Maclean et al. (1991) J. Gen. Virol. 72:631-639 and Liu et al. (2003) Gene Therapy 10:292-303, which are incorporated herein by reference. The ICP6-encoding gene and/or thymidine kinase-encoding gene may also be inactivated, as may other genes provided that such inactivation does not prevent the virus infecting or replicating in tumors.

The HSV may contain a further mutation or mutations which enhance replication of the HSV in tumors. The resulting enhancement of viral replication in tumors not only results in improved direct 'oncolytic' tumor cell killing by the virus, but also enhances the level of heterologous (i.e. a gene inserted into the virus, in the case of viruses of the invention genes encoding GM-CSF and an immune co-stimulatory pathway activating molecule(s)) gene expression and increases the amount of tumor antigen released as tumor cells die, both of which may also improve the immunogenic properties of the therapy for the treatment of cancer. For example, in a preferred embodiment of the invention, deletion of the ICP47-encoding gene in a manner that places the US11 gene under the control of the immediate early promoter that normally controls expression of the ICP47 encoding gene leads to enhanced replication in tumors (see Liu et al., 2003, which is incorporated herein by reference).

Other mutations that place the US11 coding sequence, which is an HSV late gene, under the control of a promoter that is not dependent on viral replication may also be introduced into a virus of the invention. Such mutations allow expression of US11 before HSV replication occurs and enhance viral replication in tumors. In particular, such mutations enhance replication of an HSV lacking functional ICP34.5-encoding genes.

Accordingly, in one embodiment the HSV of the invention comprises a US11 gene operably linked to a promoter, wherein the activity of the promoter is not dependent on viral replication. The promoter may be an immediate early (IE) promoter or a non-HSV promoter which is active in mammalian, preferably human, tumor cells. The promoter may, for example, be a eukaryotic promoter, such as a promoter derived from the genome of a mammal, preferably a human. The promoter may be a ubiquitous promoter (such as a promoter of β-actin or tubulin) or a cell-specific promoter, such as tumor-specific promoter. The promoter may be a viral promoter, such as the Moloney murine leukaemia virus long terminal repeat (MMLV LTR) promoter or the human or mouse cytomegalovirus (CMV) IE promoter. HSV immediate early (IE) promoters are well known in the art. The HSV IE promoter may be the promoter driving expression of ICP0, ICP4, ICP22, ICP27 or ICP47.

The genes referred to above the functional inactivation of which provides the property of tumor selectivity to the virus may be rendered functionally inactive by any suitable method, for example by deletion or substitution of all or part of the gene and/or control sequence of the gene or by insertion of one or more nucleic acids into or in place of the gene and/or the control sequence of the gene. For example, homologous recombination methods, which are standard in the art, may be used to generate the virus of the invention. Alternatively bacterial artificial chromosome (BAC)-based approaches may be used.

As used herein, the term "gene" is intended to mean the nucleotide sequence encoding a protein, i.e. the coding sequence of the gene. The various genes referred to above may be rendered non-functional by mutating the gene itself or the control sequences flanking the gene, for example the promoter sequence. Deletions may remove one or more portions of the gene, the entire gene or the entire gene and all or some of the control sequences. For example, deletion of only one nucleotide within the gene may be made, resulting in a frame shift. However, a larger deletion may be made, for example at least about 25%, more preferably at least about 50% of the total coding and/or non-coding sequence. In one preferred embodiment, the gene being rendered functionally inactive is deleted. For example, the entire gene and optionally some of the flanking sequences may be removed from the virus. Where two or more copies of the gene are present in the viral genome both copies of the gene are rendered functionally inactive.

A gene may be inactivated by substituting other sequences, for example by substituting all or part of the endogenous gene with a heterologous gene and optionally a promoter sequence. Where no promoter sequence is substituted, the heterologous gene may be inserted such that it is controlled by the promoter of the gene being rendered non-functional. In an HSV of the invention it is preferred that the ICP34.5 encoding-genes are rendered non-functional by the insertion of a heterologous gene or genes and a promoter sequence or sequences operably linked thereto, and optionally other regulatory elements such as polyadenylation sequences, into each the ICP34.5-encoding gene loci.

A virus of the invention is used to express GM-CSF and an immune co-stimulatory pathway activating molecule in tumors. This is typically achieved by inserting a heterologous gene encoding GM-CSF and a heterologous gene encoding the immune co-stimulatory pathway activating molecule in the genome of a selectively replication competent virus wherein each gene is under the control of a promoter sequence. As replication of such a virus will occur selectively in tumor tissue, expression of the GM-CSF and the immune co-stimulatory activating protein by the virus is also enhanced in tumor tissue as compared to non-tumor tissue in the body. Enhanced expression occurs where expression is greater in tumors as compared to other tissues of the body. Proteins expressed by the oncolytic virus would also be expected to be present in oncolytic virus-infected tumor draining lymph nodes, including due to trafficking of expressed protein and of virus in and on antigen presenting cells from the tumor. Accordingly, the invention provides benefits of expression of both GM-CSF and an immune co-stimulatory pathway activating molecule selectively in tumors and tumor draining lymph nodes combined with the anti-tumor effect provided by oncolytic virus replication.

The virus of the invention comprises GM-CSF. The sequence of the gene encoding GM-CSF may be codon optimized so as to increase expression levels of the respective proteins in target cells as compared to if the unaltered sequence is used.

The virus of the invention comprises one or more immune co-stimulatory pathway activating molecules and/or one or more genes encoding an immune co-stimulatory pathway activating molecule. Immune co-stimulatory pathway activating molecules include proteins and nucleic acid molecules (e.g. aptamer sequences). Examples of immune co-stimulatory pathway activating molecules include CD40 ligand, GITR ligand, 4-1-BB ligand, OX40 ligand, ICOS ligand, flt3 ligand, TL1A, CD30 ligand, CD70 and single chain antibodies targeting the respective receptors for these molecules (CD40, GITR, 4-1-BB, OX40, ICOS, flt3, DR3, CD30, CD27). The CD40L, GITRL, 4-1-BBL, OX40L, ICOSL, flt3L, TL1A, CD30L or CD70L may be a modified version of any thereof, such as a soluble version.

Activators of immune co-stimulatory pathways include mutant or wild type, soluble, secreted and/or membrane bound ligands, and agonistic antibodies including single chain antibodies. Viruses of the invention preferably encode one or more of CD40L, ICOSL, 4-1-BBL, GITRL or OX40L.

The inhibitor of a co-inhibitory pathway may be a CTLA-4 inhibitor. The CTLA-4 inhibitor is typically a molecule such as a peptide or protein that binds to CTLA-4 and reduces or blocks signaling through CTLA-4, such as by reducing activation by B7. By reducing CTLA-4 signalling, the inhibitor reduces or removes the block of immune stimulatory pathways by CTLA-4.

The CTLA-4 inhibitor is preferably an antibody or an antigen binding fragment thereof. The term "antibody" as referred to herein includes whole antibodies and any antigen binding fragment (i.e., "antigen-binding portion") or single chains thereof. An antibody refers to a glycoprotein comprising at least two heavy (H) chains and two light (kappa) (L) chains inter-connected by disulfide bonds, or an antigen binding portion thereof. Each heavy chain is comprised of a heavy chain variable region (abbreviated herein as VH) and a heavy chain constant region. Each light chain is comprised of a light chain variable region (abbreviated herein as VL) and a light chain constant region. The variable regions of the heavy and light chains contain a binding domain that interacts with an antigen. The VH and VL regions can be further subdivided into regions of hypervariability, termed complementarity determining regions (CDR), interspersed with regions that are more conserved, termed framework regions (FR). The constant regions of the antibodies may mediate the binding of the immunoglobulin to host tissues or factors, including various cells of the immune system (e.g., effector cells) and the first component (Clq) of the classical complement system.

The antibody is typically a monoclonal antibody. The antibody may be a chimeric antibody. The antibody is preferably a humanised antibody and is more preferably a human antibody.

The term "antigen-binding fragment" of an antibody refers to one or more fragments of an antibody that retain the ability to specifically bind to CTLA-4. The antigen-binding fragment also retains the ability to inhibit CTLA-4 and hence to reduce or remove the CTLA-4 blockade of a stimulatory immune response. Examples of suitable fragments include a Fab fragment, a F(ab')$_2$ fragment, a Fab' fragment, a Fd fragment, a Fv fragment, a dAb fragment and an isolated complementarity determining region (CDR). Single chain antibodies such as scFv and heavy chain antibodies such as VHH and camel antibodies are also intended to be encompassed within the term "antigen-binding portion" of an antibody. In a preferred embodiment, the antibody is an scFv. Examples of suitable scFv molecules are disclosed in, for example, WO2007/123737 and WO2014/066532, which are incorporated herein by reference. The scFv may be encoded by the nucleotide sequence shown in SEQ ID NO: 34 the nucleotide sequence shown in SEQ ID NO: 35.

Viruses of the invention may encode one or more immune co-stimulatory pathway activating molecules, preferably 1, 2, 3 or 4 immune co-stimulatory pathway activating molecules, more preferably 1 or 2 immune co-stimulatory pathway activating molecules.

For example, the virus may comprise genes encoding:
CD40L and one or more of ICOSL, 4-1-BBL, GITRL, OX40L and a CTLA-4 inhibitor;
ICOSL and one or more of CD40L, 4-1-BBL, GITRL, OX40L and a CTLA-4 inhibitor;
4-1-BBL and one or more of CD40L, ICOSL, GITRL, OX40L and a CTLA-4 inhibitor;
GITRL and one or more of CD40L, ICOSL, 4-1-BBL, OX40L and a CTLA-4 inhibitor;
OX40L and one or more of CD40L, ICOSL, 4-1-BBL, GITRL and a CTLA-4 inhibitor;
a CTLA-4 inhibitor and one or more of CD40L, ICOSL, 4-1-BBL, GITRL and OX40L.

The sequence of the gene encoding the immune co-stimulatory activating molecule may be codon optimized so as to increase expression levels of the respective protein(s) in target cells as compared to if the unaltered sequence is used.

The virus of the invention may comprise one or more further heterologous genes in addition to GM-CSF and an immune co-stimulatory pathway activating molecule, including, in a preferred embodiment, a fusogenic protein such as GALVR-.

The fusogenic protein may be any heterologous protein capable of promoting fusion of a cell infected with the virus of the invention to another cell. A fusogenic protein, preferably a wild type or modified viral glycoprotein (i.e. modified to increase its fusogenic properties), is a protein which is capable in inducing the cell to cell fusion (syncitia formation) of cells in which it is expressed. Examples of fusogenic glycoproteins include VSV-G, syncitin-1 (from human endogenous retrovirus-W (HERV-W)) or syncitin-2 (from HERVFRDE1), paramyxovirus SV5-F, measles virus-H, measles virus-F, RSV-F, the glycoprotein from a retrovirus or lentivirus, such as gibbon ape leukemia virus (GALV), murine leukemia virus (MLV), Mason-Pfizer monkey virus (MPMV) and equine infectious anemia virus (EIAV) with the R transmembrane peptide removed (R-versions). In a preferred embodiment the fusogenic protein is from GALV and has the R- peptide removed (GALV-R-).

The virus of the invention may optionally comprise multiple copies of the fusogenic protein-encoding gene, preferably 1 or 2 copies. The virus may comprise two or more different fusogenic proteins, including any of the fusogenic proteins listed above.

The fusogenic protein or proteins optionally expressed by a virus of the invention may be identical to a naturally occurring protein, or may be a modified protein.

The fusogenic protein-encoding gene (fusogenic gene) may have a naturally occurring nucleic acid sequence or a modified sequence. The sequence of the fusogenic gene may, for example, be modified to increase the fusogenic properties of the encoded protein, or to provide codon optimisation and therefore increase the efficiency of expression of the encoded protein.

The invention also provides a virus, such as a pox virus or a HSV, preferably HSV1, which expresses at least three heterologous genes, wherein each of the three heterologous genes is driven by a different promoter selected from the CMV promoter, the RSV promoter, the EF1a promoter, the SV40 promoter and a retroviral LTR promoter. The virus may, for example, express four heterologous genes, wherein each of the four heterologous genes is driven by a different promoter selected from the CMV promoter, the RSV promoter, the EF1a promoter, the SV40 promoter and a retroviral LTR promoter. The retroviral LTR is preferably from MMLV (SEQ ID NO:43), also known as MoMuLV. The heterologous genes may be terminated by poly adenylation sequences. The poly adenylation sequences may be the same or different. Preferably each heterologous gene is terminated by a different poly adenylation sequence, which is preferably selected from the BGH, SV40, HGH and RBG poly adenylation sequences.

The invention also provides a virus, such as a pox virus or a HSV, preferably HSV1, which expresses at least three heterologous genes, wherein each of the three heterologous genes is terminated by a different poly adenylation sequence selected from the BGH, SV40, HGH and RBG poly adenylation sequences. The virus may, for example, express four heterologous genes terminated by each of the BGH, SV40, HGH and RBG poly adenylation sequences, respectively.

Production of Virus

Viruses of the invention are constructed using methods well known in the art. For example plasmids (for smaller viruses and single and multiple genome component RNA viruses) or BACs (for larger DNA viruses including herpes viruses) encoding the viral genome to be packaged, including the genes encoding the fusogenic and immune stimulating molecules under appropriate regulatory control, can be constructed by standard molecular biology techniques and transfected into permissive cells from which recombinant viruses can be recovered.

Alternatively, in a preferred embodiment plasmids containing DNA regions flanking the intended site of insertion can be constructed, and then co-transfected into permissive cells with viral genomic DNA such that homologous recombination between the target insertion site flanking regions in the plasmid and the same regions in the parental virus occur. Recombinant viruses can then be selected and purified through the loss or addition of a function inserted or deleted by the plasmid used for modification, e.g. insertion or deletion of a marker gene such as GFP or lacZ from the parental virus at the intended insertion site. In a most preferred embodiment the insertion site is the ICP34.5 locus of HSV, and therefore the plasmid used for manipulation contains HSV sequences flanking this insertion site, between which are an expression cassette encoding GM-CSF and the immune co-stimulatory pathway activating molecule. In this case, the parental virus may contain a cassette encoding GFP in place of ICP34.5 and recombinant virus plaques are selected through the loss of expression of GFP. In a most preferred embodiment the US11 gene of HSV is also expressed as an IE gene. This may be accomplished through deletion of the ICP47-encoding region, or by other means.

The GM-CSF encoding sequences and immune co-stimulatory pathway activating molecule encoding sequences are inserted into the viral genome under appropriate regulatory control. This may be under the regulatory control of natural promoters of the virus species of the invention used, depending on the species and insertion site, or preferably under the control of heterologous promoters. Suitable heterologous promoters include mammalian promoters, such as the IEF2a promoter or the actin promoter. More preferred are strong viral promoters such as the CMV IE promoter, the RSV LTR, the MMLV LTR, other retroviral LTR promoters, or promoters derived from SV40. Preferably each exogenous gene (e.g. encoding the GM-CSF and immune co-stimulatory pathway activating molecule) will be under separate promoter control, but may also be expressed from a single RNA transcript, for example through insertion of an internal ribosome entry sites (IRES) between protein coding sequences. RNA derived from each promoter is typically terminated using a polyadenylation sequence (e.g. mammalian sequences such as the bovine growth hormone (BGH) poly A sequence, synthetic polyadenylation sequences, the rabbit betaglobin polyadenylation sequence, or viral sequences such as the SV40 early or late polyadenylation sequence).

Pharmaceutical Compositions

The invention provides a pharmaceutical composition comprising the virus and a pharmaceutically acceptable carrier or diluent. Suitable carriers and diluents include isotonic saline solutions, for example phosphate-buffered saline. The composition may further comprise other constituents such as sugars or proteins to improve properties such as stability of the product. Alternatively a lyophilized formulation may be used, which is reconstituted in a pharmaceutically acceptable carrier or diluent before use.

The choice of carrier, if required, is frequently a function of the route of delivery of the composition. Within this invention, compositions may be formulated for any suitable route and means of administration. Pharmaceutically acceptable carriers or diluents are those used in compositions suitable for intra-tumoral administration, intravenous/intraarterial administration, administration into the brain or administration into a body cavity (e.g. bladder, pleural cavity or by intraperitoneal administration). The composition may be administered in any suitable form, preferably as a liquid.

The present invention also provides a product of manufacture comprising a virus of the invention in a sterile vial, ampoule or syringe.

Medical Uses/Methods of Treatment

The invention provides the virus of the invention for use in the treatment of the human or animal body by therapy, particularly for use in a method of treating cancer. The cancer is typically in a mammal, preferably in a human. The virus kills infected tumour cells by lysis and by causing infected tumor cells to fuse with one another. The virus of the invention also elicits a systemic anti-tumor immune response, augmented through the expression of GM-CSF and the immune co-stimulatory pathway activating molecule, which also kills cancer cells.

The invention also provides a method of treating cancer, the method comprising administering a therapeutically effective amount of the virus of the invention to an individual in need thereof.

The invention additionally provides the use of the virus of the invention in the manufacture of a medicament for treating cancer.

The virus of the invention is particularly useful in treating any solid tumor including any adenocarcinoma, carcinoma, melanoma or sarcoma. For example, the virus of the invention is useful in treating head and neck, prostate, breast, ovarian, lung, liver, endometrial, bladder, gall bladder, pancreas, colon, kidney, stomach/gastric, esophageal, or cervical cancers, mesothelioma, melanoma or other skin cancer, lymphoma, glioma or other cancer of the nervous system, or sarcomas such as soft tissue sarcoma.

The virus of the invention may be used to treat malignant tumors, including tumors that have metastasised from the site of the original tumor. In this embodiment, the virus may be administered to the primary tumor or to one or more secondary tumors.

The virus of the invention may be administered in combination with other therapeutic agents, including chemotherapy, targeted therapy, immunotherapy (including immune checkpoint blockade, i.e. administration of one or more antagonist of an immune co-inhibitory pathway, and/or one or more agonist of an immune co-stimulatory pathway) and/or in combination with radiotherapy and/or in combination with any combination of these. The therapeutic agent is preferably an anti-cancer agent.

The virus of the invention may be administered in combination with a second virus, such as a second oncolytic virus.

For example, the therapeutic agent may comprise an immunogen (including a recombinant or naturally occurring antigen, including such an antigen or combination of antigens delivered as DNA or RNA in which it/they are encoded), to further stimulate an immune response, such as a cellular or humoral immune response, to tumor cells, particularly tumor neoantigens. The therapeutic agent may be an agent intended to increase or potentiate an immune response, such as a cytokine, an agent intended to inhibit an immune checkpoint pathway or stimulate an immune potentiating pathway or an agent which inhibits the activity of regulatory T cells (Tregs) or myeloid derived suppressor cells (MDSCs).

The therapeutic agent may be an agent known for use in an existing cancer therapeutic treatment. The therapeutic agent may be radiotherapy or a chemotherapeutic agent. The therapeutic agent may be selected from cyclophosmamide, alkylating-like agents such as cisplatin or melphalan, plant alkaloids and terpenoids such as vincristine or paclitaxel (Taxol), antimetabolites such as 5-fluorouracil, topoisomerase inhibitors type I or II such as camptothecin or doxorubicin, cytotoxic antibiotics such as actinomycin, anthracyclines such as epirubicin, glucocorticoids such as triamcinolone, inhibitors of protein, DNA and/or RNA synthesis such as methotrexate and dacarbaxine, histone deacetylase (HDAC) inhibitors, or any other chemotherapy agent.

The therapeutic agent may be one, or a combination of: immunotherapeutics or immunomodulators, such as TLR agonists; agents that down-regulate T-regulatory cells such as cyclophosphamide; or agents designed to block immune checkpoints or stimulate immune potentiating pathways, including but not limited to monoclonal antibodies, such as a CTLA-4 inhibitor, a PD-1 inhibitor, a PD-L1 inhibitor, a LAG-3 inhibitor, a TIM-3 inhibitor, a VISTA inhibitor, a CSF1R inhibitor, an IDO inhibitor, a CEACAM1 inhibitor, a GITR agonist, a 4-1-BB agonist, a KIR inhibitor, a SLAMF7 inhibitor, an OX40 agonist, a CD40 agonist, an ICOS agonist or a CD47 inhibitor. In a preferred embodiment, the therapeutic agent is a CTLA-4 inhibitor such as an anti-CTLA-4 antibody, a PD1 inhibitor, such as an anti-PD-1 antibody or a PD-L1 inhibitor such as an anti-PD-L1 antibody. Such inhibitors, agonists and antibodies can be generated and tested by standard methods known in the art.

Immunotherapeutic agents may also include bi-specific antibodies, cell based-therapies based on dendritic cells, NK cells or engineered T cells such CAR-T cells or T cells expressing engineered T cell receptors. Immunotherapeutic agents also include agents that target a specific genetic mutation which occurs in tumors, agents intended to induce immune responses to specific tumor antigens or combinations of tumor antigens, including neoantigens and/or agents intended to activate the STING/cGAS pathway, TLR or other innate immune response and/or inflammatory pathway, including intra-tumoral agents.

For example, a virus of the invention may be used: in combination with dacarbazine, a BRAF inhibitor and or CTLA-4, PD1 or PD-L1 blockade to treat melanoma; in combination with taxol, doxorubicin, vinorelbine, cyclophosphamide and/or gemcitabine to treat breast cancer; in combination with 5-fluorouracil and optionally leucovorin, irinoteacan and/or oxaliplatin to treat colorectal cancer; in combination with taxol, carboplatin, vinorelbine and/or gemcitabine, PD-1 or PD-L1 blockade to treat lung cancer; in combination with cisplatin and/or radiotherapy to treat head and neck cancer.

The therapeutic agent may be an inhibitor of the idoleamine 2,3-dioxygenase (IDO) pathway. Examples of IDO inhibitors include epacadostat (INCB024360), 1-methyl-tryptophan, Indoximod (1-methyly-D-tryptophan), GDC-0919 or F001287.

The mechanism of action of IDO in suppressing anti-tumor immune responses may also suppress immune responses generated following oncolytic virus therapy. IDO expression is induced by toll like receptor (TLR) activation and interferon-γ both of which may result from oncolytic virus infection. One embodiment of the use of oncolytic virus therapy for cancer treatment includes combination of an oncolytic virus, including a virus expressing GM-CSF and an immune co-stimulatory pathway activating molecule or molecules with an inhibitor of the IDO pathway and optionally one or more antagonist of an immune co-inhibitory pathway and/or one or more agonist of an immune co-stimulatory pathway, including those targeting CTLA-4, PD-1 and/or PD-L1.

The invention also provides a method of treating cancer, which comprises administering a therapeutically effective amount of an oncolytic virus, an inhibitor of the indoleamine 2,3-dioxygenase (IDO) pathway and a further antagonist of an immune co-inhibitory pathway, and/or an agonist of an immune co-stimulatory pathway to a patient in need thereof.

The oncolytic virus is preferably a modified clinical isolate. The oncolytic virus is preferably a pox virus, more preferably a HSV, such as a HSV1 and/or a HSV rendered functionally inactive for ICP34.5 and/or ICP47.

The oncolytic virus may express an immune stimulating molecule, such as GM-CSF and/or a co-stimulatory pathway encoding molecule such as CD4OL, GITRL, OX4OL, 4-1-BBL or ICO5L, and/or an inhibitor of CTLA-4, and/or a fusogenic protein, such as the GALV fusogenic glycoprotein with the R sequence mutated or deleted.

The further antagonist of an immune co-inhibitory pathway is preferably an antagonist of CTLA-4, an antagonist of PD1 or an antagonist of PD-L1. For example, the further antagonist of an immune co-inhibitory pathway may be an inhibitor of the interaction between PD1 and PD-L1.

Where a therapeutic agent and/or radiotherapy is used in conjunction with a virus of the invention, administration of the virus and the therapeutic agent and/or radiotherapy may be contemporaneous or separated by time. The composition of the invention may be administered before, together with or after the therapeutic agent or radiotherapy. The method of treating cancer may comprise multiple administrations of the virus of the invention and/or of the therapeutic agent and/or radiotherapy. In preferred embodiments, in the case of combination with immune checkpoint blockade or other immune potentiating agents, the virus of the invention is administered once or multiple times prior to the concurrent administration of the immune checkpoint blockade or other immune potentiating agent or agents thereafter, or concurrent with the administration of the immune checkpoint blockade or other immune potentiating agent or agents without prior administration of the virus of the invention.

The virus of the invention may be administered to a subject by any suitable route. Typically, a virus of the invention is administered by direct intra-tumoral injection. Intra-tumoral injection includes direct injection into superficial skin, subcutaneous or nodal tumors, and imaging guided (including CT, MRI or ultrasound) injection into deeper or harder to localize deposits including in visceral organs and elsewhere. The virus may be administered into a body cavity, for example into the pleural cavity, bladder or by intra-peritoneal administration. The virus may be injected into a blood vessel, preferably a blood vessel supplying a tumor.

Therapeutic agents which may be combined with a virus of the invention can be administered to a human or animal subject in vivo using a variety of known routes and techniques. For example, the composition may be provided as an injectable solution, suspension or emulsion and administered via parenteral, subcutaneous, oral, epidermal, intradermal, intramuscular, interarterial, intraperitoneal, intravenous injection using a conventional needle and syringe, or using a liquid jet injection system. The composition may be administered topically to skin or mucosal tissue, such as nasally, intratrachealy, intestinally, sublingually, rectally or vaginally, or provided as a finely divided spray suitable for respiratory or pulmonary administration. In preferred embodiments, the compositions are administered by intravenous infusion, orally, or directly into a tumor.

The virus and/or therapeutic agent may be administered to a subject in an amount that is compatible with the dosage composition that will be therapeutically effective. The administration of the virus of the invention is for a "therapeutic" purpose. As used herein, the term "therapeutic" or "treatment" includes any one or more of the following as its objective: the prevention of any metastasis or further metastasis occurring; the reduction or elimination of symptoms; the reduction or complete elimination of a tumor or cancer, an increase in the time to progression of the patient's cancer; an increase in time to relapse following treatment; or an increase in survival time.

Therapeutic treatment may be given to Stage I, II, III, or IV cancers, preferably Stage II, III or IV, more preferably Stage III or IV, pre- or post-surgical intervention (i.e. following recurrence or incomplete removal of tumors following surgery), preferably before any surgical intervention (either for resection of primary or recurrent/metastatic disease), or following recurrence following surgery or following incomplete surgical removal of disease, i.e. while residual tumor remains.

Therapeutic treatment may be carried out following direct injection of the virus composition into target tissue which may be the tumor, into a body cavity, or a blood vessel. As a guide, the amount of virus administered is in the case of HSV in the range of from $10^4$ to $10^{10}$ pfu, preferably from $10^5$ to $10^9$ pfu. In the case of HSV, an initial lower dose (e.g. $10^4$ to $10^7$ pfu) may be given to patients to seroconvert patients who are seronegative for HSV and boost immunity in those who are seropositive, followed by a higher dose then being given thereafter (e.g. $10^6$ to $10^9$ pfu). Typically up to 20 ml of a pharmaceutical composition consisting essentially of the virus and a pharmaceutically acceptable suitable carrier or diluent may be used for direct injection into tumors, or up to 50 ml for administration into a body cavity (which may be subject to further dilution into an appropriate diluent before administration) or into the bloodstream. However for some oncolytic therapy applications larger or smaller volumes may also be used, depending on the tumor and the administration route and site.

The routes of administration and dosages described are intended only as a guide since a skilled practitioner will be able to determine readily the optimum route of administration and dosage. The dosage may be determined according to various parameters, especially according to the location of the tumor, the size of the tumor, the age, weight and condition of the patient to be treated and the route of administration. Preferably the virus is administered by direct injection into the tumor or into a body cavity. The virus may also be administered by injection into a blood vessel. The optimum route of administration will depend on the location and size of the tumor. Multiple doses may be required to achieve an immunological or clinical effect, which, if required, will be typically administered between 2 days to 12 weeks apart, preferably 3-days to 3 weeks apart. Repeat doses up to 5 years or more may be given, preferably for up to one month to two years dependent on the speed of response of the tumor type being treated and the response of a particular patient, and any combination therapy which may also be being given.

The following Examples illustrate the invention.

Example 1. Construction of a Virus of the Invention

The virus species used to exemplify the invention is HSV, specifically HSV1. The strain of HSV1 used for exemplification is identified through the comparison of more than 20 primary clinical isolates of HSV1 for their ability to kill a panel of human tumor-derived cell lines and choosing the virus strain with the greatest ability to kill a broad range of these rapidly, and at low dose. Tumor cell lines used for this comparison include U87MG (glioma), HT29 (colorectal), LNCaP (prostate), MDA-MB-231 (breast), SK-MEL-28 (melanoma), Fadu (squamous cell carcinoma), MCF7 (breast), A549 (lung), MIAPACA-2 (pancreas), CAPAN-1 (pancreas), and/or HT1080 (fibrosarcoma).

Specifically, each primary clinical isolate of HSV is titrated onto each of the cell lines used for screening at MOIs such as 1, 0.1, 0.01 and 0.001 and assessed for the extent of cell death at time points such as 24 and 48 hrs at each dose. The extent of cell killing may be assessed by e.g. microscopic assessment of the proportion of surviving cells at each time point, or e.g. a metabolic assay such as an MTT assay. The exemplary virus of the invention is then constructed by deletion of ICP47 from the viral genome using homologous recombination with a plasmid containing regions flanking HSV1 nucleotides 145300 to 145582 (HSV1 nucleotides 145300 to 145582 being the sequences to be deleted; HSV1 strain 17 sequence Genbank file NC 001806.2) between which are encoded GFP. GFP expressing virus plaques are selected, and GFP then removed by homologous recombination with the empty flanking regions and plaques which do not express GFP are selected. This results in an ICP47 deleted virus in which US11 is expressed as an IE protein as it is now under the control of the ICP47 promoter. ICP34.5 is then deleted using homologous recombination with a plasmid containing regions flanking HSV1 nucleotides 124953 to 125727 (HSV1 nucleotides 124953 to 125727 being the sequences to be deleted; HSV1 strain 17 sequence Genbank file NC 001806.2) between which GFP is encoded. GFP expressing virus plaques are again selected, and GFP then removed by homologous recombination with the same flanking regions but between which are now an expression cassette comprising a codon optimized version of the mouse GM-CSF sequence, a codon optimized version of the GALV R- sequence and codon optimized version of mouse soluble multimeric CD40L driven by a CMV, an RSV and an SV40 promoter. Non-GFP expressing plaques are selected.

The structure of the resulting virus is shown in FIG. 1. The mGM-CSF, CD40L and GALV-R- sequences are shown in SEQ ID NOs 2, 14 and 8 respectively. The structure of the resulting virus is confirmed by restriction digestion and Southern blot, GM-CSF and CD40L expression is confirmed by ELISA, and GALV-R- expression is confirmed by infection of human HT1080 tumor cells and the observation of syncitial plaques.

Viruses are also constructed using similar procedures which only have inserted the gene for GALVR- or mouse GM-CSF and GALV-R-, but without CD40L. The structures of these viruses are also shown in FIG. 1.

For human use, hGM-CSF and hCD40L are used, the sequence for codon optimised versions of which are shown in SEQ ID NO 4 and 13.

Example 2. The Effect of the Combined Expression of GM-CSF and an Immune Co-Stimulatory Pathway Activating Molecule from an Oncolytic Virus in Mouse Tumor Models The GALV R- protein causes cell to cell fusion in human cells but not in mouse cells because the PiT-1 receptor required for cell fusion to occur has a sequence in mice which does not allow cell fusion to occur. As a result mouse tumor cells expressing human PiT-1 are first prepared using methods standard in the art. Human PiT-1 is cloned into a lentiviral vector also comprising a selectable marker gene. The vector is transfected into target CT26 mouse colorectal cancer tumor cells and clones resistant to the selectable marker are selected to generate CT26/PiT-1 cells. PiT-1 expression is confirmed by western blotting in untransfected cells and in cells transfected with the PiT-1 expressing lentivirus and by transfection of a plasmid expressing GALV-R- and confirmation that cell fusion occurs.

The utility of the invention is demonstrated by administering CT26/PiT-1 cells into both flanks of Balb/c nice and allowing the CT26/PiT-1 tumors to grow to approximately 0.5 cm in diameter.

The following treatments are then administered to groups of mice (five per group), into one flank of each mouse only 3 times per week for two weeks:

50 µl of saline (1 group);

50 µl of $10^5$ pfu/ml, $10^6$ pfu/ml, or $10^7$ pfu/ml of the ISV with only GALVR- inserted (3 groups);

50 µl of $10^5$ pfu/ml, $10^6$ pfu/ml, or $10^7$ pfu/ml of the HSV with only GALVR- and mouse GM-CSF inserted (3 groups);

50 µl of $10^5$ pfu/ml, $10^6$ pfu/ml, or $10^7$ pfu/ml of the virus with GALVR- and both mouse GM-CSF and CD40L inserted (3 groups).

Effects on tumor growth are then observed for up to one month. Superior tumor control and shrinkage in both injected and uninjected tumors with the virus expressing GM-CSF and CD40L as compared to the other groups is observed, including through an improved dose response curve.

Example 3. The Effect of Combined Expression of GM-CSF and an Immune Co-Stimulatory Pathway Activating Molecule from an Oncolytic Virus on the Therapeutic Effect of Immune Checkpoint Blockade in Mouse Tumor Models The experiment in Example 2 above is repeated but mice are additionally dosed bi-weekly by the intra-peritoneal route with an antibody targeting mouse PD-1 (10 mg/kg; Bioxcell RMP-1-14 on the same days as virus dosing) or an antibody targeting mouse CTLA-4 (10 mg/kg; Bioxcell 9H10 on the same days as virus dosing). An additional group of mice is added which receive no antibody treatment. More specifically, groups of mice receive (1) saline, (2) HSV with GALVR- inserted as in Example 2, (3) HSV with GM-CSF and GALV-R- inserted as in Example 2, (4) HSV with GM-CSF, CD40L and GALV-R- inserted as in Example 2, (5) PD-1 antibody, (6) CTLA-4 antibody, (7) HSV with GALVR- inserted plus PD-1 antibody, (8) HSV with GALV-R- inserted gene plus CTLA-4 antibody, (9) HSV with GM-CSF and GALV-R- and PD-1 antibody or (10) HSV with GM-CSF and GALV-R- and CTLA-4 antibody (11) HSV with GM-CSF, CD40L and GALV-R- and PD-1 antibody or (12) HSV with GM-CSF, CD40L and GALV-R- and CTLA-4 antibody. Superior tumor control and shrinkage in both injected and uninjected tumors with the virus expressing GM-CSF and CD40L together with the anti-PD-1 antibody or the anti-CTLA-4 antibody as compared to the other groups is observed, including through an improved dose response curve.

Example 4. Collection of Clinical Isolates

The virus species used to exemplify the invention is HSV, specifically HSV1. To exemplify the invention, 181 volunteers were recruited who suffered from recurrent cold sores. These volunteers were given sample collection kits (including Sigma Virovult collection tubes), and used these to swab cold sores when they appeared following which these samples were shipped to Replimune, Oxford UK. From June 2015-February 2016, swabs were received from 72 volunteers. A sample of each swab was used to infect BHK cells. Of these 36 live virus samples were recovered following plating out and growth on BHK cells. These samples are detailed in Table 1.

TABLE 1

Details of Tested Swab Samples & Result

| Sample Number | Virus retrieved |
| --- | --- |
| RH001A | No |
| RH001B | |
| RH002A | Yes |
| RH003A | No |
| RH004A | Yes |
| RH004B | |
| RH005A | No |
| RH005B | |
| RH006A | No |
| RH006B | |
| RH007A | Yes |
| RH007B | |
| RH007C | |
| RH008A | No |
| RH008B | |
| RH008C | |
| RH009A | No |
| RH009B | |
| RH010A | No |
| RH011A | No |
| RH011B | |
| RH011C | |
| RH012A | No |
| RH013A | No |
| RH014A | Yes |
| RH014B | |
| RH015A | Yes |
| RH016A | No |
| RH016B | |
| RH017A | Yes |
| RH018A | Yes |
| RH018B | |
| RH018C | |
| RH019A | No |
| RH019B | |
| RH019C | |
| RH020A | Yes-RH020A only |
| RH020B | |
| RH020C | |
| RH021A | Yes |
| RH021B | |
| RH022A | Yes |
| RH022B | |
| RH023A | Yes |
| RH024A | No |
| RH025A | Yes-RH025B only |
| RH025B | |
| RH026A | Yes |
| RH027A | No |
| RH027B | |

TABLE 1-continued

Details of Tested Swab Samples & Result

| Sample Number | Virus retrieved |
|---|---|
| RH027C | |
| RH028A | No |
| RH028B | |
| RH028C | |
| RH029A | No |
| RH030A | No |
| RH031A | Yes-RH031A to |
| RH031B | RH031D |
| RH031C | |
| RH031D | |
| RH031E | |
| RH031F | |
| RH032A | No |
| RH033A | No |
| RH033B | |
| RH033C | |
| RH034A | No |
| RH034B | |
| RH034C | |
| RH035A | No |
| RH036A | Yes |
| RH037A | Yes |
| RH038A | Yes |
| RH039A | No |
| RH039B | |
| RH039C | |
| RH040A | Yes |
| RH040B | |
| RH040C | |
| RH041A | Yes |
| RH042A | Yes |
| RH043A | No |
| RH043B | |
| RH043C | |
| RH044A | No |
| RH045A | No |
| RH046A | Yes |
| RH047A | Yes-RH047A and |
| RH047B | RH047C |
| RH047C | |
| RH048A | No |
| RH049A | No |
| RH049B | |
| RH049C | |
| RH050A | No |
| RH051A | Yes |
| RH051B | |
| RH052A | Yes-RH052A only |
| RH052B | |
| RH053A | No |
| RH054A | No |
| RH055A | No |
| RH055B | |
| RH056A | Yes |
| RH057A | No |
| RH058A | Yes |
| RH058B | |
| RH059A | No |
| RH060A | No |
| RH061A | Yes |
| RH062A | No |
| RH063A | No |
| RH064A | Yes |
| RH065A | Yes |
| RH065B | |
| RH066A | No |
| RH067A | No |
| RH067B | |
| RH068A | No-contaminated |
| RH069A | No |
| RH069A | |
| RH070A | Yes |
| RH071A | Yes |
| RH072A | No |
| RH073A | Yes |
| RH073B | |
| RH074A | No |
| RH074B | |
| RH075A | No |
| RH076A | No |
| RH078A | No |
| RH078B | |
| RH079B | Yes |
| RH079B | |
| RH080A | No |
| RH081A | Yes |
| RH082A | No |
| RH082B | |
| RH083A | Yes |
| RH083B | |
| RH084A | Yes |
| RH084B | |
| RH084C | |
| RH085A | No |
| RH086A | No |
| RH087A | Yes-RH078B only |
| RH087B | |

Designations A, B, C etc. indicate multiple swabs from the same volunteer.

Example 5. Identification of Clinical Isolates with Improved Anti-Tumor Effects The abilities of the primary clinical isolates of HSV1 to kill a panel of human tumor-derived cell lines was tested. The tumor cell lines used for this comparison were HT29 (colorectal), MDA-MB-231 (breast), SK-MEL-28 (melanoma), Fadu (squamous cell carcinoma), MCF7 (breast), A549 (lung), MIAPACA-2 (pancreas) and HT1080 (fibrosarcoma). The cell lines were used to test for the level of CPE achieved at a range of MOI and times post infection for each of the primary clinical isolates.

Experiments were conducted in parallel using 5 to 8 of the new viruses strains at the same time. The virus strains were plated out in duplicate at a range of MOIs (0.001-1), and the extent of CPE following crystal violet staining was assessed at 24 and 48 hours following infection. The viral strains which were most effective at killing the tumor cell lines were scored, and the most effective two or three strains from each screen of 5-8 strains were identified and compared in parallel in a further experiment to identify the top strains for further development.

The initial screens demonstrated substantial variability in the ability of the different strains to kill the different tumor cell lines. Of an initial 29 strains tested, 8 strains of interest were identified in the initial screens for further comparison. These were strains RH004A, RH015A, RH018A, RH021A, RH1023A, RH31A, RH040A, and RH047A.

Figure 2:
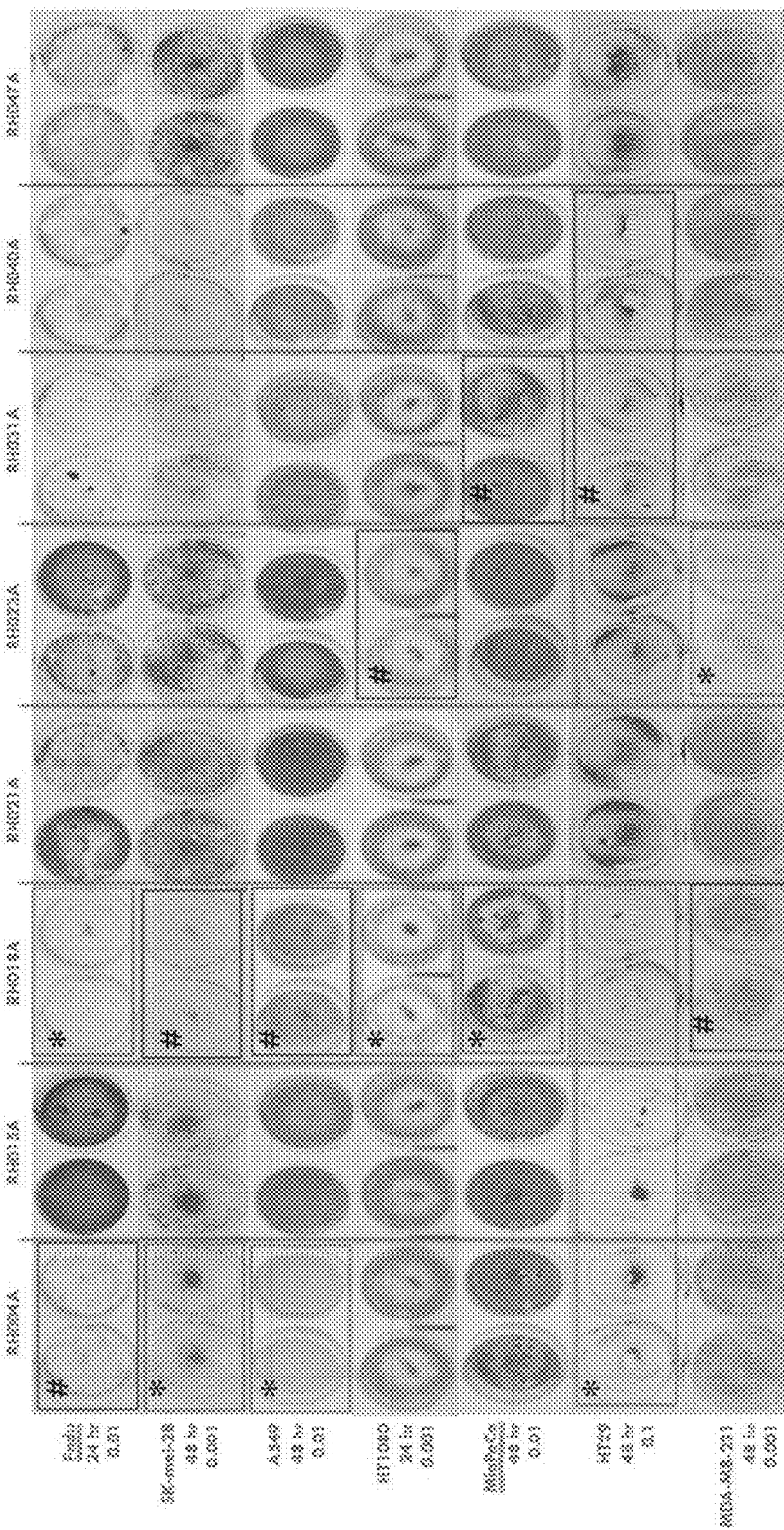
FIG. 2 shows the differential abilities of the eight top ranking HSV1 clinical isolate strains as assessed by crystal violet staining 24 hours or 48 hours after infection with a MG of 0.1, 0.01 or 0.001 as indicated in the Figure to kill Fadu, SK-mel-28, A549, HT1080, MIA-PA-CA-2, HT29 and MDA-MB-231 human tumor cell lines. The virus strains ranked first and second on each cell line are indicated. The virus RH018A was ranked first on each of the Fadu, HT1080, MIA-PA-CA-2 and HT29 cell lines and second on each of the SK-mel-28, A549 and MDA-MB-231 cell lines. RH004A was ranked joint first with RH018A and RH015A on the HT29 cell line, first on the SK-mel-28 and A549 cell lines and second on the Fadu cell line. RH023A was ranked first on the MDA-MB-231 cell line and second on the HT1080 cell line. RH031A was ranked second on each of the MIA-PA-CA-2 and HT29 cell lines. RH040A was ranked joint second on the HT29 cell line.

The 8 strains for further comparison were tested in parallel on the panel of tumor cell lines, and their relative ability to kill these tumor cell lines was assessed following crystal violet staining and observation for CPE. FIG. 2 shows a representative dine point and MOI for these viruses on each of the viruses on each of the cell lines demonstrating the differential ability of the viruses to kill the target tumor cell lines observed.

There was substantial variation amongst the strains, and it was found that while a particular strain may be particularly effective at killing one cell line, it is not necessarily particularly effective at killing other cell lines too, further demonstrating the degree of variability in the ability of clinical strains of HSV to kill tumor cells of different types.

Figure 3:
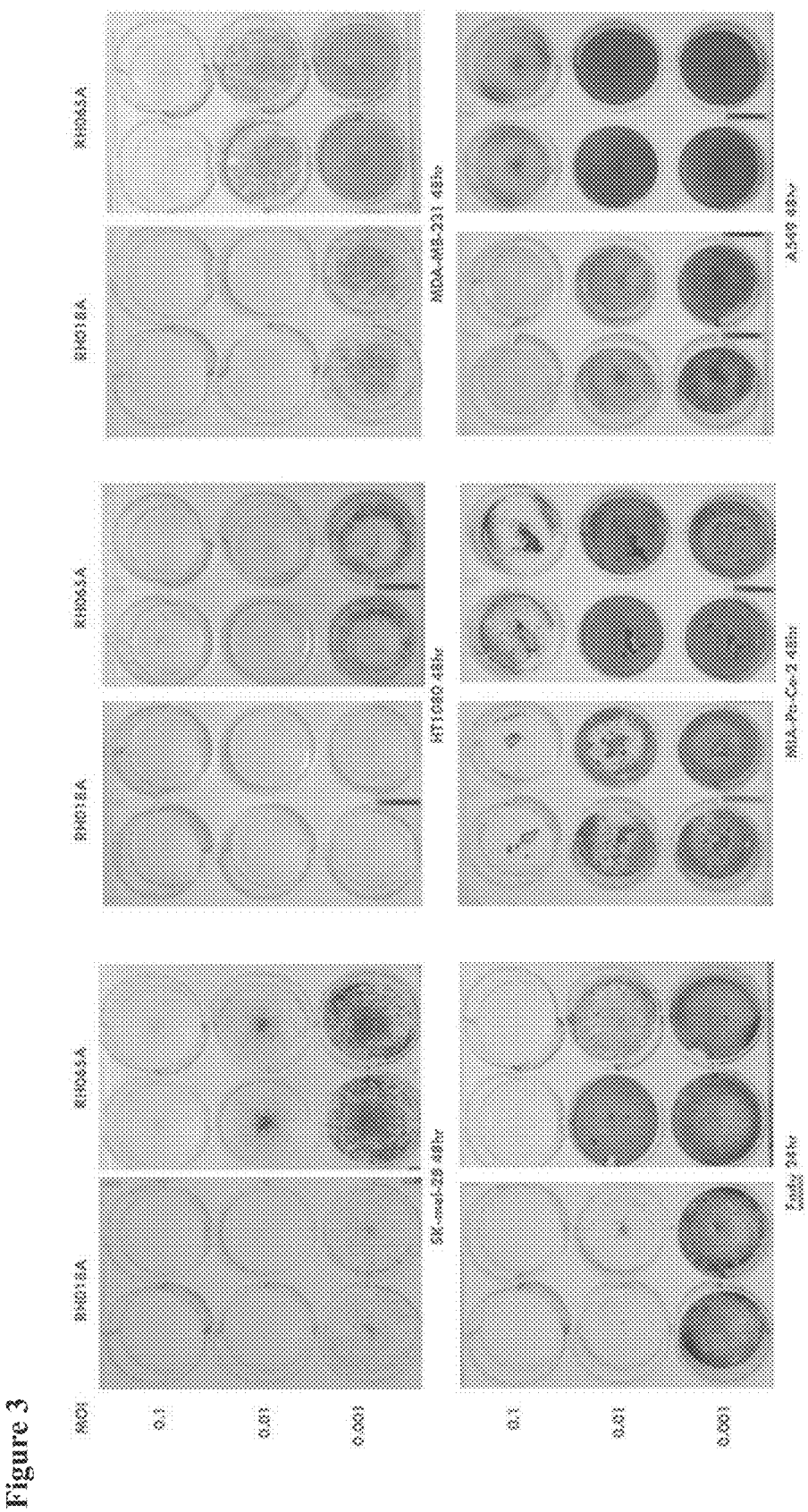
FIG. 3 shows a comparison between strain RH018A, the strain ranked first of all the strains tested, with an 'average' strain from the screen (i.e. strain RH065A). Approximately 10 fold less of strain RH018A was needed to kill an equal proportion of cells than was needed of strain R1065A as shown by crystal violet staining 24 or 48 hours post infection with MOIs of 0.1, 0.01 and 0.001 in SK-mel-28, HT1080, MDA-MB-231, Fadu. MIA-PA-CA-2 and A549 cell lines.
Figure 4A:
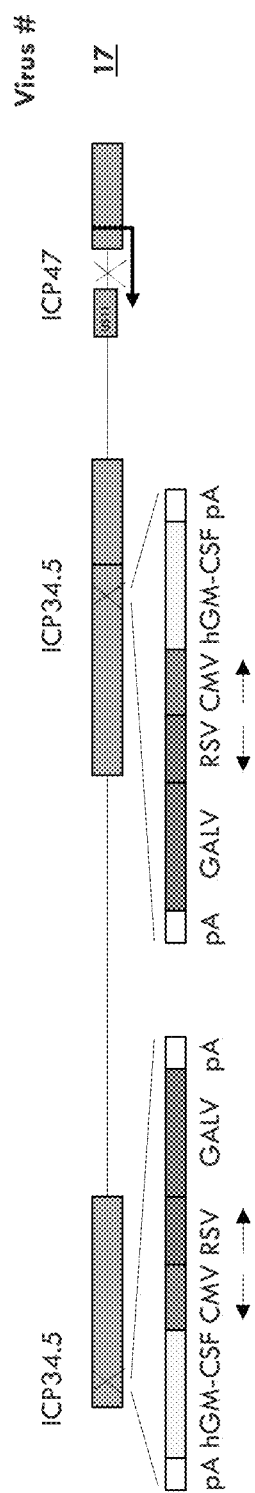
FIGS. 4A-4F and 5A-5F depict structures of HSV1 viruses modified by the deletion of ICP34.5 and ICP47 such that the US11 gene is under control of the ICP457 immediate early promoter and containing heterologous genes in the ICP34.5 locus. The viruses were constructed using the RH018A strain unless otherwise stated in the Figure.
Figure 4B:
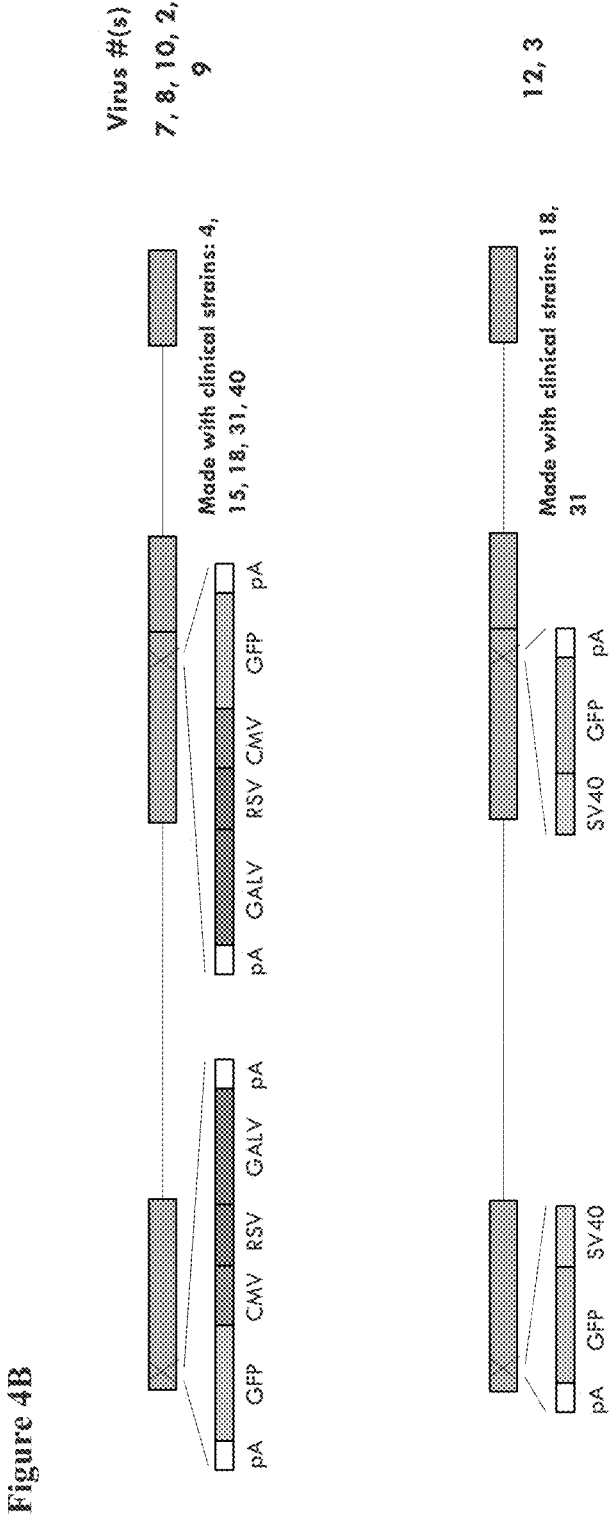
Figure 4C:
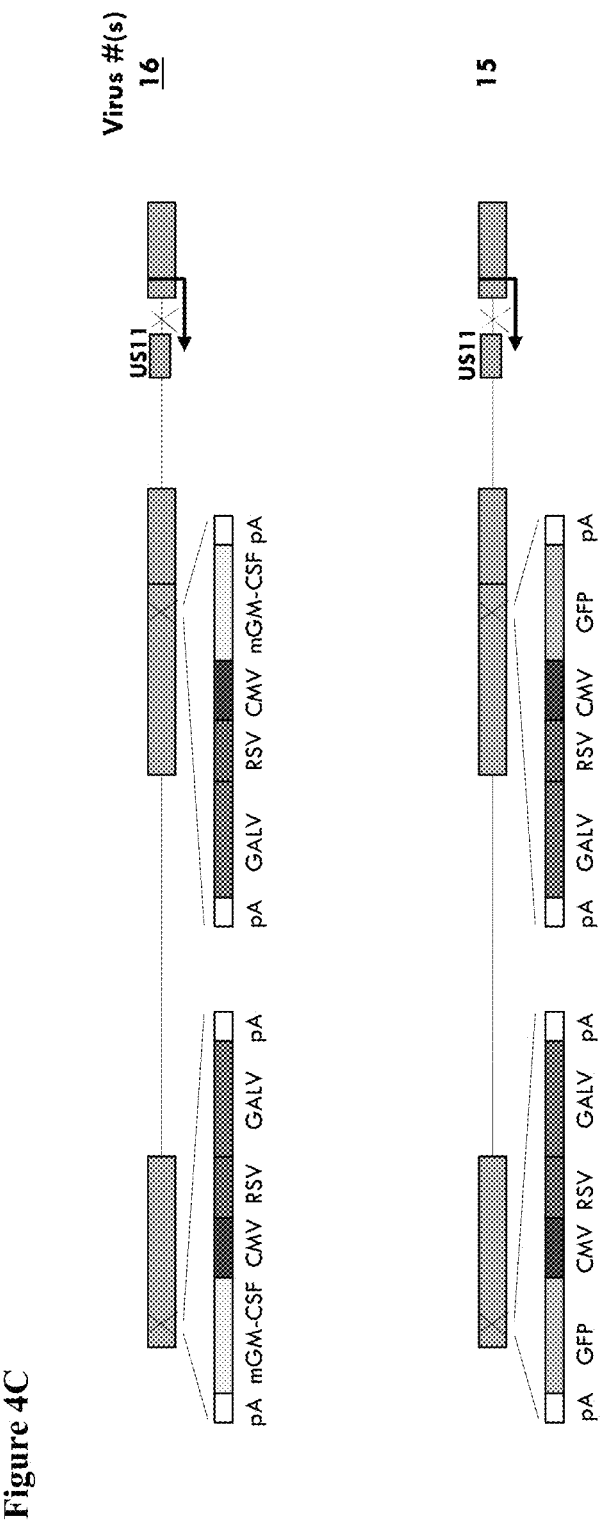
Figure 4D:
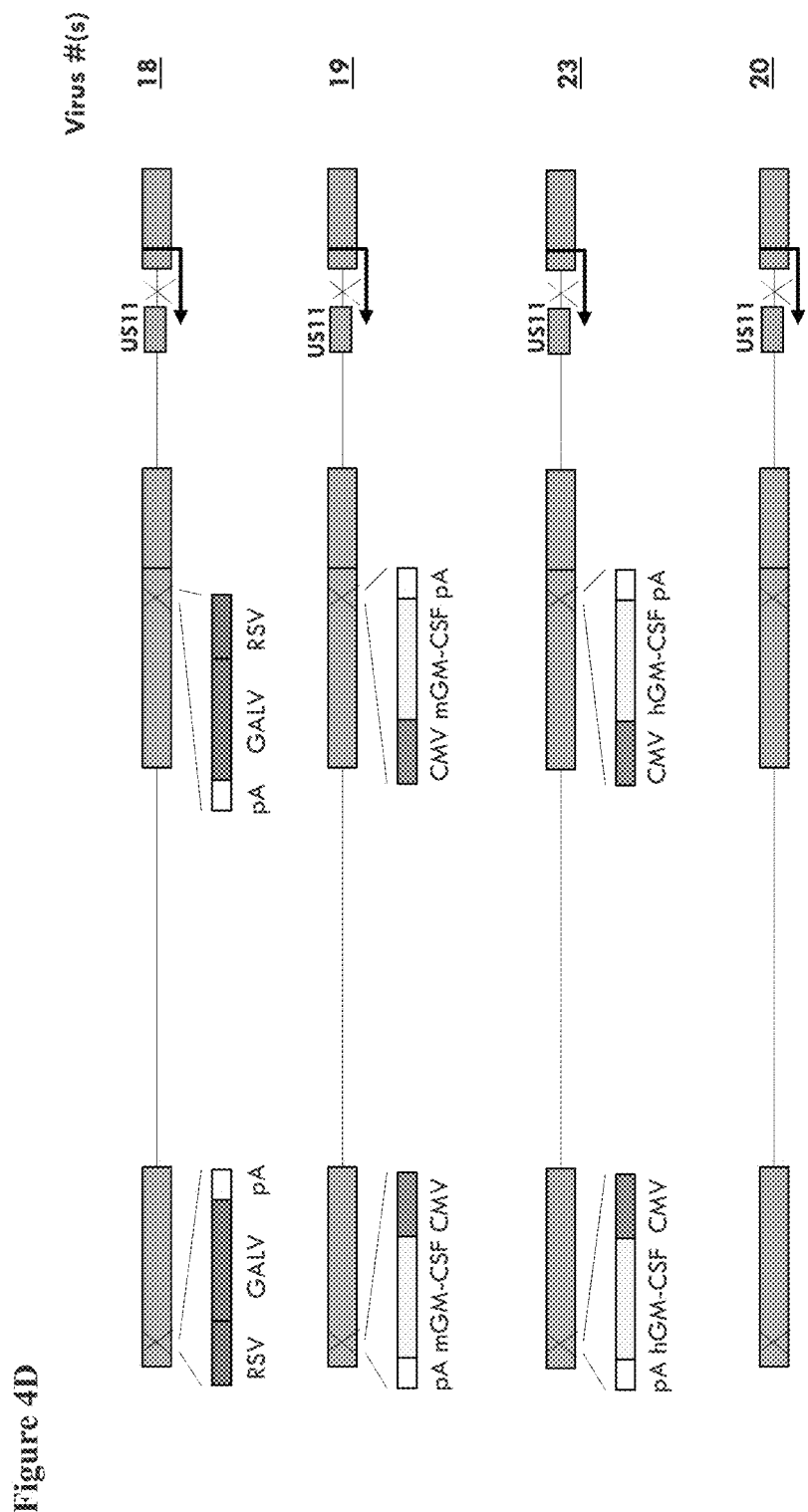
Figure 4E:
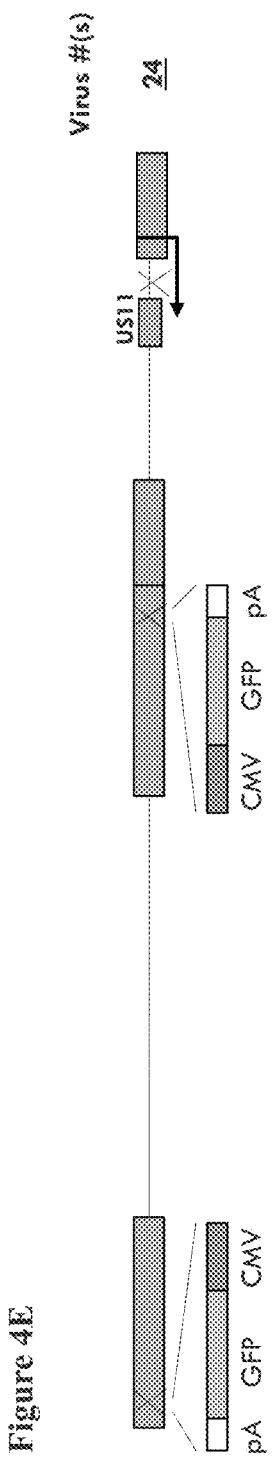
Figure 4F:
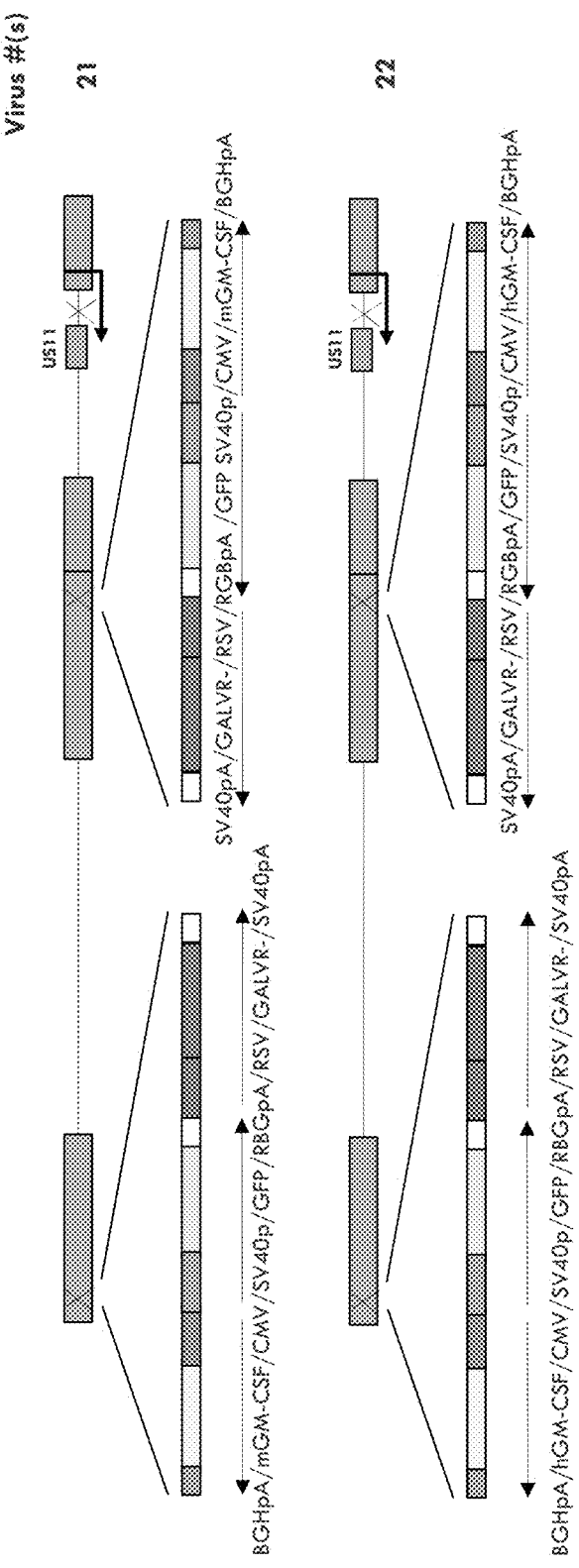
Figure 5A:
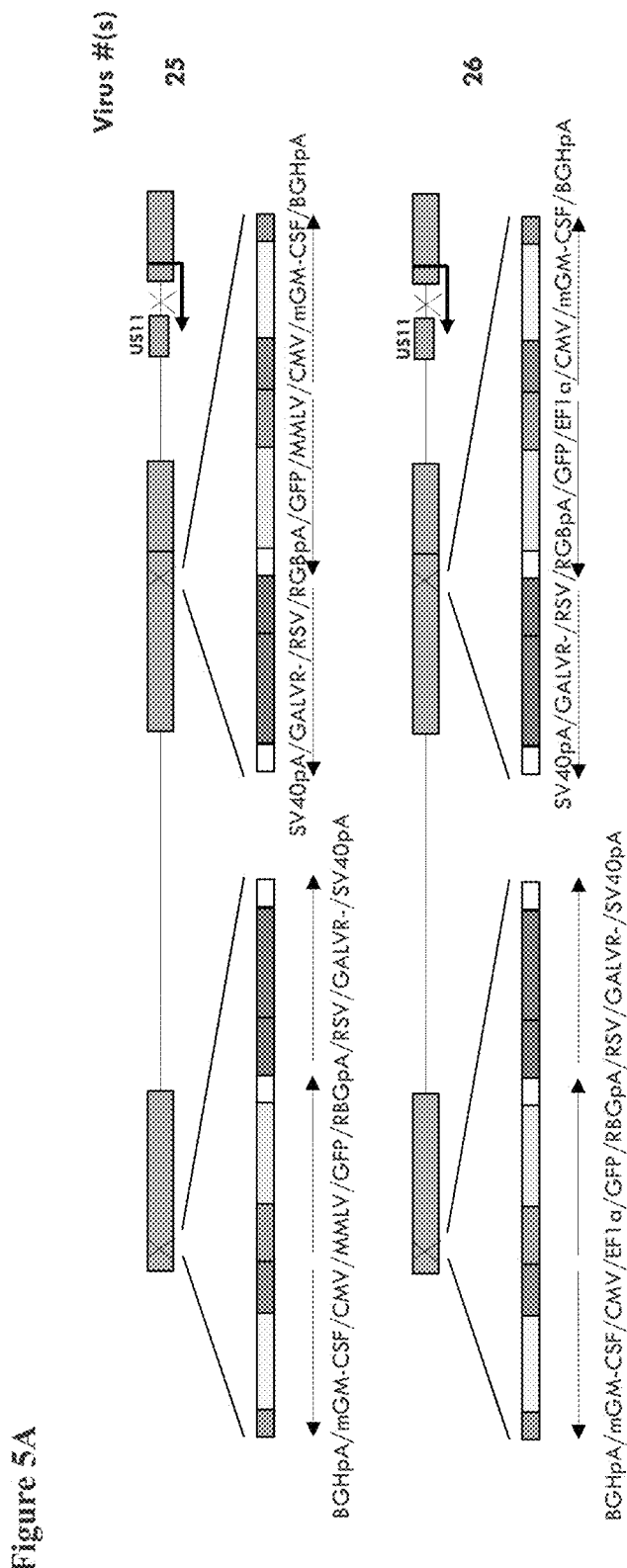
Figure 5B:
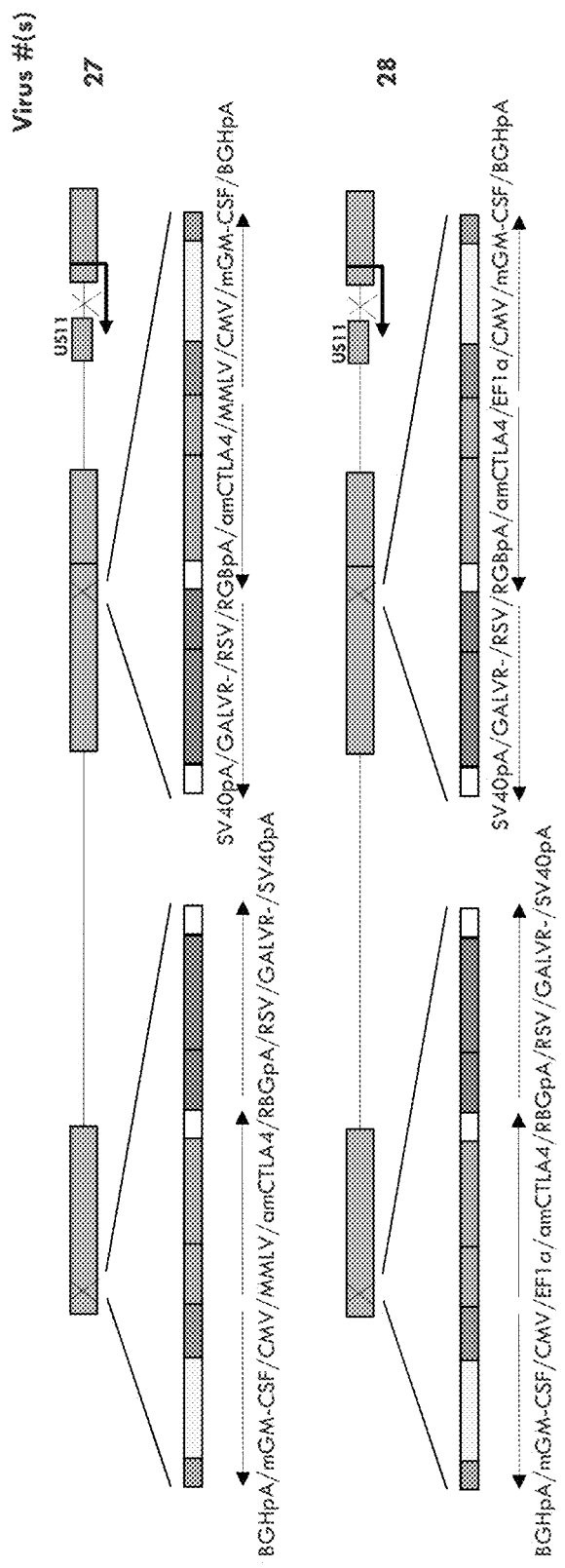
Figure 5C:
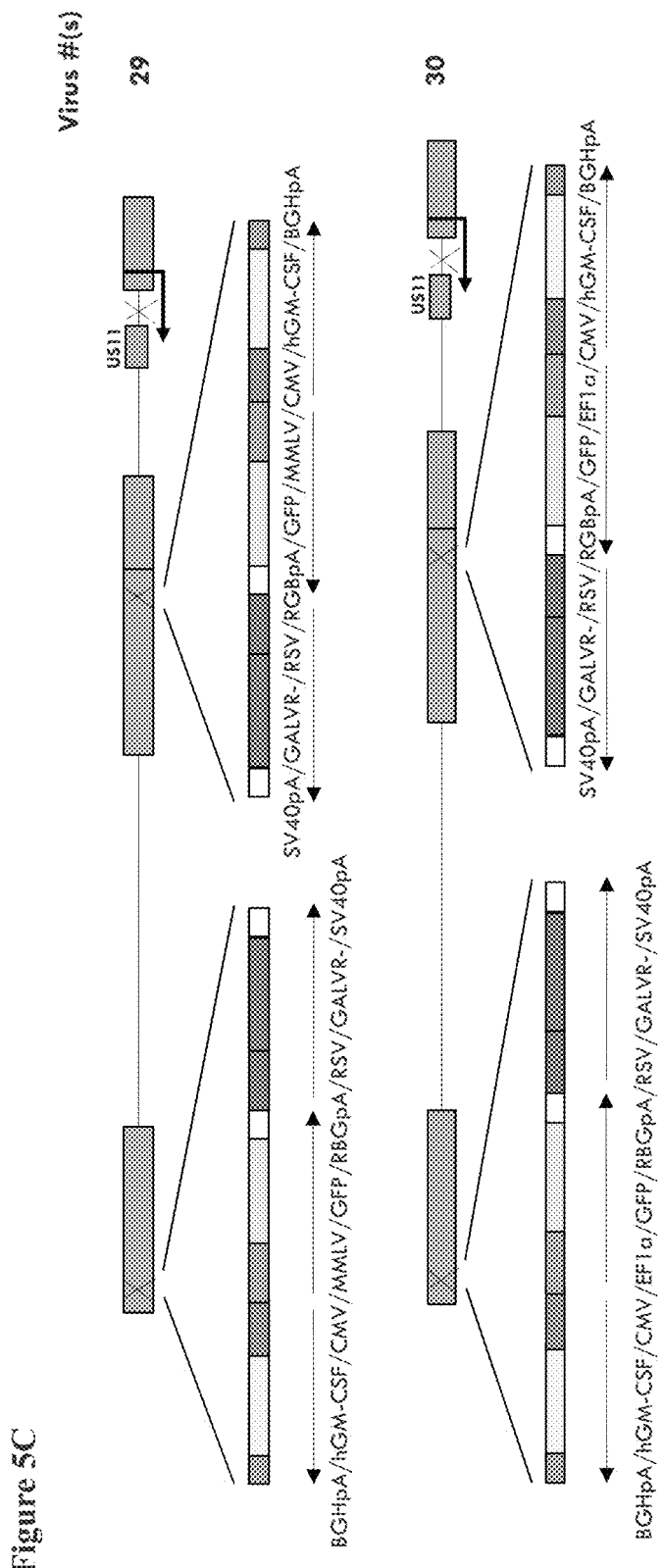
Figure 5D:
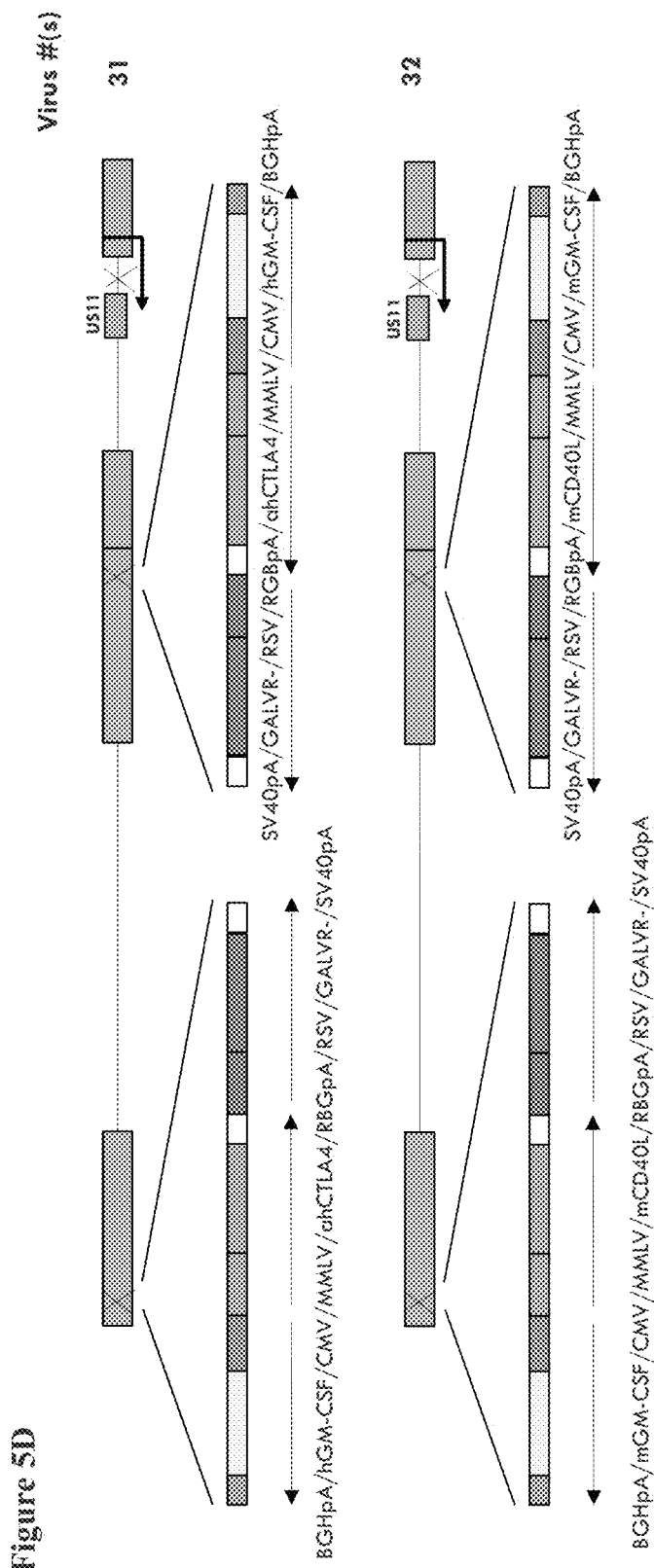
Figure 5E:
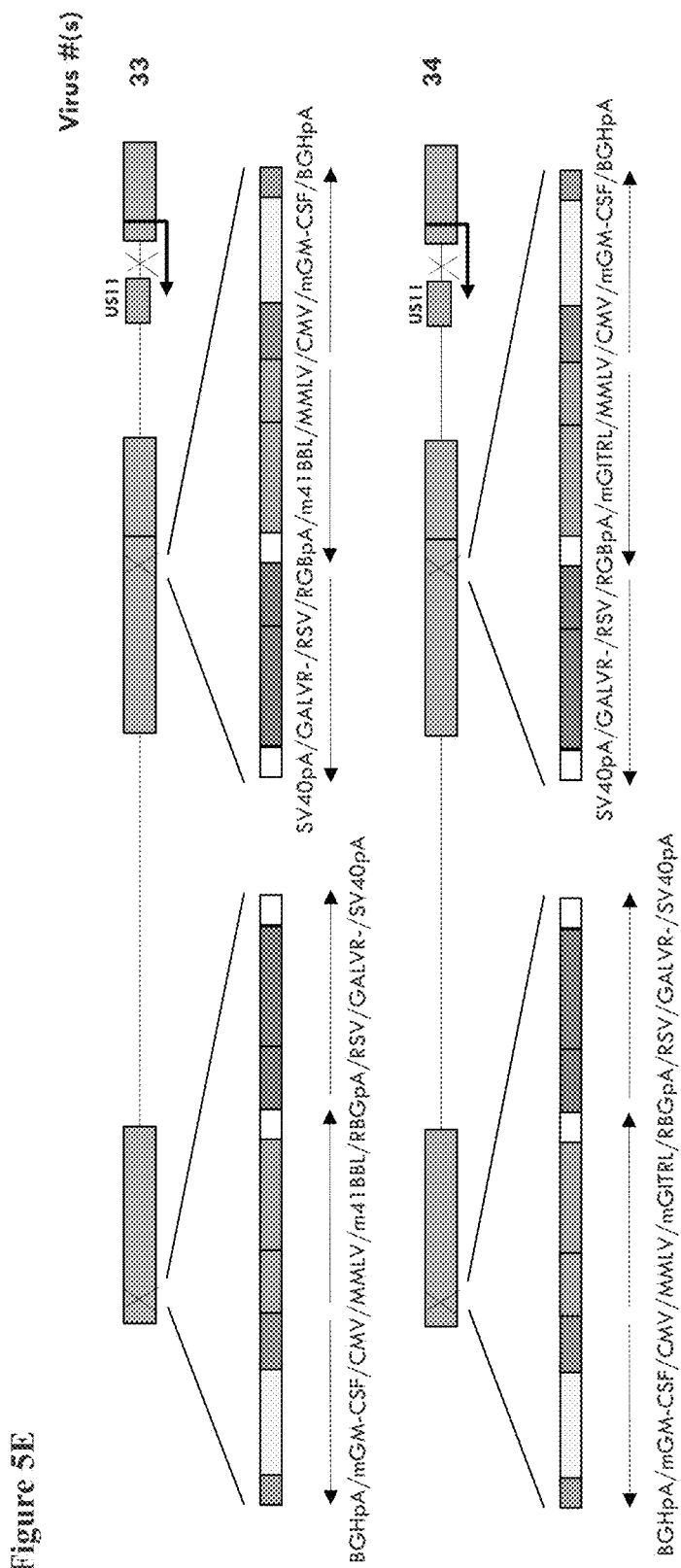
Figure 5F:
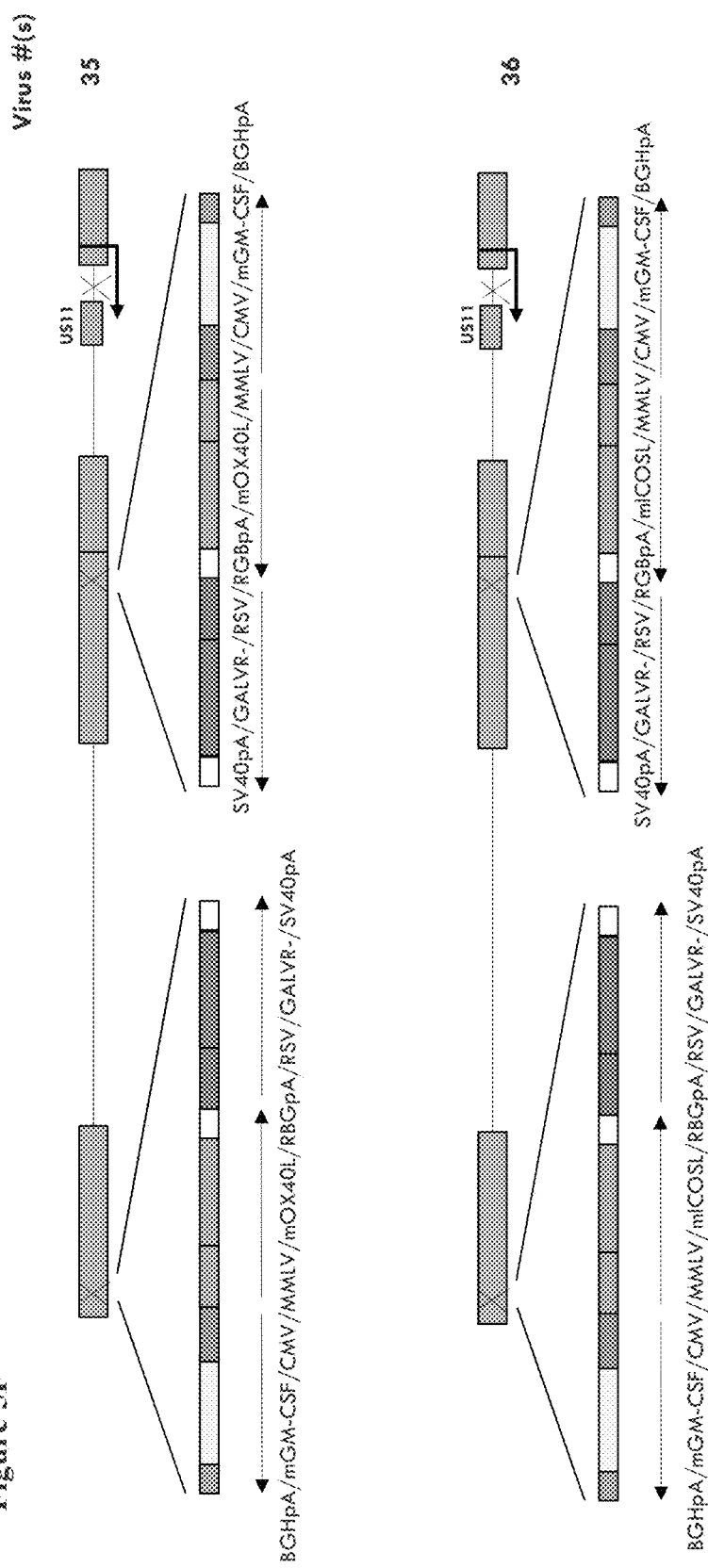

FIG. 3 also indicates which of the virus strains was both best and second best at killing each of the cell lines, enabling the virus strains to be rank ordered as to their overall relative ability to kill the panel of cell lines as a whole. This analysis demonstrated that strains RH004A, RH015A, RH018A, RH031A and RH040A were relatively more effective than the other strains, and these five strains were chosen for potential further development as oncolytic agents. Of these top five strains, the relative rank order based on their abilities to kill across the panel of cell lines was RH1018A>RH004A>RH031A>RH040A>RH015A.

More specifically, in these experiments, the tumor cell lines were used to seed multi-well tissue culture plates so that they were about 80% confluent on the day of infection. Representative wells from each tumor cell line were trypsinised and the number of cells in the well determined. These cell counts are used to determine the volume of each clinical isolate required to give an MOI of 1, 0.1, 0.01 and 0.001. Separate wells of a tumor cell line were infected with the clinical isolate at these MOI. All infections are carried out in quadruplicate. Duplicate wells were incubated for 24 hours and duplicate wells were incubated for 48 hours, both at 37° C., 5% $CO_2$, prior to fixation of the cells with glutaraldehyde and staining with crystal violet. The level of cell lysis was then assessed by gross observation, microscopy (cell counts) and photography.

Strain RH018A, the strain ranked first of all the strains tested was compared to an 'average' strain from the screen (i.e. a strain which was not in the top 8, but was also not in the group of strains which were least effective and killing the panel of tumor cell lines). This comparison showed that Strain RH018A was approximately 10 fold more effective than this average strain (Strain RH065A) at killing the tumor cell lines (i.e. approximately 10 fold less of Strain RH018A was needed to kill an equal proportion of cells than was needed of Strain RH065A). This is shown in FIG. 3.

Example 6. Modification of Clinical Isolates

In this Example the clinical isolates selected in Example 5 were modified by deletion of ICP34.5 from the viral genome using homologous recombination with a plasmid containing regions flanking the ICP34.5 encoding gene (nucleotides 143680-145300 and 145.582-147.083: HSV1 strain 17 sequence Genbank file NC 001806.2) between which are encoded GFP and the GALV-R-fusogenic glycoprotein. The structure of this virus, (Virus 10) is shown in FIGS. 4A-4F.

Additional viruses based on Strain RH018A were also constructed in which both ICP34.5 and ICP47 (using flanking regions containing nucleotides 123464-124953 and 125727-126781; HSV1 strain 17 sequence Genbank file NC 001806.2) were deleted (resulting in placement of US11 under the control of the ICP47 promoter). To construct these viruses, GFP expressing virus plaques, with GFP expressed in place of ICP47 were first selected. GFP was then removed by homologous recombination with the empty flanking regions, and plaques not expressing GFP were selected. This resulted in an ICP47 deleted virus in which US11 is expressed as an IE protein as it is now under the control of the ICP47 promoter. ICP34.5 was then deleted using homologous recombination with a plasmid containing regions flanking HSV1 nucleotides 143680-145300 and 145,582-147,083; HSV1 strain 17 sequence Genbank file NC 001806.2) between which GFP is encoded. GFP expressing virus plaques were again selected, and GFP then removed by homologous recombination with the same flanking regions but between which are now an expression cassette comprising the genes to be inserted. The viruses that were constructed are shown in FIGS. 1, 4 and 5. These included a codon optimized version of the mouse GM-CSF sequence and a codon optimized version of the GALV R-sequence driven by the CMV IE promoter and RSV promoter respectively, in a back to back orientation and again selecting virus plaques which do not express GFP. This virus construction was performed using methods which are standard in the art.

The mGM-CSF and GALV-R- sequences are shown in SEQ ID NOs 2 and 8 respectively. The structure of the resulting virus was confirmed by PCR, GM-CSF expression was confirmed by ELISA, and GALV-R- expression was confirmed by infection of human HT1080 tumor cells and the observation of syncitial plaques.

Figure 6:
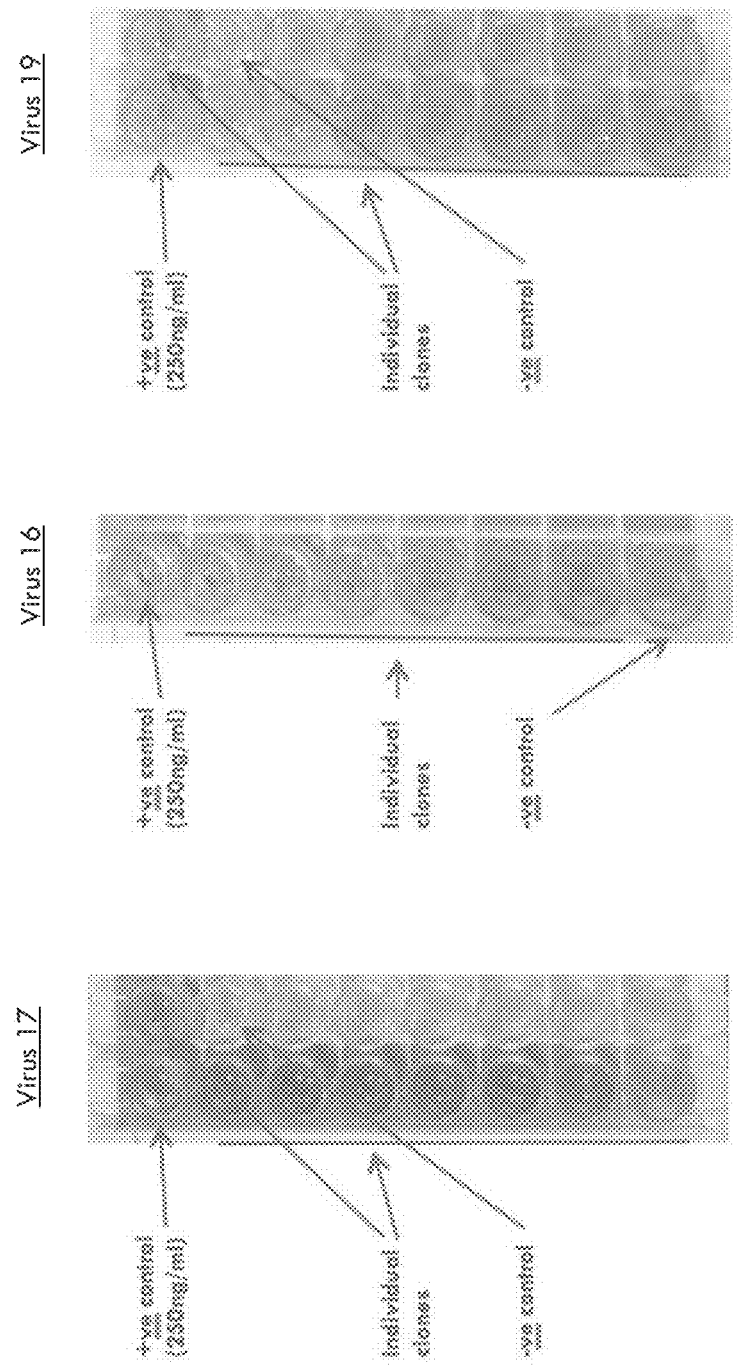
FIG. 6 shows the results of an ELISA to detect expression of human or mouse GM-CSF in supernatants from BHK cells infected with virus 16 (mGM-CSF and GALVR-), virus 17 (hGM-CSF and GALVR-) and virus 19 (mGM-CSF).

For human use, hGM-CSF is used, the sequence for a codon optimised version of which is shown in SEQ ID NO 4. The structure of this virus is shown in FIGS. 4A-4F. Expression of mouse or human GM-CSF from viruses 16, 17 and 19 is shown in FIG. 6.

Figure 7A:
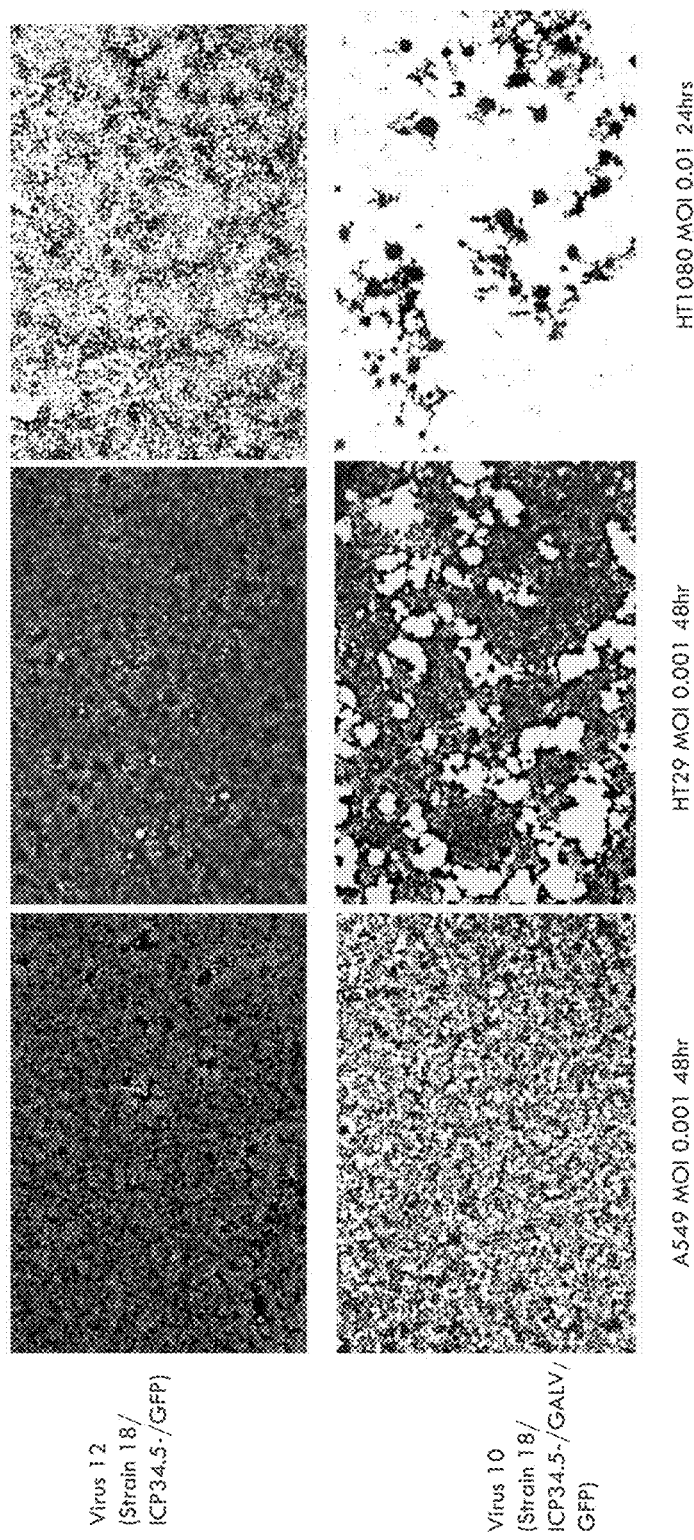
FIGS. 7A-7B is a comparison between the cell-killing abilities of strain RH018A in which ICP34.5 is deleted and which expresses GALVR- and GFP (virus 10) with a virus that expresses only GFP (virus 12) as determined by crystal violet staining in three cell lines at low magnification.
Figure 7B:
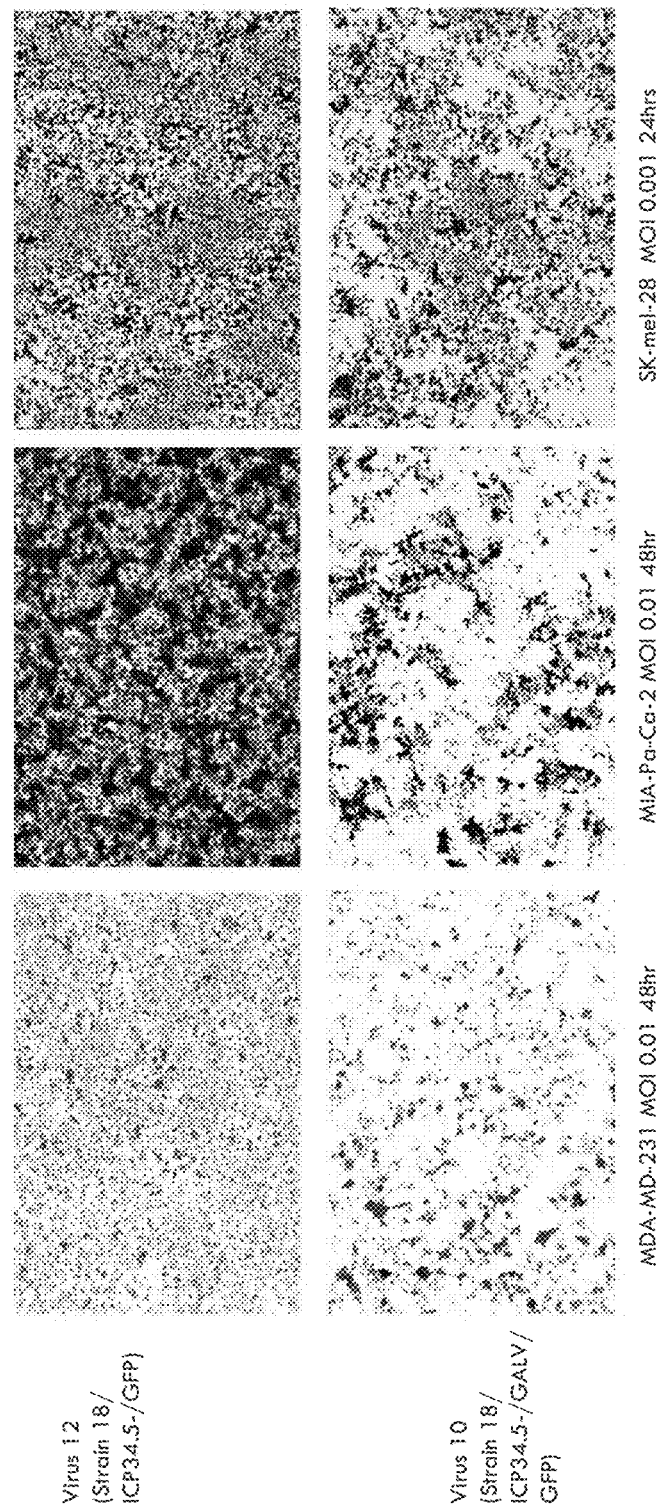

Example 7. A Virus of the Invention Modified for Oncolytic Use and Expressing a Fusogenic Glycoprotein Shows Enhanced Tumor Cell Killing In Vitro as Compared to a Virus which does not Express a Fusogenic Glycoprotein Virus 10 (see FIGS. 4A-4F), based on clinical Strain RH018A in which ICP34.5 is deleted and which expresses GALVR- and GFP, was compared in vitro to a virus which expresses only GFP Virus 12). Virus 10 showed enhanced killing on a panel of human tumor cell lines as compared to Virus 12, as shown in FIGS. 7A-7B.

Figure 8A:
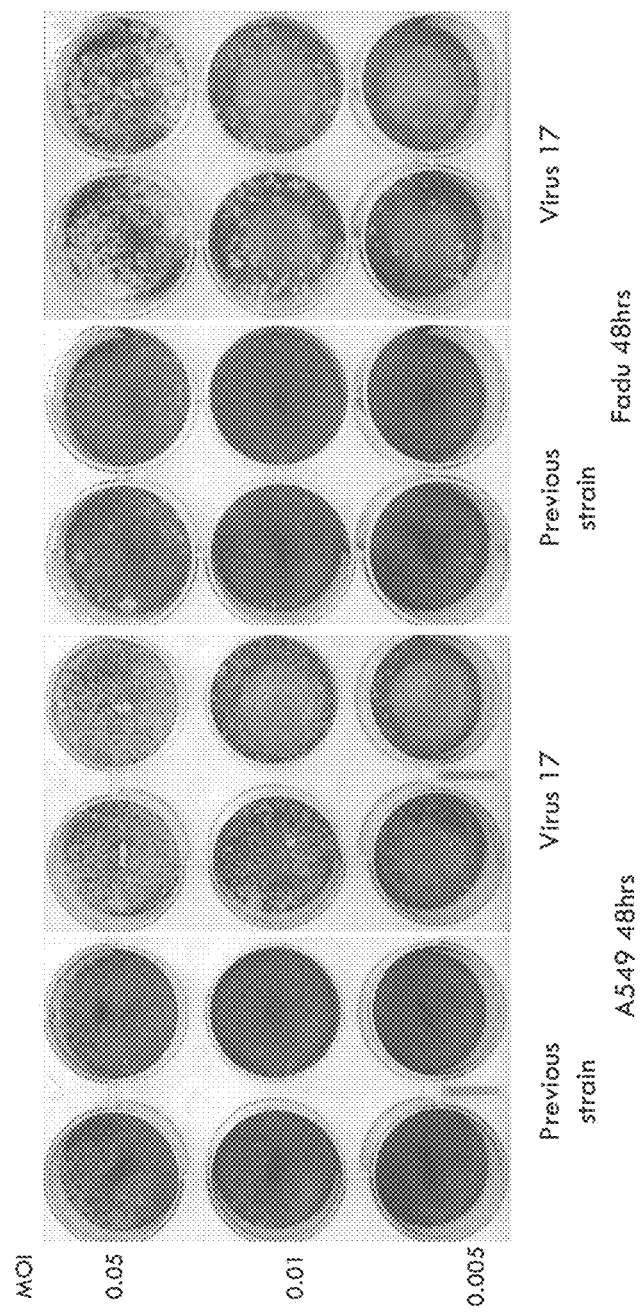
FIGS. 8A-8B is a comparison between the cell-killing abilities of strain RH018A in which ICP34.5 and ICP47 are deleted and which expresses GALVR- and GM-CSF (virus 17) with a prior art strain with the same modifications as determined by crystal violet staining in four cell lines.
Figure 8B:
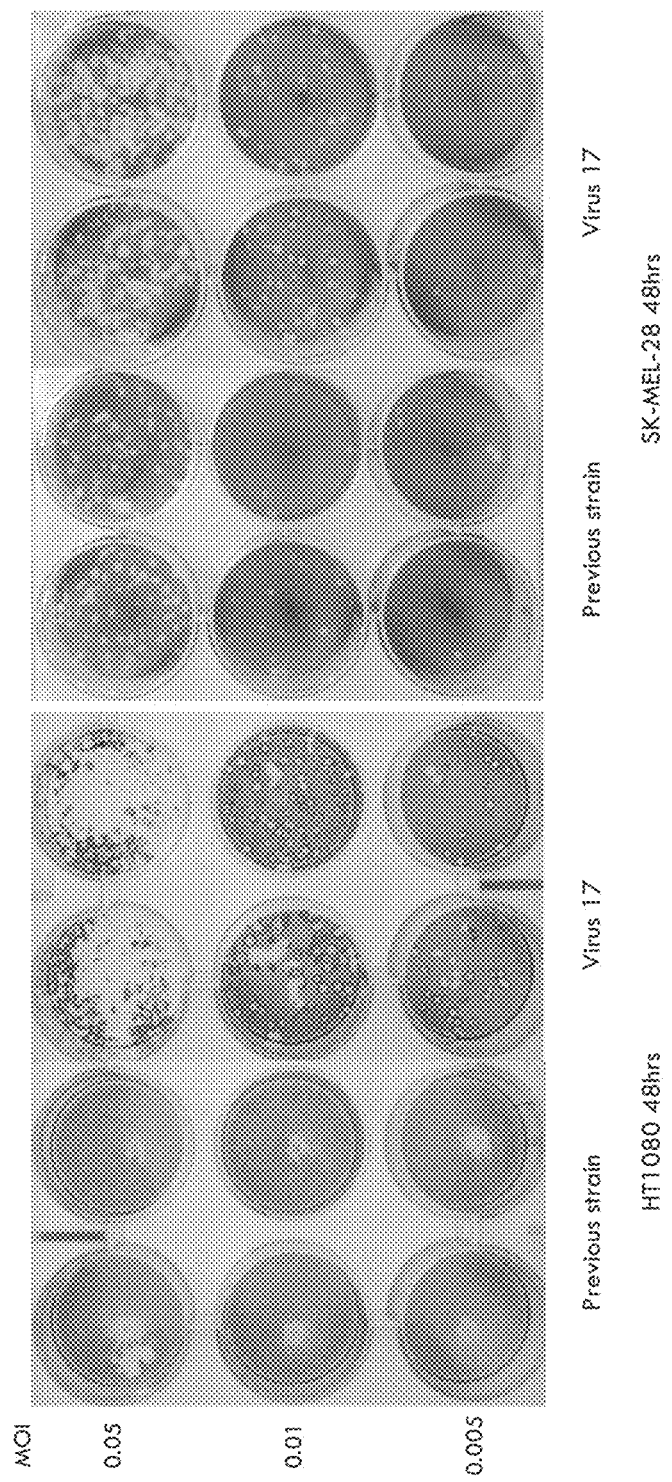

Example 8. A Virus of the Invention Modified for Oncolytic Use Shows Enhanced Tumor Cell Killing as Compared to a Similarly Modified Virus which is not of the Invention Virus 17 (see FIGS. 4A-4F), based on clinical Strain RH018A in which ICP34.5 and ICP47 are deleted and which expresses GALVR- and GM-CSF, was compared in vitro to a known virus which was also deleted for ICP34.5 and ICP47 but which was not derived from a strain of the invention and which expresses only GM-CSF. Virus 17 showed enhanced killing on a panel of human tumor cell lines as compared to the previous virus, as shown in FIGS. 8A-8B.

Figure 9:
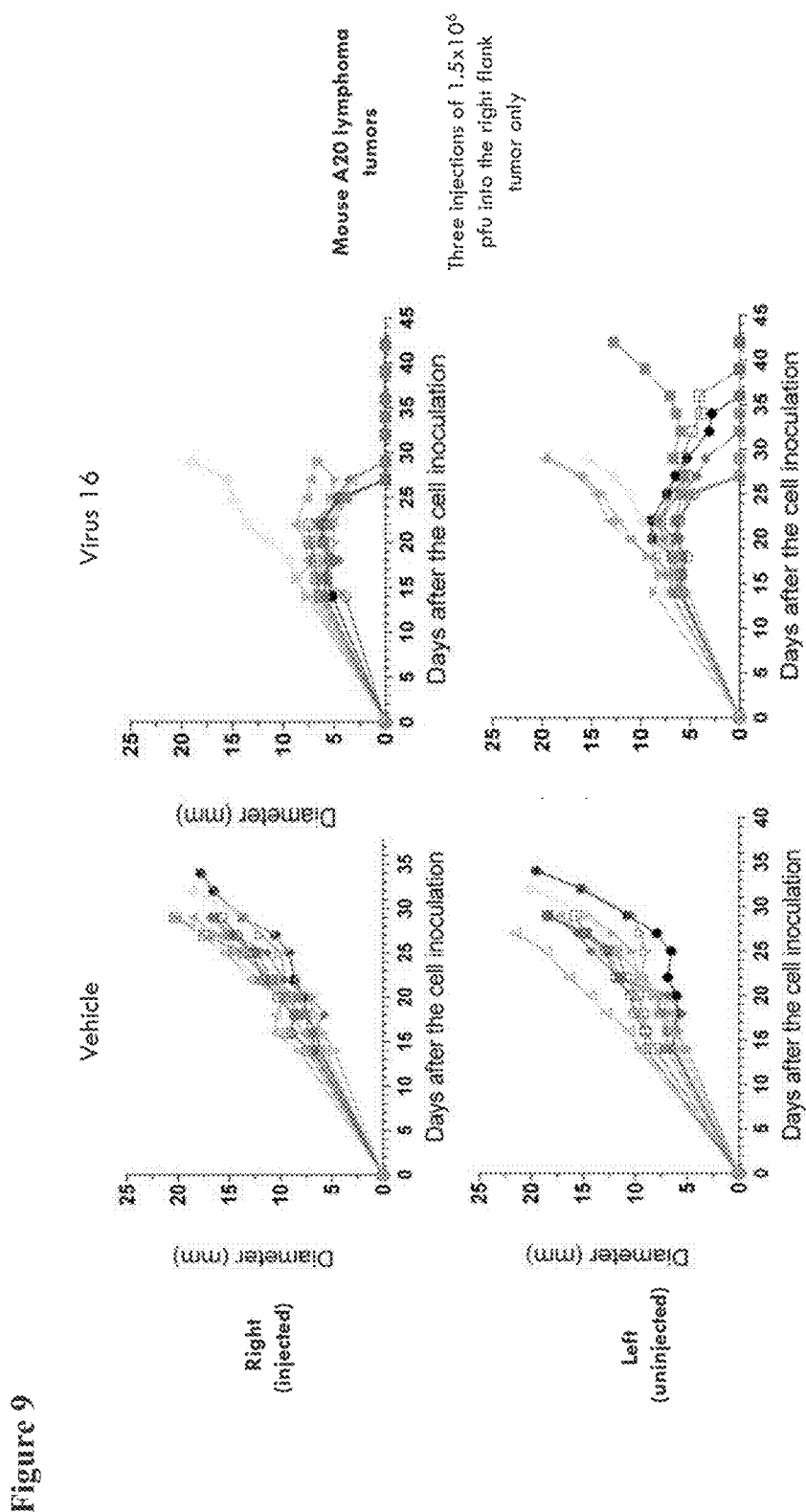
FIG. 9 shows the effectiveness of Virus 16 (ICP34.5 and ICP47 deleted expressing GALVR- and mGM-CSF) in treating mice harbouring A20 lymphoma tumors in both flanks. Tumors on the right flanks were injected with the virus or vehicle and the effects on tumor size was observed for 30 days. The virus was effective against both injected tumors and non-injected tumors.

Example 9. A Virus of the Invention Modified for Oncolytic Use Effectively Treats Mouse Tumors In Vivo Virus 16 was tested in mice harboring A20 lymphoma tumors in the left and right flanks. One million tumor cells were first implanted in both flanks of Balb/c mice and tumors allowed to grow to 0.5-0.7 cm in diameter. Tumors on the right flank were then injected 3 times (every other day) with either vehicle (10 mice) or 5×10exp6 pfu of Virus 16 (10 mice), and effects on tumor size observed for a further 30 days. This demonstrated that both injected and uninjected tumors were effectively treated with Virus 16 (see FIG. 9).

Example 10. The Effect of the Combined Expression of a Fusogenic Protein and an Immune Stimulatory Molecule from an Oncolytic Virus of the Invention in a Rat Tumor Model The GALV R- protein causes cell to cell fusion in human cells but not in mouse cells. However, GALV R- does cause fusion in rat cells.

The utility of the invention was further demonstrated by administering 9L cells into the flanks of Fischer 344 rats and allowing the 9L tumors to grow to approximately 0.5 cm in diameter.

The following treatments were then administered to groups of rats (ten per group), into one flank only of each rat three times per week for three weeks:
  50 μl of vehicle;
  50 μl of $10^7$ pfu/ml of Virus 19 (expresses mGM-CSF but not GALV R-);
  50 μl of $10^7$ pfu/ml of Virus 16 (expresses both mouse GM-CSF and GALV-R-).

Figure 10:
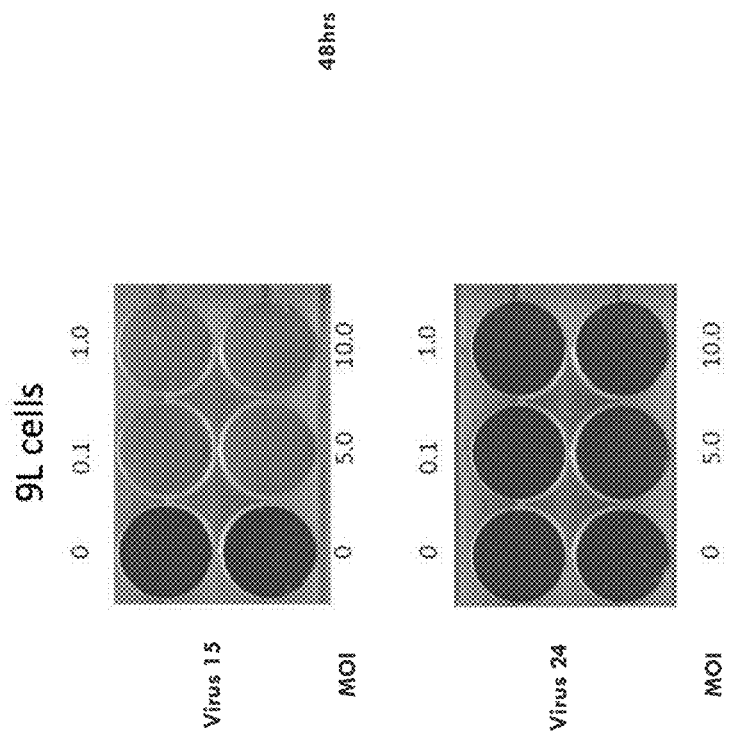
FIG. 10 demonstrates the effects of Virus 15 (ICP34.5 and ICP47 deleted expressing GALVR- and GFP) and Virus 24 (ICP34.5 and ICP47 deleted expressing GFP) on rat 9L cells in vitro as assessed by crystal violet staining. The virus expressing GALV (Virus 15) showed enhanced killing of rat 9L cells in vitro as compared to a virus which does not express GALV (Virus 24).
Figure 15:
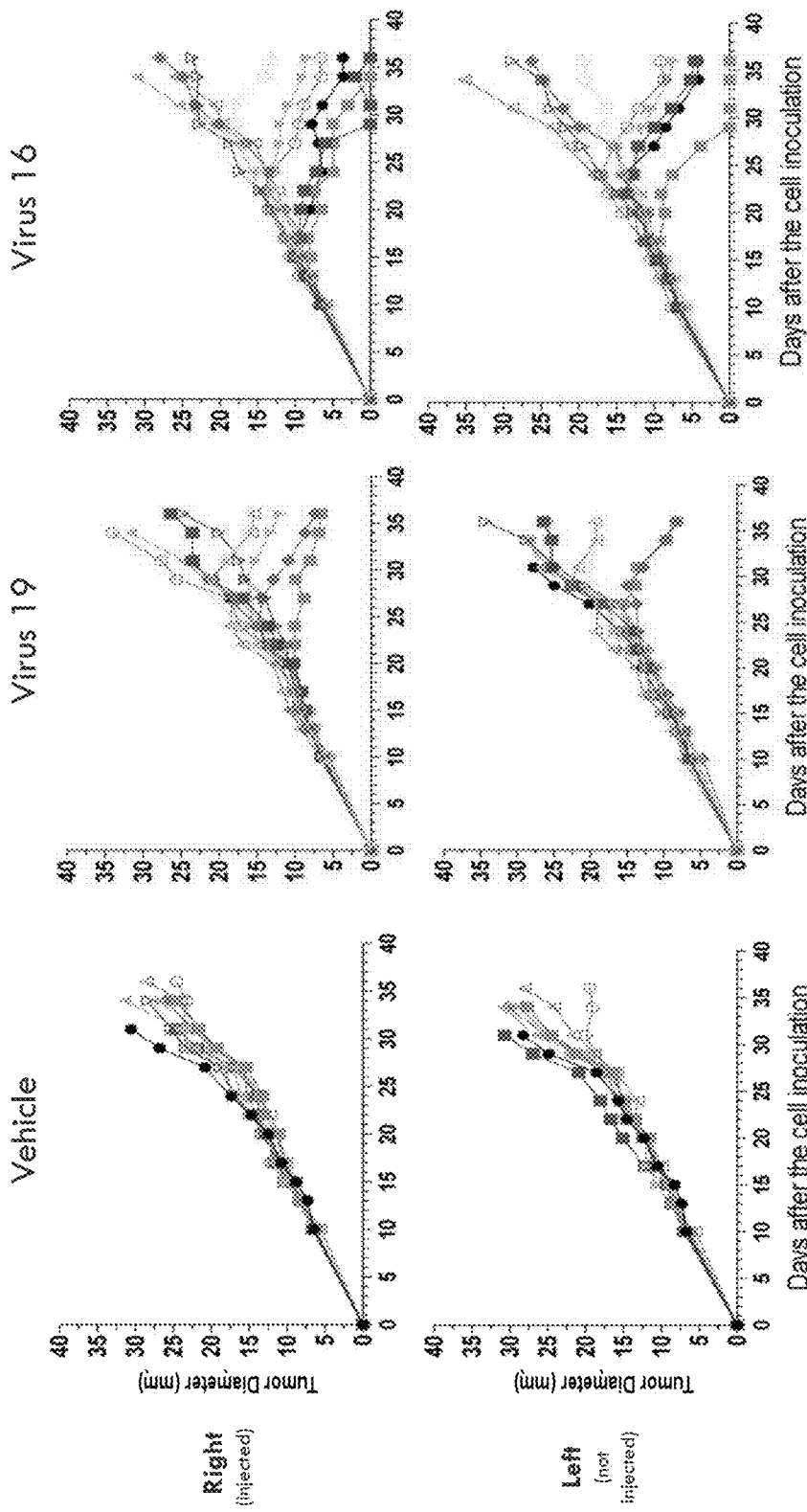
FIG. 15 demonstrates the effects of viruses of the invention expressing GALVR- on 9L cells in the flanks of Fischer 344 rats. The following treatments were administered to groups of rats (ten per group), into one flank of each rat only three times per week for three weeks: 50 µl of vehicle; 50 µl of 10$^7$ pfu/ml of Virus 19 (expresses mGM-CSF but not GALV R-); or 50 µl of 10$^7$ pfu/ml of Virus 16 (expresses both mouse GM-CSF and GALV-R-). Effects on tumor growth were then observed for a further 30 days. Superior tumor control and shrinkage was observed with the virus expressing GM-CSF and GALV-R- as compared to the virus expressing GM-CSF alone.

Effects on tumor growth were then observed for a further ≈30 days. This demonstrated superior tumor control and shrinkage with the virus expressing GALV-R- in both injected and uninjected tumors, demonstrating improved systemic effects. This is shown in FIG. 15. FIG. 10 shows that a virus expressing GALV (Virus 15) also shows enhanced killing of rat 91 cells in vitro as compared to a virus which does not express GALV (Virus 24).

Figure 11A:
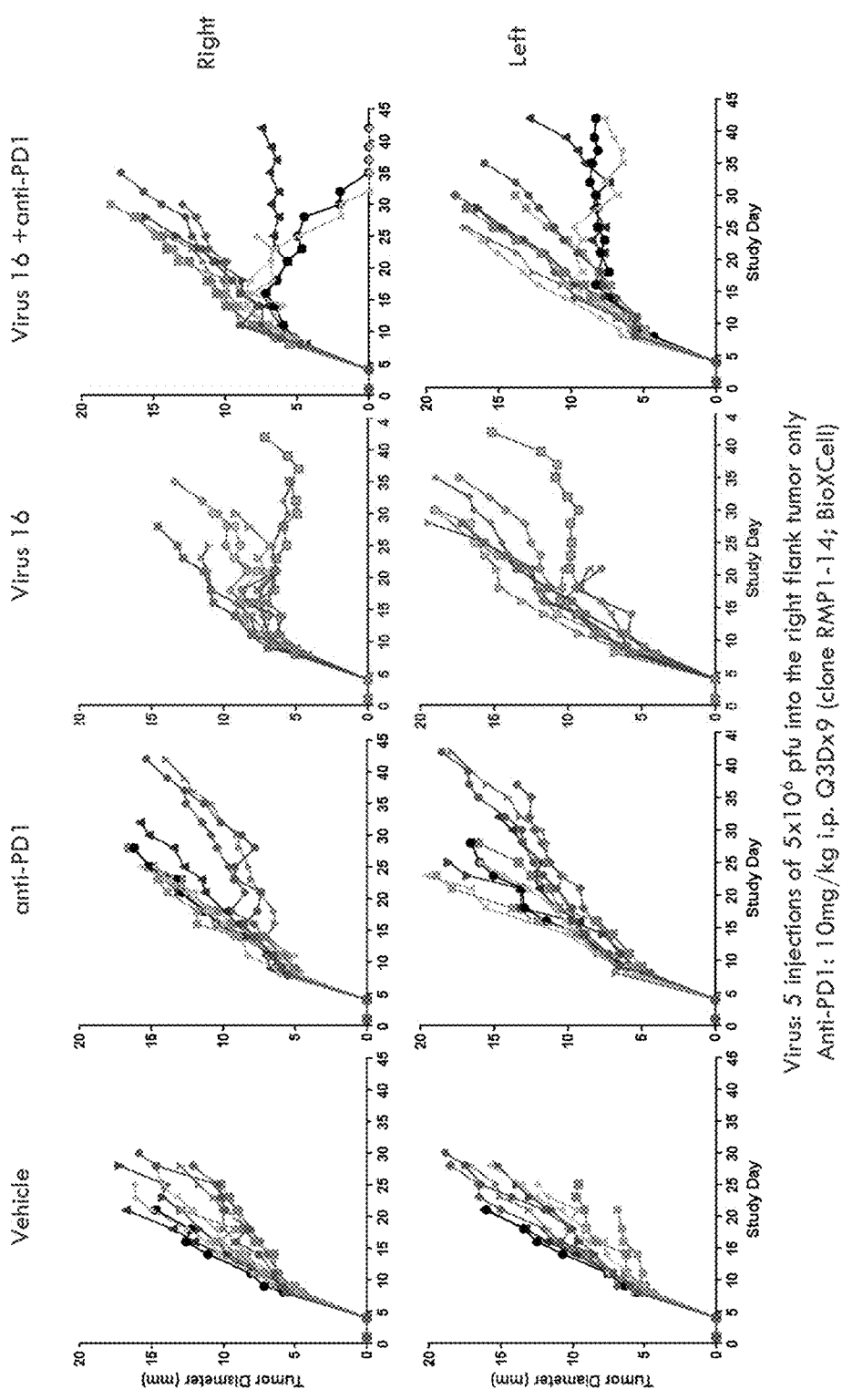
Figure 11B:
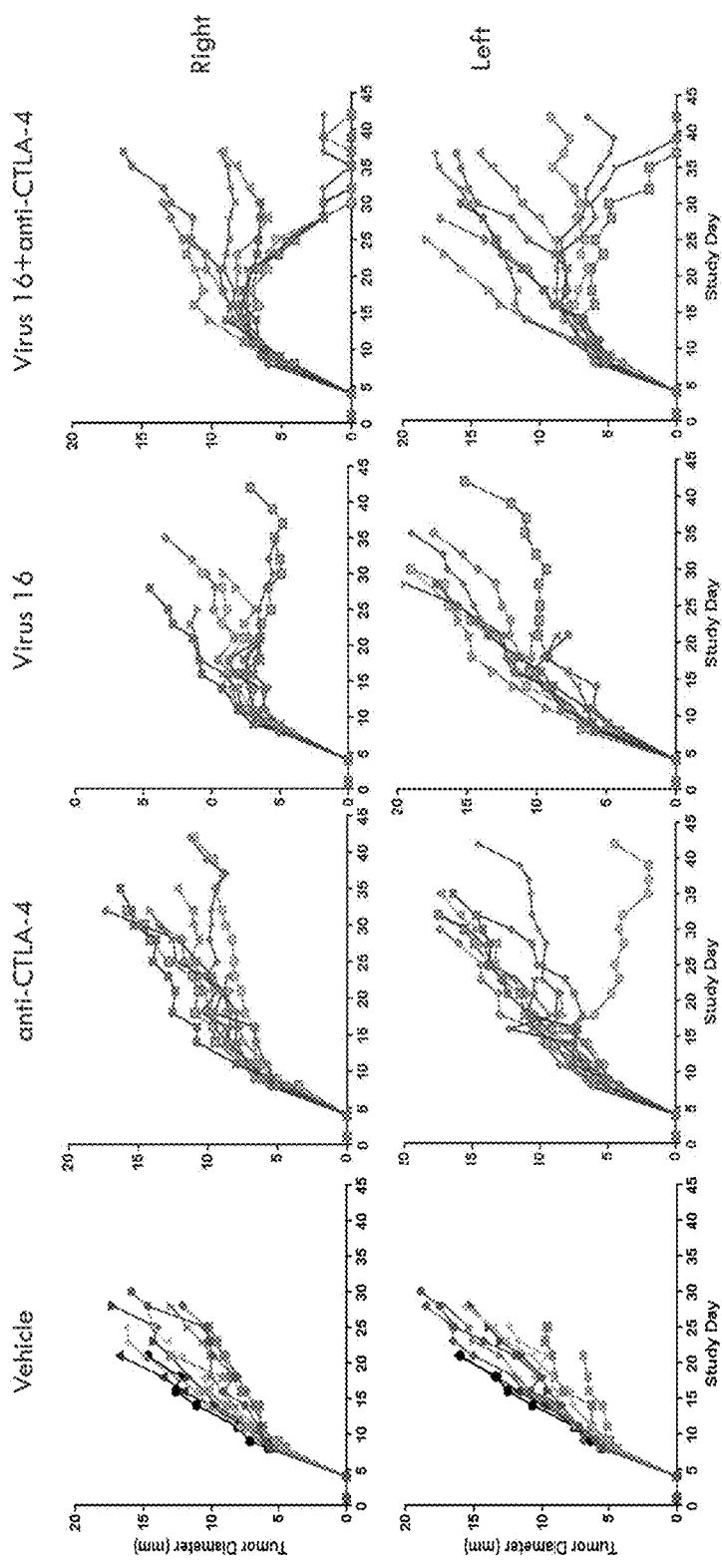
Figure 12A:
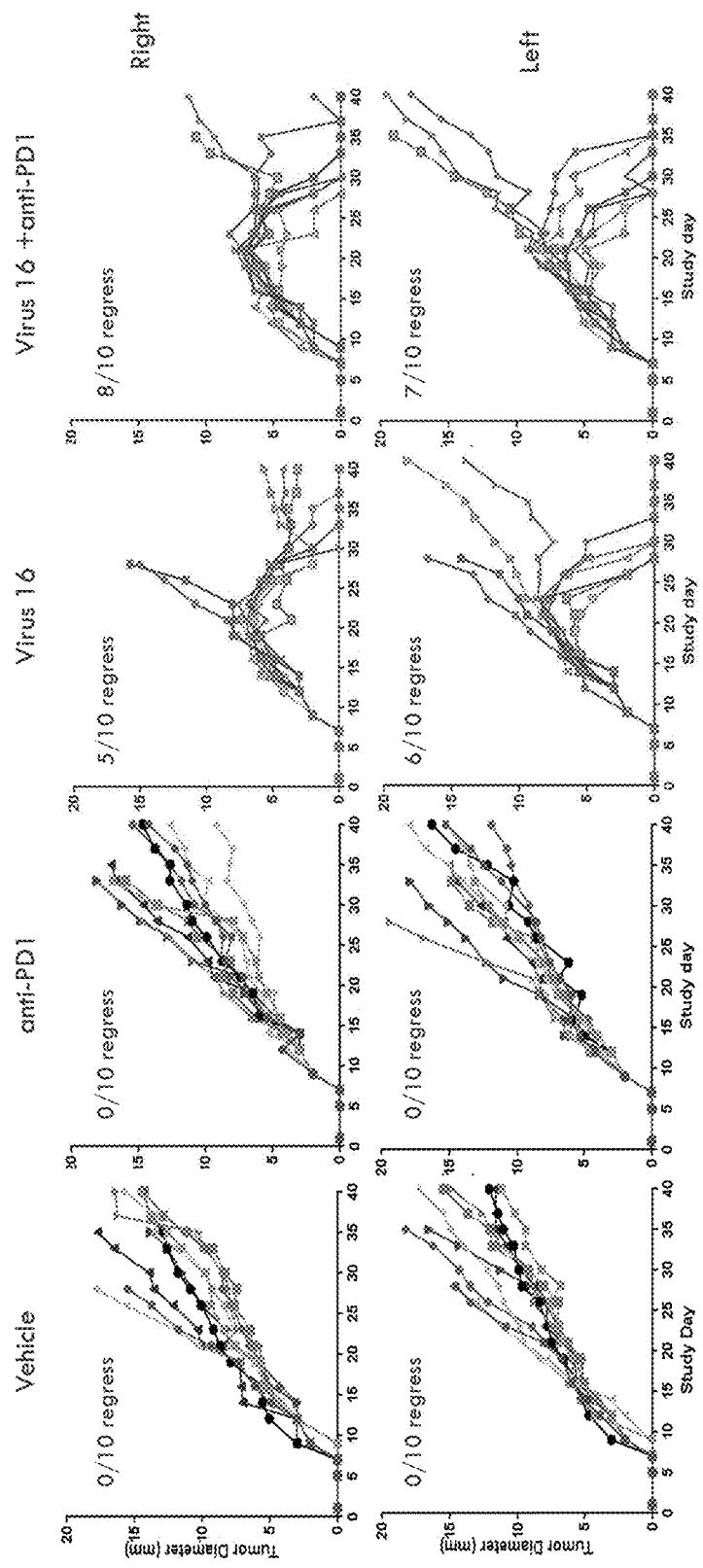
FIGS. 12A-12D shows the enhanced anti-tumor activity of Virus 16 in combination with immune checkpoint blockade in mouse A20 tumors in both flanks of Balb/c mice as compared to either virus alone or checkpoint blockade alone (anti-PD1).
Figure 12B:
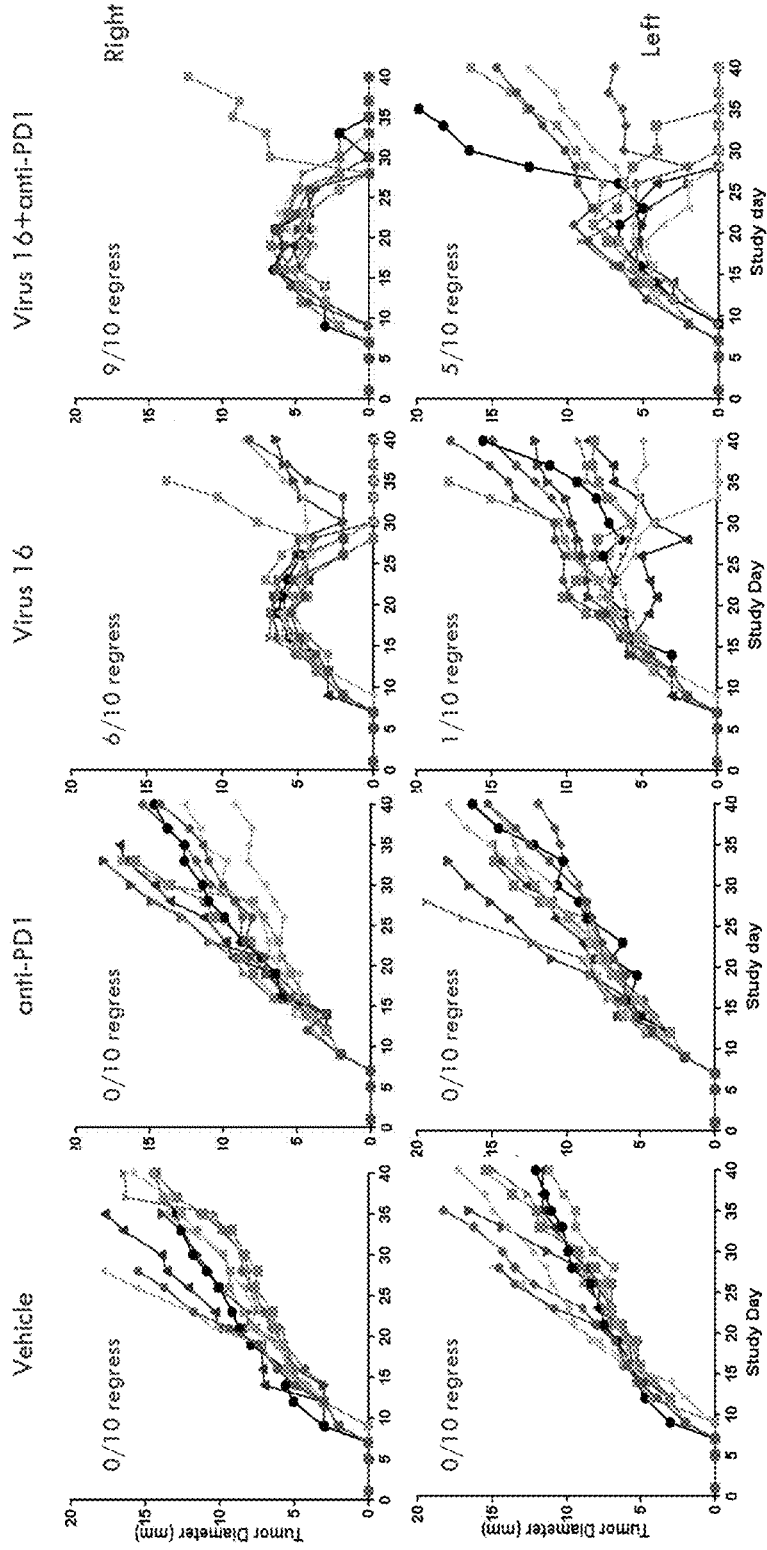
Figure 12C:
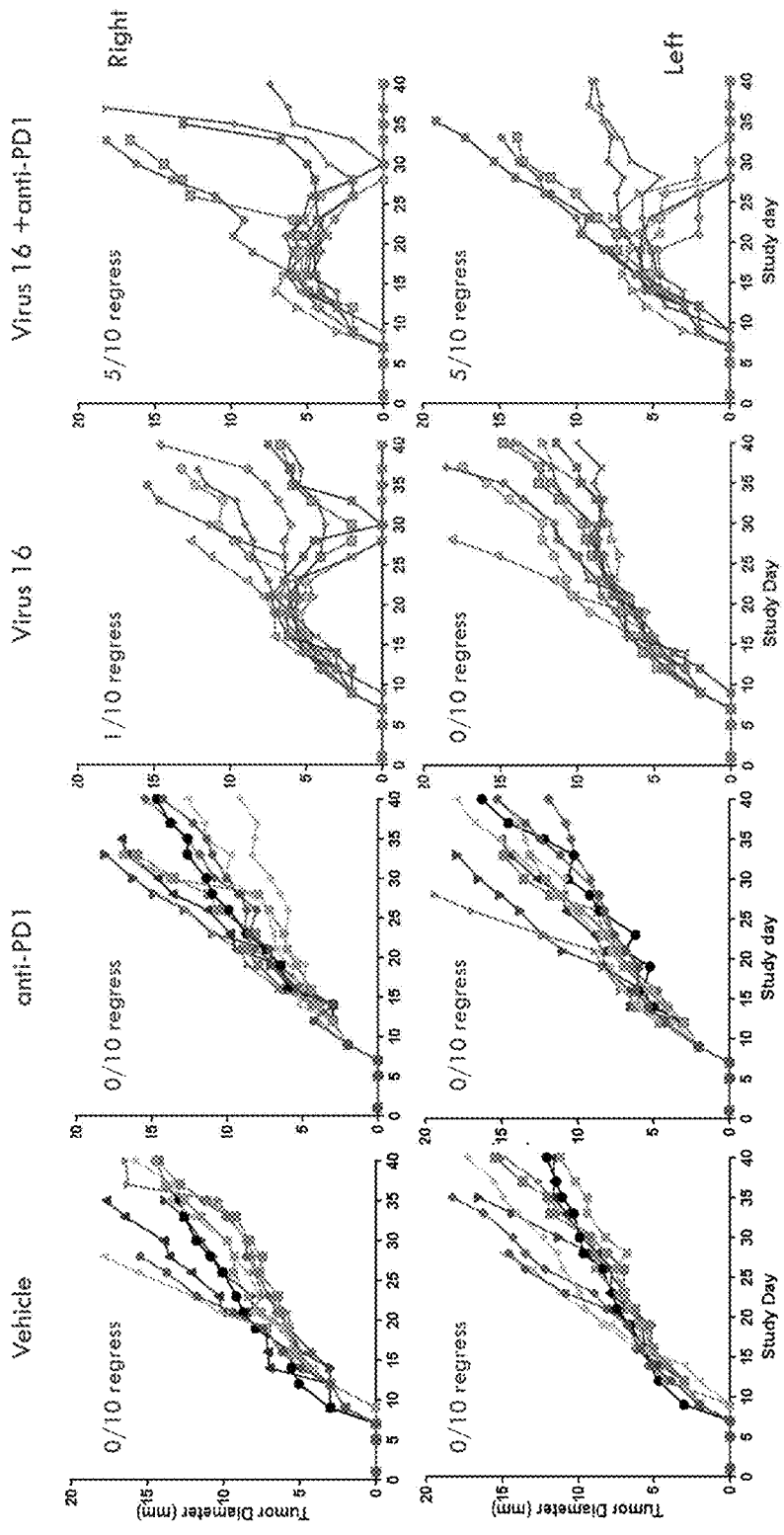
Figure 12D:
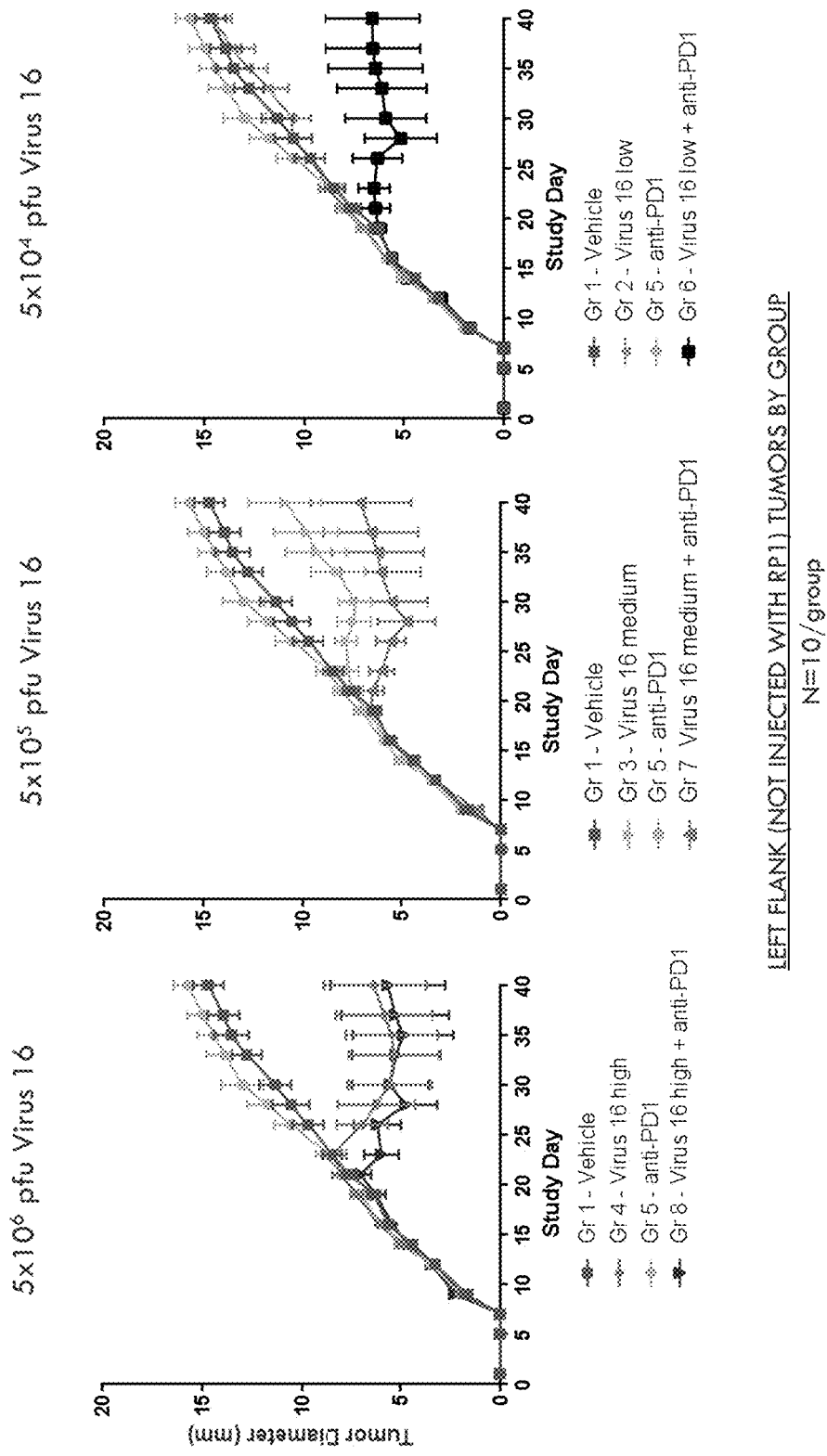

Example 11. A Virus of the Invention Modified for Oncolytic Use is Synergistic with Immune Checkpoint Blockade in Mouse Tumor Models Virus 16 was tested in mice harboring CT26 tumors in the left and right flanks. One million tumor cells were first implanted in both flanks of Balb/c mice and tumors allowed to grow to 0.5-0.6 cm in diameter.
  Groups of 10 mice were then treated with:
  Vehicle (3 injections into right flank tumors every other day);
  5×10exp6 pfu of Virus 16 injected in the right flank tumor every other day;
  anti-mouse PD1 alone (10 mg/kg i.p. every three days, BioXCell clone RMP1-14);
  anti-mouse CTLA-4 (3 mg/Kg i.p every three days, BioXCell clone 9D9);
  anti-mouse PD1 together with Virus 16;
  anti-mouse CTLA4 together with Virus 16;
  1-methyl trypotophan (IDO inhibitor (5 mg/ml in drinking water));
  anti-mouse PD1 together with 1-methyl trypotophan;
  anti-mouse PD1 together with 1-methyl trypotophan and Virus 16;

Effects on tumor size were observed for a further 30 days. A greater tumor reduction in animals treated with combinations of virus and checkpoint blockade was demonstrated than in animals treated with the single treatment groups (see FIGS. 11A-11C). Enhanced tumor reduction with Virus 16 together with both anti-PD1 and IDO inhibition was also demonstrated as compared to Virus 16 together with only anti-PD1 (see FIGS. 11A-11C).

Enhanced activity of Virus 16 in combination with immune checkpoint blockade was also seen in A20 tumors (FIGS. 12A-12D).

Example 12. The Effect of the Expression of a Fusogenic Protein Front an Oncolytic Virus of the Invention in Human Xenograft Models in Immune Deficient Mice The GALV R- protein causes cell to cell fusion in human cells but not in mouse cells. However, human xenograft tumors grown in immune deficient mice can be used to assess the effects of GALV expression on anti-tumor efficacy.

The utility of the invention was therefore further demonstrated by administering A549 human lung cancer cells into the flanks of nude mice and allowing the tumors to grow to approximately 0.5 cm in diameter.

The following treatments were then administered to groups of mice (ten per group), into tumor containing flank of each mouse three times over one week:
  50 μl of vehicle;
  50 μl of $10^7$ pfu/ml of Virus 16 (expresses both mouse GM-CSF and GALV-R-);
  50 μl of $10^6$ pfu/ml of Virus 16;
  50 μl of $10^5$ pfu/ml of Virus 16;
  50 μl of $10^7$ pfu/ml of Virus 19 (expresses only mouse GM-CSF);
  50 μl of $10^6$ pfu/ml of Virus 19;
  50 μl of $10^5$ pfu/ml of Virus 19.

Figure 14:
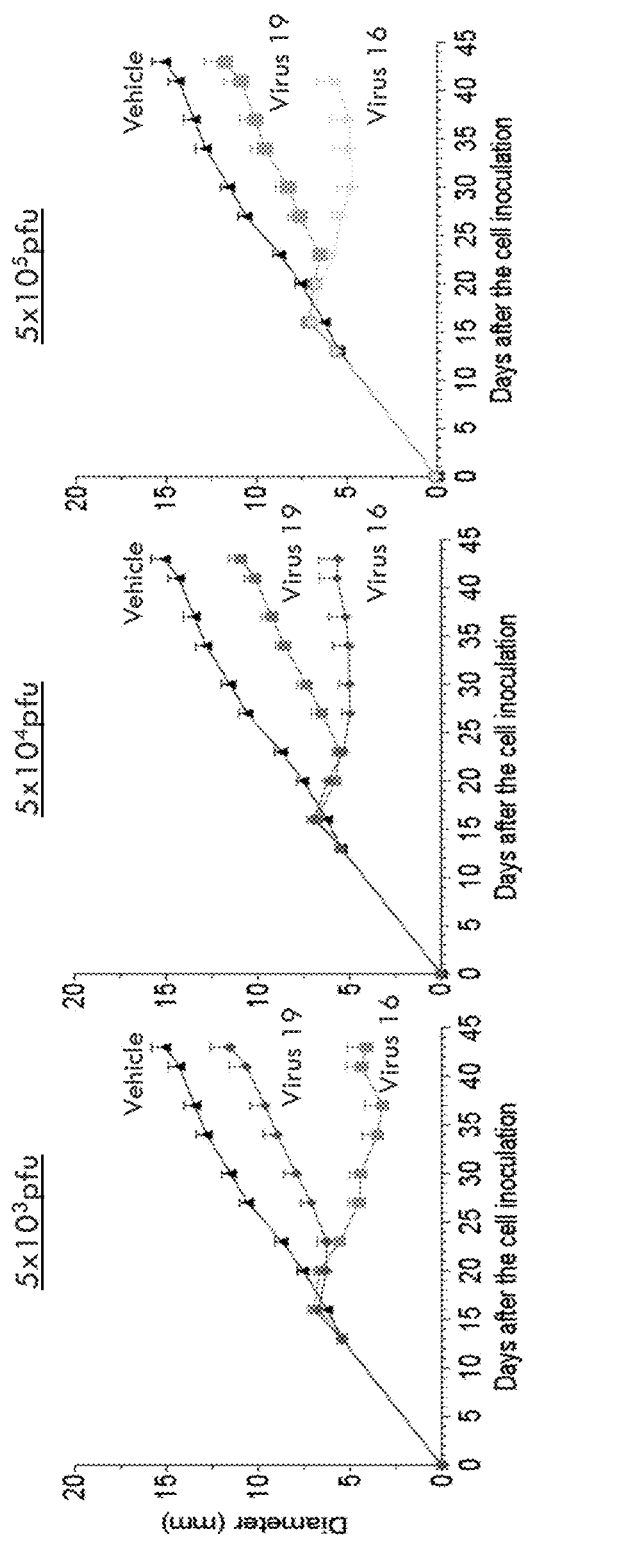
FIG. 14 shows anti-tumor effects of Virus 16 and Virus 19 in a human xenograft model (A549). There were three injections of Virus 16, Virus 19 or of vehicle over one week at three different dose levels (N=10/group). The doses of the viruses used is indicated. The anti-tumor effects of Virus 16 which expresses GALV were better than those of Virus 19 which does not express GALV.

Effects on tumor growth were then observed for a further ≈30 days. This experiment demonstrated superior tumor control and shrinkage with the virus expressing GALV-R- in both tumor models (see FIG. 14).

Figure 13:
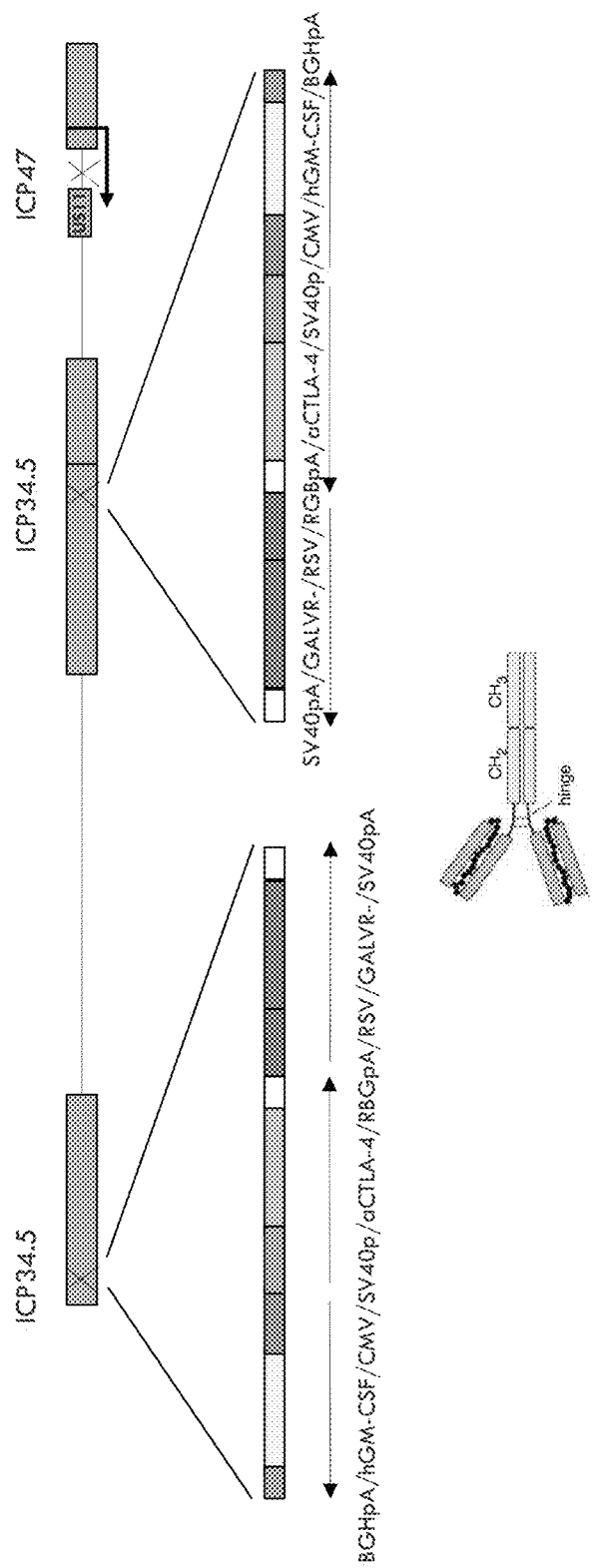
FIG. 13 shows the structure of ICP34.5 and ICP47 deleted viruses expressing GALVR-, GM-CSF and codon optimized anti-mouse or anti-human CTLA-4 antibody constructs (secreted scFv molecules linked to human or mouse IgG1 Fc regions). The scFvs contain the linked ([G$_4$S]$_3$) light and heavy variable chains from antibody 9D9 (US2011044953; mouse version) and from ipilimumab (US20150283234; human version). The resulting structure of the CTLA-4 inhibitor is also shown.
Figure 16:
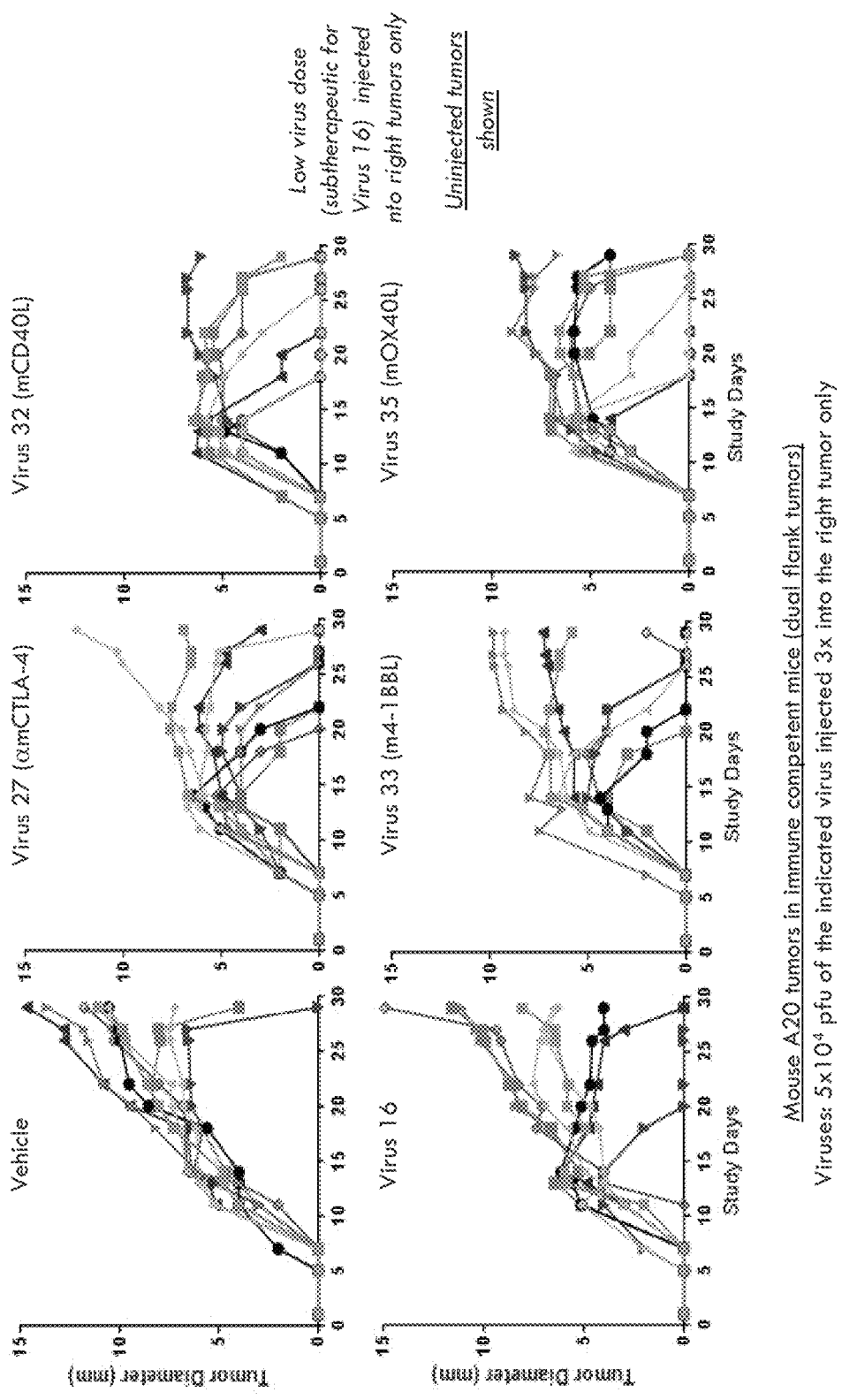
FIG. 16 shows the anti-tumor effects of viruses expressing anti-mCTLA-4 (virus 27), mCD40L (virus 32), mOX40L (virus 35), m4-2BBL (virus 33), each also with mGM-CSF and GALV-R- compared to virus 16 (expresses GALV and mGM-CSF).

Example 13. Expression of Two Immune Stimulatory Molecules from a Virus Expressing a Fusogenic Protein Viruses similar to the GALV-R- and mGM-CSF expressing virus described above (Virus 16) were constructed, but additionally expressing mouse versions of CD40L (virus 32), ICOSL (virus 36), OX40L (virus 35), 4-1BBL (virus 33) and GITRL (virus 34). Here, instead of using a plasmid containing ICP34.5 flanking regions and an expression cassette comprising GM-CSF and GALV-R- driven by a CMV and an RSV promoter, a plasmid containing ICP34.5 flanking regions and an expression cassette comprising GM-CSF, GALV and the additional proteins driven by a CMV, an RSV and an MMLV promoter respectively were used for recombination with a virus containing GM-CSF, GALV and GFP inserted into ICP34.5. Non-GFP expressing plaques were again selected. Correct insertion was confirmed by PCR, and expression by western blotting and/or ELISA for the additional inserted gene. These viruses are shown in FIGS. 5A-5F. Similarly, viruses expressing anti-mouse and anti-human CTLA-4 in addition to GALV and mGM-CSF were also constructed (Viruses 27 and 31 in FIGS. 5A-5F and see also FIG. 13). Effects of viruses expressing anti-mouse CTLA-4 (virus 27), mCD40L (virus 32), m4-1BBL (virus 33) or mOX40L (virus 35) in addition to mGM-CSF and GALVR- in vivo is shown in FIG. 16 which showed enhanced activity in A20 tumors as compared to virus 16 (expresses mGM-CSF and GALVR-). In these experiments tumors were induced in both flanks of mice, and virus or vehicle injected only into the right flank tumor. The dose of virus used was 5×$10^4$ pfu (50 ul of 1×$10^6$ pfu/ml in each case), given three times over one week. This dose level of virus is subtherapeutic for uninjected tumors for virus 16, which allows the benefits of the delivery of the additional molecules encoded by viruses 27, 32, 33 and 35 to clearly be seen.

Deposit Information

The following HSV1 strains were deposited at the ECACC, Culture Collections, Public Health England, Porton Down, Salisbury, SP4 0JG, United Kingdom on 19 Dec. 2016 by Replimune Limited and were allocated the indicated provisional accession numbers:
  RH004A—Provisional Accession Number 16121902
  RH015A—Provisional Accession Number 16121903
  RH018A—Provisional Accession Number 16121904
  RH021A—Provisional Accession Number 16121905
  RH023A—Provisional Accession Number 16121906
  RH031A—Provisional Accession Number 16121907
  RH040B—Provisional Accession Number 16121908
  RH047A—Provisional Accession Number 16121909.

The invention claimed is:

1. A method for treating injected and non-injected solid tumors in a subject in need thereof, the method comprising: administering to the subject an effective amount of an oncolytic herpes virus comprising inserted in its genome (i) a heterologous gene encoding granulocyte-macrophage colony-stimulating factor (GM-CSF) and (ii) a heterologous gene encoding an anti-cytotoxic T-lymphocyte-associated antigen 4 (CTLA-4) antibody, wherein the oncolytic virus is administered by intra-tumoral injection, wherein the administration induces the regression of injected and non-injected solid tumors, and wherein injected solid tumors are solid tumors into which the oncolytic virus is injected, and non-injected solid tumors are solid tumors which are not injected with the oncolytic virus.

2. The method of claim 1, wherein the solid tumor is an adenocarcinoma, carcinoma, melanoma, or sarcoma.

3. The method of claim 1, comprising administering multiple doses of $10^4$ to $10^{10}$ pfu of the oncolytic virus to the subject.

4. The method of claim 3, wherein the multiple doses of the oncolytic virus are administered to the subject between 3 days to 3 weeks apart.

5. The method of claim 1, wherein the method further comprises administering an anti-programmed cell death ligand 1 (PD1) antibody to the subject.

6. The method of claim 5, comprising administering the oncolytic virus to the subject prior to administering the anti-PD1 antibody to the subject.

7. The method of claim 6, comprising administering the oncolytic virus to the subject once prior to administering the anti-PD1 antibody to the subject.

8. The method of claim 6, comprising administering the oncolytic virus multiple times to the subject prior to administering the anti-PD1 antibody to the subject.

9. The method of claim 5, comprising administering the oncolytic virus and anti-PD1 antibody to the subject concurrently.

10. The method of claim 1, wherein the herpes virus is HSV-1.

11. A method for inducing a systemic anti-tumor response to regress solid tumors in a subject in need thereof, the method comprising: administering to the subject an effective amount of an oncolytic herpes virus comprising inserted in its genome (i) a heterologous gene encoding GM-CSF and (ii) a heterologous gene encoding an anti-CTLA-4 antibody wherein the oncolytic virus is administered by intra-tumoral injection, wherein the administration induces the systemic anti-tumor response in the subject such that injected and non-injected solid tumors are regressed, and wherein injected solid tumors are solid tumors into which the oncolytic virus is injected, and non-injected solid tumors are solid tumors which are not injected with the oncolytic virus.

12. The method of claim 11, wherein the solid tumor is an adenocarcinoma, carcinoma, melanoma, or sarcoma.

13. The method of claim 11, comprising administering multiple doses of $10^4$ to $10^{10}$ pfu of the oncolytic virus to the subject.

14. The method of claim 13, wherein the multiple doses of the oncolytic virus are administered to the subject between 3 days to 3 weeks apart.

15. The method of claim 11, wherein the method further comprises administering an anti-PD1 antibody to the subject.

16. The method of claim 15, comprising administering the oncolytic virus to the subject prior to administering the anti-PD1 antibody to the subject.

17. The method of claim 16, comprising administering the oncolytic virus to the subject once prior to administering the anti-PD1 antibody to the subject.

18. The method of claim 16, comprising administering the oncolytic virus multiple times to the subject prior to administering the anti-PD1 antibody to the subject.

19. The method of claim 15, comprising administering the oncolytic virus and anti-PD1 antibody to the subject concurrently.

20. The method of claim 11, wherein the herpes virus is HSV-1.

21. A method for treating one or more solid tumors in a subject in need thereof, the method comprising: administering to the subject an effective amount of an oncolytic herpes virus comprising inserted in its genome (i) a heterologous gene encoding GM-CSF and (ii) a heterologous gene encoding an anti-CTLA-4 antibody, wherein the oncolytic virus is administered by injection into a solid tumor, and wherein the administration induces regression of the solid tumors in the subject.

22. The method of claim 21, wherein the solid tumor is an adenocarcinoma, carcinoma, melanoma, or sarcoma.

23. The method of claim 21, comprising administering multiple doses of $10^4$ to $10^{10}$ pfu of the oncolytic virus to the subject.

24. The method of claim 23, wherein the multiple doses of the oncolytic virus are administered to the subject between 3 days to 3 weeks apart.

25. The method of claim 21, wherein the method further comprises administering an anti-PD1 antibody to the subject.

26. The method of claim 25, comprising administering the oncolytic virus to the subject prior to administering the anti-PD1 antibody to the subject.

27. The method of claim 26, comprising administering the oncolytic virus to the subject once prior to administering the anti-PD1 antibody to the subject.

28. The method of claim 26, comprising administering the oncolytic virus multiple times to the subject prior to administering the anti-PD1 antibody to the subject.

29. The method of claim 25, comprising administering the oncolytic virus and anti-PD1 antibody to the subject concurrently.

30. The method of claim 21, wherein the herpes virus is HSV-1.

* * * * *

SEQUENCE LISTING

```
Sequence total quantity: 45
SEQ ID NO: 1                moltype = DNA  length = 426
FEATURE                     Location/Qualifiers
source                      1..426
                            mol_type = other DNA
                            organism = Mus musculus
SEQUENCE: 1
atgtggctgc agaatttact tttcctgggc attgtggtct acagcctctc agcacccacc   60
cgctcaccca tcactgtcac ccggccttgg aagcatgtag aggccatcaa agaagccctg  120
aacctcctgg atgacatgcc tgtcacattg aatgaagagg tagaagtcgt ctctaacgag  180
ttctccttca agaagctaac atgtgtgcag acccgcctga agatattgga gcagggtcta  240
cggggcaatt tcaccaaaact caagggcgct tgaacatga cagccagcta ctaccagaca  300
tactgccccc caactccgga aacggactgt gaaacacaag ttaccaccta tgcggatttc  360
atagacagcc ttaaaacctt tctgactgat atcccctttg aatgcaaaaa accagtccaa  420
aaatga                                                              426

SEQ ID NO: 2                moltype = DNA  length = 426
FEATURE                     Location/Qualifiers
source                      1..426
                            mol_type = other DNA
                            organism = Mus musculus
SEQUENCE: 2
atgtggctcc agaacctcct cttcctcggt atcgtcgtgt attcactctc cgcacctact   60
cgctcaccta tcactgtcac cagaccctgg aagcacgtgg aggccatcaa ggaggctctg  120
aacctgctgg acgatatgcc agtgaccctg aacgaggagg tggaggtggt gagcaacgag  180
ttctccttta agaagctgac ctgcgtgcag acaaggctga agatcttcga gcagggcctg  240
agaggaaaact ttaccaagct gaagggcgcc ctgaacatga ccgcttctta ctaccagaca  300
tactgccccc ctaccccccga gacagactgt gagacacagg tgaccacata cgccgacttc  360
attgatagcc tgaaaacatt cctgaccgac attccatttg agtgtaagaa gcccgtccag  420
aagtaa                                                              426

SEQ ID NO: 3                moltype = DNA  length = 435
FEATURE                     Location/Qualifiers
source                      1..435
                            mol_type = other DNA
                            organism = Homo sapiens
SEQUENCE: 3
atgtggctgc agagcctgct gctcttgggc actgtggcct gcagcatctc tgcacccgcc   60
cgctcgccca gccccagcac gcagccctgg gagcatgtga atgccatcca ggaggcccgg  120
cgtctcctga acctgagtag agacactgct gctgagatga tgaaacagt gcaaagtcatc  180
tcagaaatgt ttgacctcca ggagccgacc tgcctacaga cccgcctgga gctgtacaag  240
cagggcctgc ggggcagcct caccaagctc aagggcccct tgaccatgat ggccagccac  300
tacaagcagc actgccctcc aaccccggaa acttcctgtg caacccagat tatcacctt  360
gaaagtttca agagaacct gaaggactt ctgcttgtca tccccttgat gctgctggag  420
ccagtccagg agtga                                                   435

SEQ ID NO: 4                moltype = DNA  length = 435
FEATURE                     Location/Qualifiers
source                      1..435
                            mol_type = other DNA
                            organism = Homo sapiens
SEQUENCE: 4
atgtggctgc agtccctgct gctgctgggc accgtcgcct gttctatttc cgcacccgca   60
aggtcaccaa gtccatctac tcagccttgg gagcacgtga acgcaatcca ggaggcacgg  120
cggctgctga acctgagccg ggacaccgcc gccgagatga cgagacagt ggaagtgatc  180
agcgagatgt tcgatctgca ggagcccacc tgcctgcaga caaggctgga gctgtacaag  240
cagggcctgc gcggctctct gaccaagctg aagggcccac tgacaatgat ggccagccac  300
tataagcagc actgcccccc taccccgag acaagctgtg ccacccagat catcacattc  360
gagtccttta aggagaacct gaaggatttt ctgctggtca ttccatttga ttgttgggag  420
cccgtccagg agtaa                                                   435

SEQ ID NO: 5                moltype = AA  length = 141
FEATURE                     Location/Qualifiers
source                      1..141
                            mol_type = protein
                            organism = Mus musculus
SEQUENCE: 5
MWLQNLLFLG IVVYSLSAPT RSPITVTRPW KHVEAIKEAL NLLDDMPVTL NEEVEVVSNE   60
FSFKKLTCVQ TRLKIFEQGL RGNFTKLKGA LNMTASYYQT YCPPTPETDC ETQVTTYADF  120
IDSLKTFLTD IPFECKKPVQ K                                            141

SEQ ID NO: 6                moltype = AA  length = 144
FEATURE                     Location/Qualifiers
source                      1..144
                            mol_type = protein
                            organism = Homo sapiens
SEQUENCE: 6
MWLQSLLLLG TVACSISAPA RSPSPSTQPW EHVNAIQEAR RLLNLSRDTA AEMNETVEVI   60
```

```
SEMFDLQEPT CLQTRLELYK QGLRGSLTKL KGPLTMMASH YKQHCPPTPE TSCATQIITF  120
ESFKENLKDF LLVIPFDCWE PVQE                                        144

SEQ ID NO: 7            moltype = DNA  length = 2010
FEATURE                 Location/Qualifiers
source                  1..2010
                        mol_type = other DNA
                        organism = Gibbon leukemia virus
SEQUENCE: 7
atggtattgc tgcctgggtc catgcttctc acctcaaacc tgcaccacct tcggcaccag   60
atgagtcctg ggagctggaa aagactgatc atcctcttaa gctgcgtatt cggcggcggc  120
gggacgagtc tgcaaaataa gaaccccac cagcccatga ccctcacttg gcaggtactg   180
tcccaaactg gagacgttgt ctgggataca aaggcagtcc agccccttg gacttggtgg   240
cccacactta aacctgatgt atgtgccttg gcggctagtc ttgagtcctg ggatatcccg   300
ggaaccgatg tctcgtcctc taaacgagtc agacctccgg actcagacta tactgccgct   360
tataagcaaa tcacctgggg agccataggg tgcagctacc ctcgggctag gactagaatg   420
gcaagctcta ccttctacgt atgtcccgg gatggccgga cccttcaga agctagaagg    480
tgcgggggc tagaatccct atactgtaaa gaatggat gtgagaccac ggggaccggt     540
tattggctat ctaaatcctc aaagacctc ataactgtaa aatgggacca aaatagcgaa   600
tggactcaaa aatttcaaca gtgtcaccag accggctggt gtaaccccct aaaatagat   660
ttcacagaca aaggaaaatt atccaaggac tggataacgg gaaaaacctg gggattaaga   720
ttctatgtgt ctggacattc aggcgtacag ttccaccatt gcttaaaaat caccaacatg   780
ccagctgtgg cagtaggtcc tgacctcgtc cttgtggaac aaggacctcc tagaacgtcc   840
ctcgctctcc cacctcctct tcccccaagg gaagcgccac cgccatctct cccgactct   900
aactccacag ccctggcgac tagtgcacaa actcccacgg tgagaaaaac aattgttacc   960
ctaaacactc cgcctcccac cacaggcgac agacttttg atcttgtgca gggggccctc  1020
ctaaccttaa atgctaccaa cccaggggc actgagtctt gctggctttg tttggccatg  1080
ggccccctt attatgaagc aatagcctca tcaggagagg tcgcctactc caccgacctt  1140
gaccggtgcc gctgggggac ccaaggaaag ctcaccctca ctgaggtctc aggacacggg  1200
ttgtgcatag gaaaggtgcc ctttacccat cagcatctcc gcaatcagac cctatccatc  1260
aattcctccg gagaccatca gtatctgctc ccctccaacc atagctggtg ggcttgcagc  1320
actggcctca cccttgcct ctccacctca gttttaatc agactagaga tttctgtatc    1380
caggtccagc tgattcctcg catctattac tatcctgaag aagttttgtt acaggcctat   1440
gacaattctc accccaggac taaaagagag gctgtctcac ttaccctagc tgttttactg   1500
gggttgggaa tcacggcggg aataggtact ggttcaactg ccttaattaa aggacctata   1560
gacctccagc aaggcctgac aagcctccag atcgccatag atgctgacct ccgggccctc   1620
caagactcag tcagcaagtt agaggactca ctgacttccc tgtccgaggt agtgctccaa   1680
aataggagag gccttgactt gctgtttcta aaagaaggtg gcctctgtgc ggccctaaag   1740
gaagagtgct gtttttacat agaccactca ggtgcagtac gaaaaaactc                1800
aaagaaaaac tggataaaag acagttagag cgccagaaaa gccaaaactg gtatgaagga   1860
tggttcaata actccccttg gttcactacc ctgctatcaa ccatcgctgg gccctatta    1920
ctcctccttc tgttgctcat cctcgggcca tgcatcatca ataagttagt tcaattcatc   1980
aatgatagga taagtgcagt taaaatttaa                                    2010

SEQ ID NO: 8            moltype = DNA  length = 2013
FEATURE                 Location/Qualifiers
source                  1..2013
                        mol_type = other DNA
                        organism = Gibbon leukemia virus
SEQUENCE: 8
accatggtcc tgctgcctgg gtctatgctg ctgacttcta acctgcacca cctgcgacac   60
cagatgtctc ccggctcatg gaaacgactg atcatcctgc tgagctgcgt gttcggagga  120
ggaggcacct ccctgcagaa caagaatcct caccagccaa tgaccctgac atggcaggtg  180
ctgtcccaga caggcgacgt ggtgtgggat accaaggcag tgcagccacc ttggacatgg  240
tggccccacc tgaagcctga cgtgtgcgcc ctggccgctc cctgagtc ttgggacatc    300
cccggcacag acgtgagcag cagcaagagg gtgagaccac ccgactctga ttatacagcc  360
gcctacaagc agatcacctg gggcgccatc ggctgtagct atcctcgggc cgcacaagg   420
atggccagtc ccacctttta cgtgtgccca cgcgacggaa ggaccctgtc tgaggcaagg  480
agatgtggcg gcctggagag cctgtattgc aaggagtggg attgtgagac cacaggcaca  540
ggctactggc tgtctaagtc tagcaaggac ctgatcaccg tgaagtggga tcagaacagc   600
gagtggacac agaagttcca gcagtgccac cagaccggtg gtgtaatcc cctgaagatc    660
gactttacag ataagggcaa gctgtccaag gactggatca ccggcaagac atggggcctg   720
agattctacg tgtctggcca ccctggcgtg cagtttacaa tccggctgaa gatcaccaac   780
atgccagcag tggcagtggg accagacctg gtgctggtgg agcagggacc tccacgaac    840
tccctggccc tgccccctcc actgcccct agggaggccc cacccccctag cctgcccgat   900
tctaacagca gccccctggc cacctccgcc cagaccccta cagtgcgcaa gaccatcgtg   960
acactgaata ccccaccccc taccacaggc gacaggctgt cgatctggt gcagggcgcc  1020
tttctgacac tgaacgccac caatcctggc gcaaccgaga gctgctggct gtgcctggct  1080
atgggcccac tactatga ggcaatcgcc tcctctgga aggtggcata ttccacagac    1140
ctggatagat gcagatgggg cacccagggc aagctgaccc tgacagaggt gtctggccac  1200
ggcctgtgca tcggcaaggt gccattcaca caccagcacc tgtgcaacca gaccctgagc  1260
atcaatagct ccggcgacca ccagtacctg ctgccaagca accactcctg gtgggcatgc  1320
tccacaggac tgacccatg tctgagcacc agcgtgttca accagaccag agactttgt    1380
atccaggtgc agctgatccc tcggatctac tattacccag aggaggtgct gctgcaggcc  1440
tatgataatt cccacccaag aacaaagagg gaggccgtgt ctctgaccct ggccgtgctg   1500
ctgggactgg gaatcacagc aggaatcggc acaggcagca ccgccctgat caagggacca   1560
atcgacctgc agcagggact gacctccctg cagatcgcca tcgacgccga tctgagagcc   1620
ctgcaggaca gcgtgtccaa gctggaggat tctctgacct ctctgagcga ggtggtgctg   1680
cagaacagga gggcctgga cctgctgttc ctgaaggagg aggactgtg cgccgccctg    1740
```

```
aaggaggagt gctgttttta tatcgaccac tctggcgccg tgcgggatag catgaagaag    1800
ctgaaggaga agctggataa gcgccagctg gagaggcaga agagccagaa ttggtacgag    1860
ggctggttca acaattcccc ctggtttacc acactgctgt ctaccatcgc aggacctctg    1920
ttattactgc tgctgctgct gatcctgggc ccatgtatca tcaacaagct ggtgcagttt    1980
atcaacgacc gaatctccgc agtgaaaatc taa                                 2013

SEQ ID NO: 9          moltype = AA   length = 669
FEATURE               Location/Qualifiers
source                1..669
                      mol_type = protein
                      organism = Gibbon leukemia virus
SEQUENCE: 9
MVLLPGSMLL TSNLHHLRHQ MSPGSWKRLI ILLSCVFGGG GTSLQNKNPH QPMTLTWQVL     60
SQTGDVVWDT KAVQPPWTWW PTLKPDVCAL AASLESWDIP GTDVSSSKRV RPPDSDYTAA    120
YKQITWGAIG CSYPRARTRM ASSTFYVCPR DGRTLSEARR CGGLESLYCK EWDCETTGTG    180
YWLSKSSKDL ITVKWDQNSE WTQKFQQCHQ TGWCNPLKID FTDKGKLSKD WITGKTWGLR    240
FYVSGHPGVQ FTIRLKITNM PAVAVGPDLV LVEQGPPRTS LALPPPLPPR EAPPPSLPDS    300
NSTALATSAQ TPTVRKTIVT LNTPPPTTGD RLFDLVQGAF LTLNATNPGA TESCWLCLAM    360
GPPYYEAIAS SGEVAYSTDL DRCRWGTQGK LTLTEVSGHG LCIGKVPFTH QHLCNQTLSI    420
NSSGDHQYLL PSNHSWWACS TGLTPCLSTS VFNQTRDFCI QVQLIPRIYY YPEEVLLQAY    480
DNSHPRTKRE AVSLTLAVLL GLGITAGIGT GSTALIKGPI DLQQGLTSLQ IAIDADLRAL    540
QDSVSKLEDS LTSLSEVVLQ NRRGLDLLFL KEGGLCAALK EECCFYIDHS GAVRDSMKKL    600
KEKLDKRQLE RQKSQNWYEG WFNNSPWFTT LLSTIAGPLL LLLLLLILGP CIINKLVQFI    660
NDRISAVKI                                                            669

SEQ ID NO: 10         moltype = DNA   length = 759
FEATURE               Location/Qualifiers
misc_feature          1..759
                      note = Homo sapiens
source                1..759
                      mol_type = other DNA
                      organism = synthetic construct
SEQUENCE: 10
atgatcgaga cctacaatca gacaagccca cggtccgccg caaccggact gcctatcagc     60
atgaagatct tcatgtacct gctgaccgtg tttctgatca cacagatgat cggctccgcc    120
ctgttcgccg tgtatctgca caggagactg gacaagatcg aggatgagcg caatctgcac    180
gaggacttcg tgtttatgaa gaccatccag cggtgcaaca caggcgagag gagcctgtct    240
ctgctgaatt gtgaggagat caagtcccag ttcgagggct tgtgaaggga tatcatgctg    300
aacaaggagg agacaaagaa ggacgaggat ccacagatcg cacacacgt ggtgtccgaa    360
gcaaactcta atgccgccag cgtgctgcag tgggccaaga agggctacta taccatgaag    420
tctaacctgg tgacactgga gaatggcaag cagctgaccc gtgaagaggca gggcctgtac    480
tatatctatg cccaggtgac attctgctct aacagagagg caagctccca ggcacccttc    540
atcgtgggac tgtggctgaa gccctctagc ggcagcggag atcctgct gaaggccgcc    600
aatacccact cctctagcca gctgtgcgag cagcagtcca tccacctggg aggcgttttc    660
gagctgcagc ctggagccag cgtgttcgtg aacgtgacag acccatctca ggtgagccac    720
ggcaccggct tcacaagctt tggcctgctg aagctgtga                          759

SEQ ID NO: 11         moltype = AA   length = 252
FEATURE               Location/Qualifiers
REGION                1..252
                      note = Homo sapiens
source                1..252
                      mol_type = protein
                      organism = synthetic construct
SEQUENCE: 11
MIETYNQTSP RSAATGLPIS MKIFMYLLTV FLITQMIGSA LFAVYLHRRL DKIEDERNLH     60
EDFVFMKTIQ RCNTGERSLS LLNCEEIKSQ FEGFVKDIML NKEETKKDED PQIAAHVVSE    120
ANSNAASVLQ WAKKGYYTMK SNLVTLENGK QLTVKRQGLY YIYAQVTFCS NREASSQAPF    180
IVGLWLKPSS GSERILLKAA NTHSSSQLCE QQSIHLGGVF ELQPGASVFV NVTDPSQVSH    240
GTGFTSFGLL KL                                                        252

SEQ ID NO: 12         moltype = DNA   length = 1416
FEATURE               Location/Qualifiers
source                1..1416
                      mol_type = other DNA
                      organism = Homo sapiens
SEQUENCE: 12
atgctgccct ttctgagcat gctggtgctg ctggtgcagc ctctgggaaa cctgggagcc     60
gagatgaaga gcctgtccca gagatctgtg cctaacacct gcacactggt catgtgcagc    120
cccaccgaga tgactgcctg gaagggac ggaagggatg aagggaggg ccctcggggc    180
gagaagggcg acccaggact gcctggacca atgggactga gcggactgca gggaccaaca    240
ggacctgtgg gaccaaaggg agagaacgga tccgccggag agccaggccc taagggcgag    300
aggggcctgt ctggcccccc tggcctgcca ggcatcccag ccccgccgg caaggagggc    360
ccatccggca gcagggcaa tatcggcccc cagggcgcca ctgcccaaa gggcgaggca    420
ggaccaaagg gagaagtggg agcacctggc atgcagggat ccaccggagc aaagggatct    480
acaggaccaa aggcgagcg cggccccca gcgtgcagga gcgccccgg caatgcagga    540
gcagcaggac cagcaggacc tgcaggccca cagggcgccc ctggctctag ggcccaccc    600
ggcctgaagg gcgacagggg agtgcctggc gataggggca tcaagggaga gagcggactg    660
ccagattccg ccgccctgag gcagcagatg gaggccctga gggcaagct gcagaggctg    720
```

```
gaggtggcct tctcccacta ccagaaggcc gccctgtttc cagacggcca caggagactg    780
gacaagatcg aggatgagcg caacctgcac gaggatttcg tgtttatgaa gaccatccag    840
agatgcaaca caggcgagcg gtctctgagc ctgctgaatt gtgaggagat caagtctcag    900
ttcgagggct tgtgaagga catcatgctg aacaaggagg agaccaagaa ggagaatagc    960
ttcgagatgc agaagggcga tcagaatccc cagatcgcat cacacgtgat cagcgaggca   1020
agctccaaga ccacatccgt gctgcagtgg gccgagaagg gctactatac catgtccaac   1080
aatctggtga cactggagaa cggcaagcag ctgaccgtga agagcagggg cctgtactat   1140
atctatgccc aggtgacatt ctgctctaat cgggaggcct ctagccaggc ccctttatc    1200
gcctctctgt gcctgaagag cccaggcaga ttcgagcgga tcctgctgag ggccgccaac   1260
acccactcct ctgccaagcc atgccaagca cagagcatcc acctgggagg cgtgttcgag   1320
ctgcagccag gagcctccgt gtttgtaaat gtgacagacc catcccaggt gtctcacgga   1380
accggcttca catcctttgg cctgctgaag ctgtga                             1416

SEQ ID NO: 13            moltype = AA   length = 471
FEATURE                  Location/Qualifiers
source                   1..471
                         mol_type = protein
                         organism = Homo sapiens
SEQUENCE: 13
MLPFLSMLVL LVQPLGNLGA EMKSLSQRSV PNTCTLVMCS PTENGLPGRD GRDGREGPRG    60
EKGDPGLPGP MGLSGLQGPT GPVGPKGENG SAGEPGPKGE RGLSGPPGLP GIPGPAGKEG   120
PSGKQGNIGP QGKPGPKGEA GPKGEVGAPG MQGSTGAKGS TGPKGERGAP GVQGAPGNAG   180
AAGPAGPAGP QGAPGSRGPP GLKGDRGVPG DRGIKGESGL PDSAALRQQM EALKGKLQRL   240
EVAFSHYQKA ALFPDGHRRL DKIEDERNLH EDFVFMKTIQ RCNTGERSLS LLNCEEIKSQ   300
FEGFVKDIML NKEETKKENS FEMQKGDQNP QIAAHVISEA SSKTTSVLQW AEKGYYTMSN   360
NLVTLENGKQ LTVKRQGLYY IYAQVTFCSN REASSQAPFI ASLCLKSPGR FERILLRAAN   420
THSSAKPCGQ QSIHLGGVFE LQPGASVFVN VTDPSQVSHG TGFTSFGLLK L            471

SEQ ID NO: 14            moltype = DNA   length = 1412
FEATURE                  Location/Qualifiers
source                   1..1412
                         mol_type = other DNA
                         organism = Mus musculus
SEQUENCE: 14
atgctgccct tcctgagcat gctggtgctg ctggtgcagc ctctgggcaa tctgggcgcc    60
gagatgaagt ccctgtctca gaggagcgtg ccaaacacct gcacactggt catgtgctct   120
ccaaccgaga atggactgcc aggaagggac ggaagagatg gaagggaggg accaaggggga  180
gagaagggcg accctggact gcctggacca atgggactgt ccggactgca gggaccaaca   240
ggcctgtgg gaccaaaggg agagaatgga agcgccggag agcaggaca taagggagag   300
aggggcctgt ccggccccc tggcctgcct ggcatcccag gccccgccgg caaggagggc   360
ccttctggca gcagggcaa catcggacca cagggcaagc ctggaccaaa gggagaggca   420
ggaccaaagg gagaagtggg agcacccggc atgcagggca gcaccggagc aaagggatcc   480
accggcccta agggagagag aggagccct ggagtgcagg gcgcccccag caatgcagga   540
gcagcaggac cagcaggacc tgcaggccca caggggccc caggcagcg ggcccaccc   600
ggcctgaagg gcgacagggg agtgccaggc gataggggca tcaagggaga gtccggactg   660
ccagactctg ccgccctgag gcagcagatg gaggccctga gggcaagct gcagaggctg   720
gaggtggcct tctcccacta ccagaaggcc gccctgtttc cagacgggcca caggagactg  780
gataaggtgg aggaggaggt gaacctgcac gaggatttcg tgttcatcaa gaagctgaag   840
aggtgcaaca agggcgaggg cagcctgtcc ctgctgaatt gtgaggagat gcggcgccag   900
ttcgaggacc tggtgaagga tatcaccctg aacaaggagg agaagaagga gaattctttt   960
gagatgcaga gggcgacga ggatcctcag atcgcagcc acgtggtgtc cgaggcaaac   1020
tctaatgccg ccagcgtgct gcagtgggcc aagaagggct actataccat gaagtctaac   1080
ctggtcatgc tggagaatgg caagcagctg acagtgaaga gagggggcct gtactacgtg   1140
tacacccagg tgacattctg cagcaacaga gagcccagct cccagcggcc ttttatcgtg   1200
ggcctgtggc tgaagcctc tatcggaagc gagaggatcc tgctgaaggc agccaataccc   1260
cactctagct cccagctgtg cgagcagcag tccgtgcacc tgggaggcgt gttcgagctg   1320
caggcaggag caagcgtgtt cgtgaacgga cagaggccag ccaggtcatc cacagagtgg   1380
gcttctctag ctttggcctg ctgaagctgt ga                                 1412

SEQ ID NO: 15            moltype = AA   length = 470
FEATURE                  Location/Qualifiers
source                   1..470
                         mol_type = protein
                         organism = Mus musculus
SEQUENCE: 15
MLPFLSMLVL LVQPLGNLGA EMKSLSQRSV PNTCTLVMCS PTENGLPGRD GRDGREGPRG    60
EKGDPGLPGP MGLSGLQGPT GPVGPKGENG SAGEPGPKGE RGLSGPPGLP GIPGPAGKEG   120
PSGKQGNIGP QGKPGPKGEA GPKGEVGAPG MQGSTGAKGS TGPKGERGAP GVQGAPGNAG   180
AAGPAGPAGP QGAPGSRGPP GLKGDRGVPG DRGIKGESGL PDSAALRQQM EALKGKLQRL   240
EVAFSHYQKA ALFPDGHRRL DKVEEEVNLH EDFVFIKKLK RCNKGEGSLS LLNCEEMRRQ   300
FEDLVKDITL NKEEKKENSF EMQRGDEDPQ IAAHVVSEAN SNAASVLQWA KKGYYTMKSN   360
LVMLENGKQL TVKREGLYYV YTQVTFCSNR EPSSQRPFIV GLWLKPSIGS ERILLKAANT   420
HSSSQLCEQQ SVHLGGVFEL QAGASVFVNV TEASQVIHRV GFSSFGLLKL              470

SEQ ID NO: 16            moltype = DNA   length = 786
FEATURE                  Location/Qualifiers
source                   1..786
                         mol_type = other DNA
                         organism = Homo sapiens
```

```
SEQUENCE: 16
atgatcgaaa catacaacca aacttctccc cgatctgcgg ccactggact gcccatcagc    60
atgaaaattt ttatgtattt acttactgtt tttcttatca cccagatgat tgggtcagca   120
cttttttgctg tgtatcttca tagaaggttg gacaagatag aagatgaaag gaatcttcat   180
gaagattttg tattcatgaa aacgatacag agatgcaaca caggagaaag atccttatcc   240
ttactgaact gtgaggagat taaaagccag tttgaaggct tgtgaagga tataatgtta    300
aacaaagagg agacgaagaa agaaaacagc tttgaaatgc aaaaaggtga tcagaatcct   360
caaattgcgg cacatgtcat aagtgaggcc agcagtaaaa caacatctgt gttacagtgg   420
gctgaaaaag gatactacac catgagcaac aacttggtaa ccctggaaaa tgggaaacag   480
ctgaccgtta aaagacaagg actctattat atctatgccc aagtcacctt ctgttccaat   540
cgggaagctt cgagtcaagc tccatttata gccagcctct gcctaaagtc ccccggtaga   600
ttcgagagaa tcttactcag agctgcaaat acccacagtt ccgccaaacc ttgcgggcaa   660
caatccattc acttgggagg agtatttgaa ttgcaaccag tgcttcggt gtttgtcaat    720
gtgactgatc caagccaagt gagccatggc actggcttca cgtccttgg cttactcaaa    780
ctctga                                                              786

SEQ ID NO: 17           moltype = AA   length = 261
FEATURE                 Location/Qualifiers
source                  1..261
                        mol_type = protein
                        organism = Homo sapiens
SEQUENCE: 17
MIETYNQTSP RSAATGLPIS MKIFMYLLTV FLITQMIGSA LFAVYLHRRL DKIEDERNLH    60
EDFVFMKTIQ RCNTGERSLS LLNCEEIKSQ FEGFVKDIML NKEETKKENS FEMQKGDQNP   120
QIAAHVISEA SSKTTSVLQW AEKGYYTMSN NLVTLENGKQ LTVKRQGLYY IYAQVTFCSN   180
REASSQAPFI ASLCLKSPGR FERILLRAAN THSSAKPCGQ QSIHLGGVFE LQPGASVFVN   240
VTDPSQVSHG TGFTSFGLLK L                                             261

SEQ ID NO: 18           moltype = DNA   length = 783
FEATURE                 Location/Qualifiers
source                  1..783
                        mol_type = other DNA
                        organism = Mus musculus
SEQUENCE: 18
atgatagaaa catacagcca accttccccc agatccgtgg caactggact tccagcgagc    60
atgaagattt ttatgtattt acttactgtt ttccttatca cccaaatgat tggatctgtg   120
cttttttgctg tgtatcttca tagaaggttg gataaggtcg aagaggaagt aaaccttcat   180
gaagattttg tattcataaa aaagctaaag agatgcaaca aggagaagg atctttatcc    240
ttgctgaact gtgaggagat gagaaggcaa tttgaagacc ttgtcaagga tataacgtta   300
aacaaagaag agaaaaaaga aaacagcttt gaaatgcaaa gaggtgatga ggatcctcaa   360
attgcagcac acgttgtaag cgaagccaac agtaatgcag catccgttct acagtgggcc   420
aagaaaggat attataccat gaaaagcaac ttggtaatgc ttgaaaatgg aaacagctg    480
acggttaaaa gagaaggact ctattatgtc tacactcaag tcaccttctg ctctaatcgg   540
gagccttcga gtcaacgccc attcatcgtc ggcctctggc tgaagccag cagtggatct    600
gagagaatct tactcaaggc ggcaaatacc cacagttcct cccagctttg cgagcagcag   660
tctgttcact gggcggagt gtttgaatta caagctggtg cttctgtgtt tgtcaacgtg   720
actgaagcaa gccaagtgat ccacagagtt ggcttctcat ctttcggctt actcaaactc   780
tga                                                                 783

SEQ ID NO: 19           moltype = AA   length = 260
FEATURE                 Location/Qualifiers
source                  1..260
                        mol_type = protein
                        organism = Mus musculus
SEQUENCE: 19
MIETYSQPSP RSVATGLPAS MKIFMYLLTV FLITQMIGSV LFAVYLHRRL DKVEEEVNLH    60
EDFVFIKKLK RCNKGEGSLS LLNCEEMRRQ FEDLVKDITL NKEEKKENSF EMQRGDEDPQ   120
IAAHVVSEAN SNAASVLQWA KKGYYTMKSN LVMLENGKQL TVKREGLYYV YTQVTFCSNR   180
EPSSQRPFIV GLWLKPSSGS ERILLKAANT HSSSQLCEQQ SVHLGGVFEL QAGASVFVNV   240
TEASQVIHRV GFSSFGLLKL                                               260

SEQ ID NO: 20           moltype = DNA   length = 930
FEATURE                 Location/Qualifiers
source                  1..930
                        mol_type = other DNA
                        organism = Mus musculus
SEQUENCE: 20
atggatcagc acacactgga cgtggaggat accgctgacg ctaggcaccc agctggcacc    60
tcctgccctt ctgatgccgc tctgctcgcg gacacaggac tgctggccga tgccgctctg   120
ctgtctgaca cagtgcggcc aaccaacgcc gctctgccaa ccgatgctgc ttaccctgct   180
gtgaacgtga gggacagaga ggctgcttgg ccacctgccc tgaacttctg cagccgccac   240
cctaagctgt acggcctggt ggccctggtg ctgctgctgc tgatcgctgc ttgcgtgcca   300
atctttaccc ggacagagcc acgccccgct ctgacaatca ccacatcccc caacctgggc   360
accgggagga acaacgccga tcaggtgaca ccagtgctct catcggctg acatcccagc    420
acacagcagg gaagcccagt gttcgccaag ctgctggcta gaaccaggc cagcctgtgc   480
aacaccacac tgaactggca cagccaggac ggagctggaa gctcctacct gtcccagggc   540
ctgagatacg aggaggataa gaaggagctg gtggtggact ccctggact gtactacgtg   600
ttcctggagc tgaagctgtc tccaaccctt acaaacaccg ccacaaggt gcagggatgg   660
gtgtctctgg tgctgcaggc taagcccag gtggacgatt cgataacct ggccctgacc    720
```

-continued

```
gtggagctgt tccttgtag catggagaac aagctggtgg acaggtcttg gagccagctg     780
ctgctgctga aggctggcca caggctgtcc gtgggactga gagcctacct gcacggcgcc     840
caggatgctt acagagactg ggagctgagc taccctaaca ccacatcctt cggactgttt     900
ctggtgaagc ctgacaaccc atgggagtga                                      930
```

SEQ ID NO: 21          moltype = DNA  length = 765
FEATURE                Location/Qualifiers
source                 1..765
                       mol_type = other DNA
                       organism = Homo sapiens SEQUENCE: 21
```
atggagtacg cctctgacgc cagcctggat ccagaggccc cttggccacc tgcaccaagg      60
gcccgcgcct gccgcgtgct gccctgggcc ctggtggccg gctgttatt actgctgctg     120
ctggccgcgg cctgcgccgt gttcctggca tgtccttggg ccgtgagcgg agccagagcc     180
tccccaggct ctgccgccag ccctcggctg agagagggac cagagctgtc cccagacgat     240
ccagcaggcc tgctggacct gaggcaggga atgtttgccc agctggtggc ccagaacgtg     300
ctgctgatcg acggccccct gtcctggtac tctgatcctg gcctggccgg cgtgtctctg     360
accggcggcc tgagctataa ggaggataca aaggagctgg tggtggccaa ggccggcgtg     420
tactacgtgt tcttccagct ggagctgagg agagtggtgg caggagaggg ctctggaagc     480
gtgtccctgg ccctgcacct gcagcccctg cggagcgccg caggagccgc cgccctggcc     540
ctgaccgtga acctgccacc agccagctcc gaggcaagga attccgcctt cggctttcag     600
ggcagactgc tgcacctgtc tgccgagaca aggctggtga tgcacctgca caccgaggcc     660
agggcccgcc acgcatggca gctgacccag ggagcaacag tgctgggcct gttccgcgtg     720
acacctgaga tcccagcagg cctgcctagc ccacggtccg agtga                     765
```

SEQ ID NO: 22          moltype = DNA  length = 1389
FEATURE                Location/Qualifiers
source                 1..1389
                       mol_type = other DNA
                       organism = Mus musculus SEQUENCE: 22
```
atgctgcctt tcctgtccat gctggtgctg ctggtgcagc cactgggcaa cctgggagcc      60
gagatgaagt ctctgagcca gcgcagcgtg cctaacacct gcacactggt catgtgctcc     120
cctacagaga acggcctgcc aggaagggac ggaagagatg gaagggaggg accaagggga     180
gagaagggcg accccgagct gcctggacca atgggactga gcggcctgca gggaccaacc     240
ggccccgtgg gacctaaggg agagaacgga tccgctggag agccaggacc taagggagag     300
agaggactgt ctgaccacc tggactgcca ggaatcccag gaccagctgg caaggaggga     360
ccatccggca agcagggaaa catcggacca cagggaaagc ctggaccaaa gggagaggct     420
ggacctaagg gagaagtggg cgccccagga atgcaggagct ctacaggagc taagggcagc     480
accggaccaa agggagagag gggagccccc ggagtgcagg gagcccctgg caacgctgga     540
gccgctggcc cagccggacc cgctggccct caggagcccc ccggctctag ggaccaccaca     600
ggcctgaagg gagacagagg cgtgcccgga gatcgggcca tcaagggaga gagcggcctg     660
cctgactccg ccgctctgag acagcagatg gaggctctgca agaggcaagct gcagcggctg     720
gaggtgggcct tctcccacta ccagaaggcc gctctgtttc ctgacggaag gacagagccc     780
aggcctgctc tgaccatcac cacatctcca aacctgggca aagagagaaa caacgccgat     840
caggtgaccc ccgtgtctca catcggatgc cctaacacca cacagcaggg cagcccgtg     900
tttgccaagc tgctggctaa gaaccaggcc agcctgtgca acaccacact gaactggcac     960
tcccaggatg cgccggaag ctcctacctg tctcaggcc tgcggtacga ggaggacaag    1020
aaggagctgg tggtggatag cccaggctg tactacgtgt tcctggagct gaagctgtcc    1080
cccaccttta caaacaccgg acacaaggtg cagggatgg tgagcctggt gctgcaggct    1140
aagcccagg tggacgattt cgacaacctg gccctgcctg tggacgtgtt tccttgctct    1200
atggagaaca gctggtgga tagatcctgg agccagctgc tgctgctgaa ggctggacac    1260
cgcctgagcg tgggcctgag ggcttacctg cacggagctc aggacgctta cagggactgg    1320
gagctgtcct accctaacac cacatctttt ggcctgtttc tggtgaagcc agacaaccc    1380
tgggagtga                                                           1389
```

SEQ ID NO: 23          moltype = DNA  length = 1389
FEATURE                Location/Qualifiers
source                 1..1389
                       mol_type = other DNA
                       organism = Homo sapiens SEQUENCE: 23
```
atgctgctgt tcctgctgtc cgccctggtg ctgctgaccc agcctctggg ctacctggag      60
gccgagatga gacctattc tcaccggaca atgccaagcg cctgcacact ggtcatgtgc     120
agcagcgtgg agtctggcct gccaggaagg gacggaaggg atggaaggga gggacctaga     180
ggcgagaagg gcgaccctgg cctgccagga gcagcaggac aggcaggaat gcccggccag     240
gccggccca tgggacctaa gggcgacaac ggaagcgtgg agagccagg accaaagggc     300
gataccggcc cttccggacc acctggacca ccaggcgtgc ctgggcccagc cggcagggag     360
ggccctctgg gcaagcaggg caatatcggc ccacagggca agcccggcc taagggcgag     420
gccggcccca ggggcgaagt gggcgcccct ggcatgcagg gaagcgccgg agcccgcggc     480
ctggccggac ctaagggcga gagggcgtg cctggagaga ggggcgtgcc aggaaacaca     540
ggcgcagcag gatctgccgg agcaatggga cccagggca gccctggcgc cagggggccct     600
ccaggcctga aggcgacaa gggcatccca ggcgataagg gagcaagggg agagagcggc     660
ctgccagatg tggcctccc gcgcagcag gtgaggccc tgcaggcca ggtgcagcac     720
ctgcaggcca cctttctca gtacaagaag gtgagctgt tccaaacg cgcctgcccc     780
tgggccgtga gcggagcccg ggcctcccca ggctctgccg ccagccctag gctcgcgag     840
ggaccagagc tgagcccaga cgatccagca ggcctgctgg acctgagaca gggaatgttc     900
gcccagctgg tggcccagaa tgtgctgctg atcgacggcc cactgtcctg gtactctgat     960
ccaggcctgg ccggcgtgtc cctgaccggc ggcctgtctc taaggagga tacaaaggag    1020
```

```
ctggtggtgg ccaaggccgg cgtgtactac gtgttcttcc agctggagct gaggagagtg   1080
gtggcaggag agggatccgg atctgtgagc ctggccctgc acctgcagcc cctgcggtcc   1140
gccgcaggag ccgccgccct ggccctgacc gtggacctgc acctgcctc  tagcgaggca   1200
cgcaattccg ccttcggctt tcagggccgg ctgctgcacc tgtctgccgg acagagactg   1260
ggagtgcacc tgcacaccga ggcccgggcc agacacgcct ggcagctgac ccagggagca   1320
acagtgctgg gcctgtttag ggtgacacct gagatcccga ccgcctgcc  aagccccgc   1380
tccgagtga                                                           1389

SEQ ID NO: 24          moltype = DNA   length = 522
FEATURE                Location/Qualifiers
source                 1..522
                       mol_type = other DNA
                       organism = Mus musculus
SEQUENCE: 24
atggaggaga tgcctctgag ggagagctcc ccacagaggg ccgagagatg caagaagagc    60
tggctgctgt gcatcgtggc tctgctgctg atgctgctgt gctctctggg caccctgatc   120
tacacaagcc tgaagccaac cgccatcgag tcctgtatgg tgaagttcga gctgtctagc   180
tccaagtggc acatgacatc ccccaagcct cactgcgtga acaccacatc tgacggaaag   240
ctgaagatcc tgcagagcgg cacctacctg atctacggac aggtcatccc cgtggacaag   300
aagtacatca aggataacgc ccctttcgtg gtgcagatct acaagaagaa cgacgtgctg   360
cagacactga tgaacgattt tcagatcctg cccatcggcg agtgtacga  gctgcacgct   420
ggcgacaaca tctacctgaa gttcaactcc aaggatcaca tccagaagac caacacatac   480
tggggaatca tcctgatgcc agatctgccc tttatctctt ga                      522

SEQ ID NO: 25          moltype = DNA   length = 600
FEATURE                Location/Qualifiers
source                 1..600
                       mol_type = other DNA
                       organism = Homo sapiens
SEQUENCE: 25
atgaccctgc acccaagccc catcacatgc gagttcctgt tttctaccgc cctgatcagc    60
ccaaagatgt gcctgagcca cctggagaat atgcccctgt cccactctcg gacacaggga   120
gcccagagaa gctcctggaa gctgtggctg ttctgctcta tcgtgatgct gctgttcctg   180
tgcagctttt cctggctgat cttcatcttt ctgcagctgg agacagccaa ggagccttgc   240
atggccaagt ttggccctct gccatccaag tggcagattg cctctagcga gcccccttgc   300
gtgaacaagg tgagcgactg gaagctggag atcctgcaga acggcctgta cctgatctat   360
ggccaggtgg cccccaacgc caattacaac gacgtggccc ttttcgaggt gcggctgtat   420
aagaacaagg atatgatcca gaccctgaca aataagtcta gatccagaa  cgtgggcggc   480
acatacgacc tgcacgtggg cgacaccatc gacctgatct tcaacagcga gcaccaggtg   540
ctgaagaaca atacatattg gggcatcatc ctgctggcca accccagtt  tatctcctga   600

SEQ ID NO: 26          moltype = DNA   length = 1164
FEATURE                Location/Qualifiers
source                 1..1164
                       mol_type = other DNA
                       organism = Mus musculus
SEQUENCE: 26
atgctgcctt tcctgtctat gctggtgctg ctggtgcagc cactgggcaa cctgggagcc    60
gagatgaaga gcctgtccca gagatccgtg cccaacacct gcacactggt catgtgctct   120
cctaccgaga acgcctgcc  aggaagggac ggaagagatg aagggagg   acctcgggga   180
gagaagggcg acccaggact gcctggacca atgggactga gcggcctgca gggaccaaca   240
ggccccgtgg gacctaaggg agagaacgga agcgccggag agccaggacc taagggagag   300
agggggactgt ccgggaccacc tggactgcct ggaatcccag accagctgg  caaggaggga   360
ccatccggca gcaggggaaa catcggacca cagggaaagc ctggaccaaa gggagaggct   420
ggaccaaagg gagaagtggg cgctcctgga atgcagggct ccaccggaac caagggctct   480
acaggaccaa aaggagagag gggagctccc ggagtgcagg gagcccctgg caacgctgga   540
gccgctggcc cagccggacc cgctggccct caggagcccc aggcagcag  ggaccaccc    600
ggcctgaagg gcgacagggg cgtgccagga gatagggga  tcaagggaga gtctggcctg   660
ccagacagcg ccgctctgag acagcagatg gaggccctga gggccaagct gcagcggctg   720
gaggtggctt tctcccacta ccagaaggcc gctctgtttc cagatgcag  cctgaagccc   780
accgccatcg agtcctgcat ggtgaagttt gagctgagct cctctaagtg gcacatgaca   840
tctcccaagc ctcactgcgt gaacaccaca tctgacggca agctgaagat cctgcagagc   900
ggcacctacc tgatctacgg ccaggtcatc cccgtggaca gaagtacat  caaggataac   960
gccccctttcg tggtgcagat ctacaagaag aacgacgtgc tgcagacact gatgaacgat  1020
ttcagatcc tgccaatcgg cgagtgtac  gagctgcacg ctggcgacaa catctacctg   1080
aagttcaact ctaaggatca catccagaag accaacacat actggggcat catcctgatg  1140
ccagatctgc cctttatcag ctga                                          1164

SEQ ID NO: 27          moltype = DNA   length = 1152
FEATURE                Location/Qualifiers
source                 1..1152
                       mol_type = other DNA
                       organism = Homo sapiens
SEQUENCE: 27
atgctgctgt tcctgctgtc tgccctggtg ctgctgaccc agccactggg ctacctggag    60
gccgagatga agacctattc ccaccgcaca atgccttctg cctgcacact ggtcatgtgc   120
agcagcgtgg agagcggcct gccaggaagg acggaagag  atggaaggga gggacccaga   180
ggcgagaagg gcgaccctgg cctgccagga gcagcaggac aggcaggaat gccaggccag   240
gccggccccg tgggccctaa gggcgacaat ggatccgtgg gagagccagg accaaagggc   300
```

```
gataccggcc cttctggacc acctggacca ccaggcgtgc ctggaccagc aggaagagag    360
ggacctctgg gcaagcaggg aaacatcgga ccacagggca agccaggccc taagggcgag    420
gccggcccca agggcgaagt gggcgcccct ggcatgcagg gatccgccgg agccaggggc    480
ctggccggac ctaagggcga gcgcggcgtg cctggagaga gggcgtgcc aggaaataca    540
ggcgcagcag gatctgccgg agcaatggga ccacagggca gccccggcgc cagaggccct    600
ccaggcctga agggcgacaa gggaatccct ggcgataagg gagcaaaggg agagagcggc    660
ctgccagacg tggcctccct gaggcagcag gtggaggccc tgcagggaca ggtgcagcac    720
ctgcaggccg ccttcagcca gtacaagaag gtggagctgt ttccaaatgg cgagacagcc    780
aaggagccct gcatggccaa gttcggccca ctgcccagca agtggcagat ggcctctagc    840
gagccccctt gcgtgaacaa ggtgagcgat tggaagctgg agatcctgca gaacggcctg    900
tacctgatct atggccaggt ggcccccaac gccaattaca acgacgtggc ccctttgag    960
gtgcggctgt ataagaacaa ggatatgatc cagaccctga caaataagtc taagatccag   1020
aacgtgggag caacctacga gctgcacgtg ggcgacacaa tcgacctgat cttcaacagc   1080
gagcaccagg tgctgaagaa caatacatat tgggcatca tcctgctggc caaccccag   1140
tttatctcct ga                                                        1152

SEQ ID NO: 28          moltype = DNA  length = 597
FEATURE                Location/Qualifiers
source                 1..597
                       mol_type = other DNA
                       organism = Mus musculus
SEQUENCE: 28
atggagggcg agggagtgca gcccctggat gagaacctgg agaacggctc ccggcctcgc     60
ttcaagtgga gaagaccct gcggctggtg gtgtctggaa tcaagggcgc cggaatgctg    120
ctgtgcttta tctacgtgtg cctgcagctg agctcctctc ccgccaagga tccccctatc    180
cagaggctga gaggagctgt gaccaggtgc gaggacggac agctgttcat cagctcctac    240
aagaacgagt accagacaat ggaggtgcag aacaacagcg tggtcatcaa gtgtgatggc    300
ctgtacatca tctacctgaa gggatccttc tttcaggagg tgaagatcga cctgcacttt    360
cgggaggatc acaacccaat ctctatcccc atgctgaacg acggcaggag aatcgtgttc    420
acagtggtgg ccagcctggc ttttaaggac aaggtgtacc tgaccgtgaa cgccccagat    480
acactgtgcg agcacctgca gatcaacgac ggagagctga tcgtggtgca gctgaccct    540
ggctactgtg ctccagaggg atcttaccac agcacagtga accaggtgcc cctgtga       597

SEQ ID NO: 29          moltype = DNA  length = 552
FEATURE                Location/Qualifiers
source                 1..552
                       mol_type = other DNA
                       organism = Homo sapiens
SEQUENCE: 29
atggagaggg tgcagcccct ggaggagaac gtgggaaatg ccgcccggcc tagattcgag     60
aggaacaagc tgctgctggt ggcctctgtg atccagggcc tgggcctgct gctgtgcttc    120
acctacatct gtctgcactt ttctgccctg caggtgagcc acagatatcc ccgcatccag    180
agcatcagag tgcagttcac cgagtataag aaggagaagg gctttatcct gacacccctg    240
aaggaggacg agatcatgaa ggtgcagaac aattctgtga tcatcaactg cgatggcttc    300
tacctgatct ccctgaaggg ctattttcct caggaagtga atatcagcct gcactatcag    360
aaggacgagg agccactgtt tcagctgaag aaggtgcgga gcgtgaattc cctgatggtg    420
gccagcctga cctacaagga caaggtgtat ctgaacgtga ccacagataa tacatccctg    480
gacgatttcc acgtgaacgg cggcgagctg atcctgatcc accagaatcc cggcgagttt    540
tgcgtgctgt ga                                                        552

SEQ ID NO: 30          moltype = DNA  length = 1215
FEATURE                Location/Qualifiers
source                 1..1215
                       mol_type = other DNA
                       organism = Mus musculus
SEQUENCE: 30
atgctgccct tcctgtccat gctggtgctg ctggtgcagc ctctgggcaa cctgggagcc     60
gagatgaagt ctctgagcca gagatccgtg ccaaacacct gcacactggt catgtgctct    120
cccaccgaga acgcctgcc tggaaggac ggaagagatg gaaggagg acccccgggga     180
gagaagggcg atcctggact gccaggacct atgggactga gcggcctgca gggaccaaca    240
ggccccgtgg gacctaaggg agagaacgga agcgccggag agccaggacc aaagggagag    300
aggggactgt ccggccacac tggactgcct ggaatccctg gaccagctgg caaggaggga    360
ccttccggca agcagggaaa catcggacca cagggaaagc caggacctaa gggagaggct    420
gaccaaaagg gagaagtggg cgctcccgga atgcagggct ctacggacc caaggcgagc    480
acaggaccta agggagagag gggagctcca ggagtgcagg gagccccggg caacgctgga    540
gctgctggac cagctggacc agctggccct cagggagccc caggctctag ggaccaccca    600
ggcctgaagg gcgacagggg cgtgccagga gataggggca tcaagggaga gagcggcctg    660
ccagattccg ccgctctgag acagcagatg gaggccctga ggcggcaagct cggcggcctg    720
gaggtggctt tcagccacta ccagaaggcc gctctgtttc ctgacggcga ctcctctcca    780
gccaaggatc ctccaatcca gcggctgcgc cgagctgtga ccaggcgcga ggatggccag    840
ctgttcatca gctcctacaa gaacgagtac cagacaatgg aagtgcagaa caactctgtg    900
gtcatcaagt gtgacggcct gtacatcatc tacctgaagg gcagcttctt tcaggaggtg    960
aagatcgacc tgcactttag agaggatcac aacccaatct ccatccccat gctgaacgac   1020
ggcaggaaa tcgtgttcac cgtggtggcc tctctggctt taaggacaa ggtgtacctg   1080
accgtgaacg ccccgatac actgtgcgag cacctgcaga tcaacgacgg cgagctgatc   1140
gtggtgcagc tgacccctgg atactgcgct ccagagggct cctaccactc tacagtgaac   1200
caggtgcctc tgtga                                                    1215

SEQ ID NO: 31          moltype = DNA  length = 1170
```

```
FEATURE                 Location/Qualifiers
source                  1..1170
                        mol_type = other DNA
                        organism = Homo sapiens
SEQUENCE: 31
atgctgctgt tcctgctgag cgccctggtg ctgctgaccc agccactggg ctacctggag   60
gccgagatga agacctattc ccacagaaca atgccttctg cctgcacact ggtcatgtgc  120
agcagcgtgg agtccggcct gccaggaagg acggcagag atggcaggga gggcccagg   180
ggcgagaagg gcgacccgg cctgcctgga gcagcaggcc aggccggcat gccaggccag  240
gccggcccag tgggcccaa gggcgacaac ggcagcgtgg gcgagcccgg ccctaagggc  300
gataccggcc cctccggccc ccctggccca cccggcgtgc caggaccagc aggaagggag  360
ggaccactgg gcaagcaggg caatatcgga cctcagggca gcctggaccc aaagggagag  420
gcaggaccaa agggagaagt gggcgcccct ggcatgcagg gatctgccgg agcccgggc   480
ctggccggcc ccaagggcga gagggccgtg cccggccaga ggggcgtgcc tggcaacaca  540
ggcgccgccg gctccgccgg cgccatggga cctcagggct ctccaggagc cagaggccct  600
ccaggcctga gggcgacaa gggaatcct ggcgataagg gagcaaaggg agagagcggc   660
ctgccagacg tggcctccct gcggcagcag gtggaggccc tgcagggcca ggtgcagcac  720
ctgcaggccg ccttcagcca gtacaagaag gtggagctgt ttcctaatgg cgtgtctcac  780
cgctacccac ggatccagag catcaaggtg cagttcaccg agtataagaa ggagaagggc  840
tttatcctga catctcagaa ggaggacgag atcatgaagg tgcagaacaa tagcgtgatc  900
atcaactgcg atggcttcta cctgatcagc ctgaagggct attttcccca ggaagtgaat  960
atctctctgc actatcagaa ggatgaggag cctctgtttc agctgaagaa ggtgagatct 1020
gtgaacagcc tgatggtggc ctccctgacc tacaaggaca aggtgtatct gaacgtgacc 1080
acagataata catctctgga cgatttccac gtgaacggcg gcgagctgat cctgatccac 1140
cagaatcccg gcgagttttg cgtgctgtga                                   1170

SEQ ID NO: 32          moltype = DNA  length = 969
FEATURE                 Location/Qualifiers
source                  1..969
                        mol_type = other DNA
                        organism = Mus musculus
SEQUENCE: 32
atgcagctga agtgtccatg cttcgtgtcc ctgggaacaa gacagcccgt ctggaagaaa   60
ctgcacgtga gctccggctt cttttagcgg ctggggctgt ttctgctgct gctgtctagt  120
ctgtgcgccg cttccgcaga gactgaagtc ggagccatgg tggcagtaa cgtggtcctg  180
tcatgcatcg acccacaccg acggcatttc aacctgtctg gcctgtacgt gtattggcag  240
attgagaatc ccgaagtgtc agtcacctac tatctgcctt acaagagccc agggatcaac  300
gtggactcaa gctataaaaa tagggggcac ctgtccctgg attctatgaa gcaggaaaac  360
ttcagcctgt acctgaaaaa tgtgaccct caggacacaa aggagttcac ttgtcgcgtc  420
tttatgaaca ctgcaaccga actggtgaag attctggagg aagtggtccg gctgagagtc  480
gcagccaact ttagcactcc tgtgatctct accagtgatt cctctaatcc aggccaggag  540
cggacatata cttgcatgtc taagaacgga taccccgaac ctaatctgta ttggatcaac  600
accacagaca atagtctgat tgataccgct ctgcagaaca atacagtcta ctgtaacaag  660
ctggggctgt atgacgtgat ctctactctg cggctgccat ggaccagtag aggagatgtg  720
ctgtgctgcg tggagaacgt ggccctgcac cagaatatca cctcaattag ccaggctgag  780
tcctttaccg gcaacaatac aaagaatcct caggagacac ataacaatga actgaaagtg  840
ctggtgccag tgctggccgt cctggctgca gcagctttcg tgtcttttat catctacaga  900
aggacccgcc ctcaccgctc atacactgga cctaagaccg tgcagctgga actgacagac  960
catgcttga                                                         969

SEQ ID NO: 33          moltype = DNA  length = 909
FEATURE                 Location/Qualifiers
source                  1..909
                        mol_type = other DNA
                        organism = Homo sapiens
SEQUENCE: 33
atgcgtctgg gttcacctgg tctgctgttt ctgctgtttt caagtctgcg tgctgatact   60
caggagaagg aagtccgggc tatggtcgga agtgacgtgg agctgtcatg cgcttgtccc  120
gaagggtccc ggttcgacct gaacgatgtc tacgtgtatt ggcagaccc tgagagtaag  180
accgtggtca cataccacat ccctcagaac tccagcctgg aaaatgtgaa ttcaaggtat  240
cggaacagag ccctgatgtc ccctgctggc atgctgcggg gagacttctc tctgagactg  300
tttaatgtga caccacagga tgagcagaaa ttccattgcc tggtcctgtc acagtccctg  360
ggatttcagg aggtgctgag tgtcgaagtg actctgcacg tcgccgctaa ttctctccgtg  420
cctgtggtca gcgcaccaca tagccccctct caggacgagc tgaccttac atgtactttc   480
atcaacggct accccgccc taacgtgtac tggattaaca agactgacaa tagcctgctg  540
gatcaggcac tgcagaacga caccgtgttt ctgaatatgc gaggactgta cgatgtggtc  600
agcgtcctgc gtattgccag gaccccatct gtgaacatcg ggtgctgtat tgagaacgtc  660
ctgctgcagc agaatctgac agtggggagc cagactggta atgacatcgg cgagagggat  720
aagattaccg aaaaccccgc gagtacaggc gagaagaacg cagccacatg gtcaatcctg  780
gctgtgctgt gcctgctggt ggtcgtggct gtcgcaattg ctgggtgtg ccgcgatcgg  840
tgtctgcagc actcttatgc cggtgcttgg gcagtgagtc cagagactga actgaccggc  900
catgtctaa                                                         909

SEQ ID NO: 34          moltype = DNA  length = 1574
FEATURE                 Location/Qualifiers
source                  1..1574
                        mol_type = other DNA
                        organism = Mus musculus
SEQUENCE: 34
```

```
cttaagatgg aaactgatac tctgctgctc tgggtgctgc tcctctgggt gcctggttca  60
actggggaca ttcgacgggc tgacattgtg atgacccaga ccacactgag cctgcccgtg 120
tccctgggcg accaggccag catctcctgc cggagctccc agtctatcgt gcacagcaac 180
ggaaacacat acctggagtg gtatctgcag aagcctggcc agtccccaaa gctgctgatc 240
tacaaggtgt ccaacaggtt cagcggcgtg cctgaccgct tttctggaag cggctccgga 300
acagatttca ccctgaagat cagcagggtg gaggctgagg acctgggcgt gtactactgc 360
ttccagggat cccacgtgcc ttacaccttt ggcggaggca caaagctgga gatcaagaga 420
gccgatgctg ctccaaccgt gtctggaagc ggaggcgggg gttctggagg cggtgggagc 480
ggtggcggag ggtctgaggc taagctgcag gagagcggcc ccgtgctggt gaagcctgga 540
gccagcgtga agatgtcctg taaggcttct ggatacacct tcacagacta ctacatgaac 600
tgggtgaagc agagccacgg caagtccctg gagtggatcg gagtgatcaa cccttacaac 660
ggcgacacct cttacaacca gaagtttaag ggcaaggcca ccctgacagt ggataagtct 720
agctccaccg cttacatgga gctgaacagc ctgcatccg aggattctgc cgtgtactac 780
tgtgctaggt actacggaag ctggttcgcc tactgggcc agggaaact gatcaccgtg 840
tccacagcca agaccacacc ccctagcgtg taccccctgg ctcctaggtc tagcagaggc 900
tgcaagccat gcatctgtac cgtgcccgag gtgagcagcg tgttcatctt tccacccaag 960
cccaaggacg tgctgaccat cacactgacc cctaaggtga catgcgtggt ggtggatatc 1020
agcaaggacg atccagaggt gcagttctcc tggtttgtgg acgatgtgga ggtgcacacc 1080
gcccagacac agccaaggga ggagcagttc aactccacct ttagatccgt gtctgagctg 1140
cccatcatgc accaggactg gctgaacgga aaggagttca gtgccgggt gaactccgcc 1200
gcttttcctg ctccaatcga gaagaccatc tctaagacaa agggccgccc aaaggctcca 1260
caggtgtaca ccatccctcc acccaaggag cagatgccta aggataaggt gagcctgacc 1320
tgtatgatca cagacttctt tcccgaggat atcacagtgg agtggcagtg aacggacag 1380
cctgccgaga actacaagaa cacccagcca atcatggaca cagatggctc ttacttcgtg 1440
tacagcaagc tgaacgtgca gaagtctaac tgggaggctg caacaccttc acctgcagc 1500
gtgctgcacg aaggtctcca taatcaccac accgaaaaga gcctcagtca cagccctggg 1560
aaatgaggcg cgcc                                                  1574

SEQ ID NO: 35         moltype = DNA   length = 1484
FEATURE               Location/Qualifiers
source                1..1484
                      mol_type = other DNA
                      organism = Homo sapiens
SEQUENCE: 35
cttaagatgg aaactgacac cctgctgctg tgggtcctgc tgctgtgggt gcctggatcc  60
accggcgata tcgtgctgac ccagtctcct ggcacactga gtctgtcacc aggggagcga 120
gcaacactgt cttgtagagc cagccagtct gtgggaagct cctacctggc ttggtatcag 180
cagaagccag gccaggcacc caggctgctg atctacggag ccttcagccg ggccactggc 240
attccagaca ggttctctgg aagtggctca gggaccgact tcaccctgac catcagccga 300
ctggagcccg aagacttcgc cgtgtactat tgccagcagt acggctctag tccttggact 360
tttggacagg gcaccaaagt ggagatcaag cgcggcgggg gaggctctgg ggaggcgggg 420
agtggaggcg ggggatcaca ggtccagctg gtggaaagcg gcgggggagt ggtccagcca 480
ggccggagcc tgcggctgag ctgcgccgct tcaggattca cattttcaag tatataccatg 540
cactgggtcc ggcaggcacc agggaaggga ctggagtggg tgaccttcat cagctatgac 600
ggcaacaaca gtattacgc tgattccgtg aaagggaggt ttaccattag ccgcgacaac 660
tccaaaaata cactgtacct gcagatgaac agcctgcggg ccgaggatac tgctatctac 720
tattgcgcaa gaaccgggtg gctgggaccc ttcgactatt ggggccaggg gactctggtc 780
accgtgtcct ctgataagac acacacatgc cctcccctgtc ctgcaccaga gctgctgggc 840
gggccatccg tgttcctgtt tccacccaag cctaaagaca ccctgatgat cagccggaca 900
cctgaagtca cttgcgtggt cgtggacgtg agtcacgagg atcagaagt caagtttaac 960
tggtacgtgg atggcgtcga ggtgcataat gccaagacca aacctcgcga ggaacagtac 1020
aatagcacat atcgagtcgt gtccgtcctg actgtgctgc atcaggattg gctgaacggc 1080
aaagagtata agtgcaaagt gagcaataag gcactgcctg cccaatcga gaaaacaatt 1140
tccaaggcta aaggccagcc cagggaacct caggtgtaca ctctgcctcc aagtcgcgag 1200
gaaatgacca agaaccaggt gagcctgacc tgtctggtga aagggttcta tccatcagac 1260
attgcagtgg agtgggaaag caatggacag cccgaaaaca attacaagac cacaccccct 1320
gtgctggaca gcgatggctc cttctttctg tattctaagc tgactgtgga taaagtcgc 1380
tggcagcagg ggaacgtctt tagctgttcc gtgatgcatg aggctctgca caatcattac 1440
acacagaagt ctctgagtct gtcacccggc aaatgaggcg cgcc                 1484

SEQ ID NO: 36         moltype = DNA   length = 632
FEATURE               Location/Qualifiers
misc_feature          1..632
                      note = CMV promoter
source                1..632
                      mol_type = other DNA
                      organism = synthetic construct
SEQUENCE: 36
gttgacattg attattgact agttattaat agtaatcaat tacgggggtca ttagttcata  60
gcccatatat ggagttccgc gttacataac ttacggtaaa tggcccgcct ggctgaccgc 120
ccaacgaccc ccgcccattg acgtcaataa tgacgtatgt tcccatagta acgccaatag 180
ggactttcca ttgacgtcaa tgggtggagt atttacggta aactgcccac ttggcagtac 240
atcaagtgta tcatatgcca agtacgcccc ctattgacgt caatgacggt aaatggcccg 300
cctggcatta tgcccagtac atgaccttat gggactttcc tacttggcag tacatctacg 360
tattagtcat cgctattacc atggtgatgc ggttttggca gtacatcaat gggcgtggat 420
agcggtttga ctcacgggga tttccaagtc tccaccccat tgacgtcaat gggagtttgt 480
tttggcacca aaatcaacgg gactttccaa aatgtcgtaa caactccgcc ccattgacgc 540
aaatgggcgg taggcgtgta cggtgggagg tctatataag cagagctctc tggctaacta 600
gagaacccac tgcttactgg cttatcgaaa tt                               632
```

```
SEQ ID NO: 37               moltype = DNA  length = 394
FEATURE                     Location/Qualifiers
misc_feature                1..394
                            note = RSV promoter
source                      1..394
                            mol_type = other DNA
                            organism = synthetic construct
SEQUENCE: 37
tgtacgggcc agatatacgc gtatctgagg ggactagggt gtgtttaggc gaaaagcggg    60
gcttcggttg tacgcggtta ggagtcccct caggatatag tagtttcgct tttgcatagg   120
gagggggaaa tgtagtctta tgcaatacac ttgtagtctt gcaacatggt aacgatgagt   180
tagcaacatg ccttacaagg agagaaaaag caccgtgcat gccgattggt ggaagtaagg   240
tggtacgatc gtgccttatt aggaaggcaa cagacagtgt tgacatggat tggacgaacc   300
actgaattcc gcattgcaga gataattgta tttaagtgcc tagctcgata caataaacgc   360
catttgacca ttcaccacat tggtgtgcac ctcc                               394

SEQ ID NO: 38               moltype = DNA  length = 188
FEATURE                     Location/Qualifiers
misc_feature                1..188
                            note = BGH polyA
source                      1..188
                            mol_type = other DNA
                            organism = synthetic construct
SEQUENCE: 38
ctgtgccttc tagttgccag ccatctgttg tttgcccctc ccccgtgcct tccttgaccc    60
tggaaggtgc cactcccact gtcctttcct aataaaatga ggaaattgca tcgcattgtc   120
tgagtaggtg tcattctatt ctggggggtg ggtggggca ggacagcaag ggggaggatt    180
gggaagac                                                            188

SEQ ID NO: 39               moltype = DNA  length = 249
FEATURE                     Location/Qualifiers
misc_feature                1..249
                            note = SV40 late polyA
source                      1..249
                            mol_type = other DNA
                            organism = synthetic construct
SEQUENCE: 39
gacatgataa gatacattga tgagtttgga caaaccacaa ctagaatgca gtgaaaaaaa    60
tgctttattt gtgaaatttg tgatgctatt gctttatttg tgaaatttgt gatgctattg   120
ctttatttgt aaccattata agctgcaata aacaagttaa caacaacaat tgcattcatt   180
ttatgtttca ggttcagggg gaggtgtggg aggttttttta aagcaagtaa aacctctaca   240
aatgtggta                                                           249

SEQ ID NO: 40               moltype = DNA  length = 345
FEATURE                     Location/Qualifiers
misc_feature                1..345
                            note = SV40 enhancer promoter
source                      1..345
                            mol_type = other DNA
                            organism = synthetic construct
SEQUENCE: 40
gctgtggaat gtgtgtcagt tagggtgtgg aaagtcccca ggctcccag caggcagaag     60
tatgcaaagc atgcatctca attagtcagc aaccaggtgt ggaaagtccc caggctcccc   120
agcaggcaga agtatgcaaa gcatgcatct caattagtca gcaaccatag tcccgcccct   180
aactccgccc atcccgcccc taactccgcc cagttccgcc cattctccgc cccatggctg   240
actaattttt tttatttatg cagaggccga ggccgcctcg gcctctgagc tattccagaa   300
gtagtgagga ggctttttttg gaggcctagg cttttgcaaa aagct                  345

SEQ ID NO: 41               moltype = DNA  length = 99
FEATURE                     Location/Qualifiers
misc_feature                1..99
                            note = Rabbit beta-globin polyA
source                      1..99
                            mol_type = other DNA
                            organism = synthetic construct
SEQUENCE: 41
gacctctggc taataaagga aatttatttt cattgcaata gtgtgttgga attttttgtg    60
tctctcactc ggaaggacat atgggagggc aaatcattt                           99

SEQ ID NO: 42               moltype = DNA  length = 723
FEATURE                     Location/Qualifiers
misc_feature                1..723
                            note = GFP
source                      1..723
                            mol_type = other DNA
                            organism = synthetic construct
SEQUENCE: 42
accatggtga gcaagggcga ggagctgttc accggggtgg tgcccatcct ggtcgagctg    60
```

```
gacggcgacg taaacggcca caagttcagc gtgtccggcg agggcgaggg cgatgccacc    120
tacggcaagc tgaccctgaa gttcatctgc accaccggca agctgcccgt gccctggccc    180
accctcgtga ccaccctgac ctacggcgtg cagtgcttca gccgctaccc cgaccacatg    240
aagcagcacg acttcttcaa gtccgccatg cccgaaggct acgtccagga gcgcaccatc    300
ttcttcaagg acgacggcaa ctacaagacc cgcgccgagg tgaagttcga gggcgacacc    360
ctggtgaacc gcatcgagct gaagggcatc gacttcaagg aggacggcaa catcctgggg    420
cacaagctgg agtacaacta caacagccac aacgtctata tcatggccga caagcagaag    480
aacggcatca aggtgaactt caagatccgc cacaacatcg aggacggcag cgtgcagctc    540
gccgaccact accagcagaa cacccccatc ggcgacggcc ccgtgctgct gcccgacaac    600
cactacctga gcacccagtc cgccctgagc aaagacccca acgagaagcg cgatcacatg    660
gtcctgctgg agttcgtgac cgccgccggg atcactctcg gcatggacga gctgtacaag    720
taa                                                                 723

SEQ ID NO: 43          moltype = DNA  length = 454
FEATURE                Location/Qualifiers
misc_feature           1..454
                       note = MoMuLV LTR
source                 1..454
                       mol_type = other DNA
                       organism = synthetic construct
SEQUENCE: 43
ttaattaagt aacgccattt tgcaaggcat ggaaaaatac ataactgaga atagagaagt     60
tcagatcaag gtcaggaaca gatggaacag ctgaatatgg gccaaacagg atatctgtgg    120
taagcagttc ctgccccggc tcagggccaa gaacagatga acagctgaa tatgggccaa    180
acaggatatc tgtggtaagc agttcctgcc ccggctcagg gccaagaaca gatggtcccc    240
agatgcggtc cagccctcag cagtttctag agaaccatca gatgtttcca gggtgcccca    300
aggacctgaa atgaccctgt gccttatttg aactaaccaa tcagttcgct tctcgcttct    360
gttcgcgcgc ttctgctccc cgagctcaat aaaagagccc acaacccctc actcggggcg    420
ccagtcctcc gattgactga gtcgcccgct taag                                454

SEQ ID NO: 44          moltype = DNA  length = 1349
FEATURE                Location/Qualifiers
misc_feature           1..1349
                       note = EF1alpha promoter
source                 1..1349
                       mol_type = other DNA
                       organism = synthetic construct
SEQUENCE: 44
ttaattaaga gtaattcata caaaaggact cgcccctgcc ttggggaatc ccagggaccg     60
tcgttaaact cccactaacg tagaacccag agatcgctgc gttcccgccc cctcacccgc    120
ccgctctcgt catcactgag gtggagaaga gcatgcgtga ggctccggtg cccgtcagtg    180
ggcagagcgc acatcgccca cagtccccga aagttggggg gaggggtcg gcaattgaac    240
cggtgcctag agaaggtggc gcggggtaaa ctgggaaagt gatgtcgtgt actggctccg    300
cctttttccc gagggtgggg gagaaccgta tataagtgca gtagtcgccg tgaacgttct    360
ttttcgcaac gggtttgccg ccagaacaca ggtaagtgcc gtgtgtggtt cccgcgggcc    420
tggcctcttt acgggttatg gcccttgcgt gccttgaatt acttccacgc ccctggctgc    480
agtacgtgat tcttgatccc gagcttcggg ttggaagtgg gtgggagagt tcgaggcctt    540
gcgcttaagg agccccttcg cctcgtgctt gagttgaggc ctggcttggg cgctggggcc    600
gccgcgtgcg aatctggtgg caccttcgcg cctgtctcgc tgctttcgat aagtctctag    660
ccatttaaaa ttttttgatga cctgctgcga cgctttttttt ctggcaagat agtcttgtaa    720
atgcgggcca agatctgcac actggtattt cggtttttgg ggccgcgggc ggcgacgggg    780
cccgtgcgtc ccagcgcaca tgttcggcga ggcggggcct gcgagcgcgg ccaccgagaa    840
tcggacgggg gtagtctcaa gctggccggc ctgctctggt gcctggcctc gcgccgccgt    900
gtatcgcccc gccctgggcg gcaaggctgg cccggtcggc accagttgcg tgagcggaaa    960
gatggcggct tccggccct gctgcaggga gctcaaaatg gaggacgcgg cgctcgggag   1020
agcgggcggg tgagtcaccc acacaaagga aaagggcctt tccgtcctca gccgtcgctt   1080
catgtgactc cacggagtac cgggcgccgt ccaggcacct cgattagttc tcgagctttt   1140
ggagtacgtc gtctttaggt tggggggagg ggttttatgc gatggagttt ccccacactg   1200
agtgggtgga gactgaagtt aggccagctt ggcacttgat gtaattctcc ttggaatttg   1260
cccttttga gtttggatct tggttcattc tcaagcctca gacagtggtt caaagttttt   1320
ttcttccatt tcaggtgtcg tgacttaag                                     1349

SEQ ID NO: 45          moltype = DNA  length = 481
FEATURE                Location/Qualifiers
misc_feature           1..481
                       note = HGH polyA
source                 1..481
                       mol_type = other DNA
                       organism = synthetic construct
SEQUENCE: 45
gacgggtggc atccctgtga cccctcccca gtgcctctcc tggccctgga agttgccact     60
ccagtgccca ccagccttgt cctaataaaa ttaagttgca tcattttgtc tgactaggtg    120
tccttctata atattatggg gtggagggg tggtatgga gcaagggca agttgggaag    180
acaacctgta gggcctgcgg ggtctattgg gaaccaagct ggagtgcagt ggcacaatct    240
tggctcactg caatctccgc ctcctgggtt caagcgattc tcctgcctca gcctcccgag    300
ttgttgggat tccaggcatg catgaccagg ctcagctaat tttgtttttt ttggtagaga    360
```

```
-continued
cggggtttca ccatattggc caggctggtc tccaactcct aatctcaggt gatctaccca    420
ccttggcctc ccaaattgct gggattacag gcgtgaacca ctgctccctt ccctgtcctt    480
t                                                                   481
```